(12) United States Patent
Collinson et al.

(10) Patent No.: US 11,931,226 B2
(45) Date of Patent: Mar. 19, 2024

(54) WOUND DRESSING SEALANT AND USE THEREOF

(71) Applicant: Smith & Nephew PLC, Watford (GB)

(72) Inventors: Sarah Jenny Collinson, Hull (GB); Nicholas Charlton Fry, Pocklington (GB); Philip Gowans, Doncaster (GB); Edward Yerbury Hartwell, Hull (GB); Marcus Damian Phillips, Wakefield (GB)

(73) Assignee: Smith & Nephew PLC, Watford (GB)

( * ) Notice: Subject to any disclaimer, the term of this patent is extended or adjusted under 35 U.S.C. 154(b) by 637 days.

(21) Appl. No.: 16/779,436

(22) Filed: Jan. 31, 2020

(65) Prior Publication Data

US 2020/0170843 A1    Jun. 4, 2020

Related U.S. Application Data

(62) Division of application No. 14/776,088, filed as application No. PCT/GB2014/050786 on Mar. 14, 2014, now abandoned.
(Continued)

(30) Foreign Application Priority Data

May 30, 2013   (GB) ..................................... 1309662
May 30, 2013   (GB) ..................................... 1309709

(51) Int. Cl.
*A61F 13/02*        (2006.01)
*A61F 13/00*        (2006.01)
(Continued)

(52) U.S. Cl.
CPC .... *A61F 13/0253* (2013.01); *A61F 13/00068* (2013.01); *A61F 13/0216* (2013.01);
(Continued)

(58) Field of Classification Search
CPC ......... A61F 13/00029; A61F 13/00068; A61L 15/26; A61L 15/42; A61L 15/425
See application file for complete search history.

(56) References Cited

U.S. PATENT DOCUMENTS 3,274,155 A    9/1966    Saunders et al.
3,646,155 A    2/1972    Scott et al.
(Continued)

FOREIGN PATENT DOCUMENTS

DE    34 43 101    5/1986
DE    3 838 587    5/1990
(Continued)

OTHER PUBLICATIONS

US 6,216,701 B1, 04/2001, Heaton et al. (withdrawn)
(Continued)

*Primary Examiner* — Nicholas J. Weiss
*Assistant Examiner* — Gabriella E Burnette
(74) *Attorney, Agent, or Firm* — Knobbe, Martens Olson & Bear, LLP

(57) ABSTRACT

Embodiments disclosed herein are directed to sealing compositions for negative pressure treatment systems and wound dressing systems, devices containing the same, apparatuses, uses and methods for creating a main wound dressing portion for use in wound care, more particularly for sealing a trimmable dressing, having a main dressing portion or cell in fluid (e.g., gas) communication with additional dressing portions or cells, for use in woundcare, more particularly that may be used for the treatment of wounds. In particular, some embodiments are directed to compositions for improving the versatility of wound dressings for wounds of different shapes or sizes.

17 Claims, 25 Drawing Sheets

Related U.S. Application Data

(60) Provisional application No. 61/907,350, filed on Nov. 21, 2013, provisional application No. 61/906,865, filed on Nov. 20, 2013, provisional application No. 61/829,187, filed on May 30, 2013, provisional application No. 61/828,604, filed on May 29, 2013, provisional application No. 61/800,040, filed on Mar. 15, 2013.

(51) Int. Cl.
  *A61F 13/0246* (2024.01)
  *A61L 15/42* (2006.01)
  *A61L 15/58* (2006.01)
  *A61M 1/00* (2006.01)

(52) U.S. Cl.
  CPC .............. *A61L 15/42* (2013.01); *A61L 15/58* (2013.01); *A61M 1/90* (2021.05)

(56) References Cited

U.S. PATENT DOCUMENTS

| | | | |
|---|---|---|---|
| 3,783,870 | A | 1/1974 | Schachet |
| 3,808,178 | A | 4/1974 | Gaylord |
| 3,809,086 | A | 5/1974 | Schachet et al. |
| 3,809,087 | A | 5/1974 | Lewis, Jr. |
| 3,928,629 | A | 12/1975 | Chandra et al. |
| 3,972,328 | A | 8/1976 | Chen |
| 4,029,598 | A | 6/1977 | Neisius et al. |
| 4,073,294 | A | 2/1978 | Stanley et al. |
| 4,117,551 | A | 9/1978 | Books et al. |
| 4,266,545 | A | 5/1981 | Moss |
| 4,278,089 | A | 7/1981 | Huck et al. |
| 4,392,860 | A | 7/1983 | Huck et al. |
| 4,529,553 | A | 7/1985 | Faltynek |
| 4,538,920 | A | 9/1985 | Drake et al. |
| 4,569,674 | A | 2/1986 | Phillips |
| 4,578,060 | A | 3/1986 | Huck et al. |
| 4,655,754 | A | 4/1987 | Richmond et al. |
| 4,661,093 | A | 4/1987 | Beck et al. |
| 4,713,052 | A | 12/1987 | Beck et al. |
| 4,714,739 | A | 12/1987 | Arkles |
| 4,720,431 | A | 1/1988 | Wong |
| 4,728,499 | A | 3/1988 | Fehder |
| 4,753,536 | A | 6/1988 | Spehar et al. |
| 4,767,026 | A | 8/1988 | Keller |
| 4,771,919 | A | 9/1988 | Ernst |
| 4,791,149 | A | 12/1988 | Pocknell |
| 4,798,583 | A | 1/1989 | Beck et al. |
| 4,813,942 | A | 3/1989 | Alvarez |
| 4,826,494 | A | 5/1989 | Richmond et al. |
| 4,838,253 | A * | 6/1989 | Brassington ...... A61F 13/00008 128/DIG. 21 |
| 4,872,450 | A | 10/1989 | Austad |
| 4,923,444 | A | 5/1990 | Daoud et al. |
| 4,936,834 | A | 6/1990 | Beck et al. |
| 4,969,880 | A | 11/1990 | Zamierowski |
| 4,991,574 | A | 2/1991 | Pocknell |
| 5,004,643 | A | 4/1991 | Caldwell |
| 5,010,115 | A | 4/1991 | Grisoni |
| 5,033,650 | A | 7/1991 | Colin et al. |
| 5,056,510 | A | 10/1991 | Gilman |
| 5,064,653 | A | 11/1991 | Sessions et al. |
| 5,080,493 | A | 1/1992 | McKown et al. |
| 5,089,606 | A | 2/1992 | Cole et al. |
| 5,100,395 | A | 3/1992 | Rosenberg |
| 5,141,503 | A | 8/1992 | Sewell, Jr. |
| 5,145,933 | A | 9/1992 | Grisoni et al. |
| 5,153,231 | A | 10/1992 | Bouquet et al. |
| 5,181,905 | A | 1/1993 | Flam |
| 5,238,732 | A | 8/1993 | Krishnan |
| 5,249,709 | A | 10/1993 | Duckworth et al. |
| 5,266,326 | A | 11/1993 | Barry et al. |
| 5,333,760 | A | 8/1994 | Simmen et al. |
| 5,348,392 | A | 9/1994 | Bouquet et al. |
| 5,397,848 | A | 3/1995 | Yang et al. |
| 5,456,745 | A | 10/1995 | Rorefer et al. |
| 5,549,584 | A | 8/1996 | Gross |
| 5,582,596 | A | 12/1996 | Fukunaga et al. |
| 5,583,114 | A | 12/1996 | Barrows et al. |
| 5,609,271 | A | 3/1997 | Keller et al. |
| 5,612,050 | A | 3/1997 | Rowe et al. |
| 5,636,643 | A | 6/1997 | Argenta et al. |
| 5,645,081 | A | 7/1997 | Argenta et al. |
| 5,660,823 | A | 8/1997 | Chakrabarti et al. |
| 5,707,499 | A | 1/1998 | Joshi et al. |
| 5,717,030 | A | 2/1998 | Dunn et al. |
| 5,747,064 | A | 5/1998 | Burnett et al. |
| 5,759,560 | A | 6/1998 | Dillon |
| 5,759,570 | A | 6/1998 | Arnold |
| 5,776,193 | A | 7/1998 | Kwan et al. |
| 5,834,007 | A | 11/1998 | Kubota |
| 5,840,777 | A | 11/1998 | Eagles et al. |
| 5,852,126 | A | 12/1998 | Barnard et al. |
| 5,874,500 | A | 2/1999 | Rhee et al. |
| D406,899 | S | 3/1999 | Cottle |
| RE36,235 | E | 6/1999 | Keller et al. |
| 5,944,703 | A | 8/1999 | Dixon et al. |
| 5,945,115 | A | 8/1999 | Dunn et al. |
| 5,962,010 | A | 10/1999 | Greff et al. |
| 5,998,472 | A | 12/1999 | Berger et al. |
| 6,022,904 | A * | 2/2000 | Sollradl ................... C08J 9/02 521/154 |
| 6,024,731 | A | 2/2000 | Seddon et al. |
| 6,065,270 | A | 5/2000 | Reinhard et al. |
| 6,071,267 | A | 6/2000 | Zamierowski |
| 6,121,341 | A * | 9/2000 | Sawhney ............ A61L 24/0015 522/84 |
| 6,135,116 | A | 10/2000 | Vogel et al. |
| D434,150 | S | 11/2000 | Tumey et al. |
| 6,142,982 | A | 11/2000 | Hunt et al. |
| 6,143,352 | A | 11/2000 | Clark et al. |
| 6,165,201 | A | 12/2000 | Sawhney et al. |
| 6,168,788 | B1 | 1/2001 | Wortham |
| D439,341 | S | 3/2001 | Tumey et al. |
| 6,214,332 | B1 | 4/2001 | Askill et al. |
| 6,252,129 | B1 | 6/2001 | Coffee |
| 6,261,276 | B1 | 7/2001 | Reitsma |
| 6,345,623 | B1 | 2/2002 | Heaton et al. |
| 6,391,294 | B1 | 5/2002 | Dettmar et al. |
| 6,398,761 | B1 | 6/2002 | Bills et al. |
| 6,447,802 | B2 | 9/2002 | Sessions et al. |
| 6,458,109 | B1 | 10/2002 | Henley et al. |
| 6,486,285 | B2 | 11/2002 | Fujita |
| 6,495,127 | B1 | 12/2002 | Wallace et al. |
| 6,509,031 | B1 | 1/2003 | Miller et al. |
| 6,521,251 | B2 | 2/2003 | Askill et al. |
| 6,527,203 | B2 | 3/2003 | Hurray et al. |
| 6,547,467 | B2 | 4/2003 | Quintero |
| 6,553,998 | B2 | 4/2003 | Heaton et al. |
| 6,564,972 | B2 | 5/2003 | Sawhney et al. |
| 6,569,113 | B2 | 5/2003 | Wirt et al. |
| 6,575,940 | B1 | 6/2003 | Levinson et al. |
| 6,596,704 | B1 | 7/2003 | Court et al. |
| 6,626,891 | B2 | 9/2003 | Ohmstede |
| 6,627,216 | B2 | 9/2003 | Brandt et al. |
| 6,629,774 | B1 | 10/2003 | Guruendeman |
| 6,648,852 | B2 * | 11/2003 | Wirt .................. A61B 17/00491 604/191 |
| 6,648,862 | B2 | 11/2003 | Watson |
| 6,685,681 | B2 | 2/2004 | Lockwood et al. |
| 6,695,823 | B1 | 2/2004 | Lina et al. |
| 6,698,622 | B2 | 3/2004 | Sawhney et al. |
| 6,730,299 | B1 | 5/2004 | Tayot et al. |
| 6,732,887 | B2 | 5/2004 | Bills |
| 6,746,428 | B2 | 6/2004 | Llorach et al. |
| 6,752,794 | B2 | 6/2004 | Lockwood et al. |
| 6,755,807 | B2 | 6/2004 | Risk et al. |
| 6,764,462 | B2 | 7/2004 | Risk, Jr. et al. |
| 6,767,334 | B1 | 7/2004 | Randolph |
| 6,776,769 | B2 | 8/2004 | Smith |
| 6,790,438 | B1 | 9/2004 | Constancis et al. |
| 6,800,074 | B2 | 10/2004 | Henley et al. |

(56) References Cited

U.S. PATENT DOCUMENTS

| | | |
|---|---|---|
| 6,814,079 B2 | 11/2004 | Heaton et al. |
| 6,820,766 B2 | 11/2004 | Keller et al. |
| 6,824,533 B2 | 11/2004 | Risk, Jr. et al. |
| 6,840,462 B2 | 1/2005 | Hurray et al. |
| 6,855,135 B2 | 2/2005 | Lockwood et al. |
| 6,856,821 B2 | 2/2005 | Johnson |
| 6,926,695 B2 | 8/2005 | Levinson et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,108,683 B2 | 9/2006 | Zamierowski |
| 7,117,869 B2 | 10/2006 | Heaton et al. |
| 7,128,735 B2 | 10/2006 | Weston |
| 7,129,210 B2 | 10/2006 | Lowinger et al. |
| 7,132,170 B2 | 11/2006 | Parker |
| 7,175,336 B2 | 2/2007 | Voellmicke et al. |
| 7,216,651 B2 | 5/2007 | Argenta et al. |
| 7,303,757 B2 | 12/2007 | Schankereli et al. |
| 7,316,330 B2 | 1/2008 | Muller et al. |
| 7,361,184 B2 | 4/2008 | Joshi |
| 7,381,859 B2 | 6/2008 | Hunt et al. |
| 7,387,432 B2 | 6/2008 | Lu et al. |
| 7,396,507 B2 | 7/2008 | Grunwald et al. |
| 7,524,315 B2 | 4/2009 | Blott et al. |
| 7,534,927 B2 | 5/2009 | Lockwood |
| 7,543,843 B2 | 6/2009 | Keshavaraj et al. |
| 7,569,742 B2 | 8/2009 | Haggstrom et al. |
| 7,605,298 B2 | 10/2009 | Bechert et al. |
| 7,611,500 B1 | 11/2009 | Lina et al. |
| 7,615,036 B2 | 11/2009 | Joshi et al. |
| 7,622,629 B2 | 11/2009 | Aail |
| 7,625,362 B2 | 12/2009 | Boehringer et al. |
| 7,635,343 B2 | 12/2009 | Mcintosh et al. |
| 7,674,837 B2 | 3/2010 | Gaserod et al. |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,708,940 B2 | 5/2010 | Grunwald et al. |
| 7,717,313 B2 | 5/2010 | Criscuolo et al. |
| 7,718,249 B2 | 5/2010 | Russell et al. |
| 7,722,582 B2 | 5/2010 | Lina et al. |
| 7,723,560 B2 | 5/2010 | Lockwood et al. |
| 7,749,531 B2 | 7/2010 | Booher |
| 7,758,554 B2 | 7/2010 | Lina et al. |
| 7,759,537 B2 | 7/2010 | Bishop et al. |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,862,831 B2 | 1/2011 | Wang et al. |
| 7,882,983 B2 | 2/2011 | Reidt et al. |
| 7,910,135 B2 | 3/2011 | St. John et al. |
| 7,910,791 B2 | 3/2011 | Coffey |
| 7,919,182 B2 | 4/2011 | Hamada et al. |
| 7,922,703 B2 | 4/2011 | Riesinger |
| 7,922,743 B2 | 4/2011 | Heinrich et al. |
| 7,927,318 B2 | 4/2011 | Risk, Jr. et al. |
| 7,954,672 B2 | 6/2011 | Keller |
| 7,959,624 B2 | 6/2011 | Riesinger |
| 7,964,766 B2 | 6/2011 | Blott et al. |
| 7,976,519 B2 | 7/2011 | Bubb et al. |
| 8,007,164 B2 | 8/2011 | Miyano et al. |
| 8,025,650 B2 | 9/2011 | Anderson et al. |
| 8,034,037 B2 | 10/2011 | Adams et al. |
| 8,062,272 B2 | 11/2011 | Weston |
| 8,062,331 B2 | 11/2011 | Zamierowski |
| 8,074,843 B2 | 12/2011 | Keller |
| 8,080,702 B2 | 12/2011 | Blott et al. |
| 8,096,979 B2 | 1/2012 | Lina et al. |
| 8,100,887 B2 | 1/2012 | Weston et al. |
| 8,118,794 B2 | 2/2012 | Weston et al. |
| 8,119,160 B2 | 2/2012 | Looney et al. |
| 8,152,785 B2 | 4/2012 | Vitaris |
| 8,162,907 B2 | 4/2012 | Heagle |
| 8,162,909 B2 | 4/2012 | Blott et al. |
| 8,168,848 B2 | 5/2012 | Lockwood et al. |
| 8,192,409 B2 | 6/2012 | Hardman et al. |
| 8,207,392 B2 | 6/2012 | Haggstrom et al. |
| 8,225,981 B2 | 7/2012 | Criscuolo et al. |
| 8,226,942 B2 | 7/2012 | Charier et al. |
| 8,235,972 B2 | 8/2012 | Adahan |
| 8,241,261 B2 | 8/2012 | Randolph et al. |
| 8,267,918 B2 | 9/2012 | Johnson et al. |
| 8,273,368 B2 | 9/2012 | Ambrosio et al. |
| 8,282,611 B2 | 10/2012 | Weston |
| 8,286,832 B2 | 10/2012 | Keller |
| 8,303,552 B2 | 11/2012 | Weston |
| 8,372,049 B2 | 2/2013 | Jaeb et al. |
| 8,372,050 B2 | 2/2013 | Jaeb et al. |
| 8,382,731 B2 | 2/2013 | Johannison |
| 8,410,189 B2 | 4/2013 | Carnahan et al. |
| 8,425,478 B2 | 4/2013 | Olson |
| 8,444,612 B2 | 5/2013 | Patel et al. |
| 8,444,613 B2 | 5/2013 | Svedman et al. |
| 8,454,580 B2 | 6/2013 | Locke et al. |
| 8,460,255 B2 | 6/2013 | Joshi et al. |
| 8,481,801 B2 | 7/2013 | Addison et al. |
| 8,535,296 B2 | 9/2013 | Blott et al. |
| 8,540,688 B2 | 9/2013 | Eckstein et al. |
| 8,540,699 B2 | 9/2013 | Miller et al. |
| 8,568,386 B2 | 10/2013 | Malhi |
| 8,613,734 B2 | 12/2013 | Lina et al. |
| 8,628,505 B2 | 1/2014 | Weston |
| 8,641,691 B2 | 2/2014 | Fink |
| 8,663,198 B2 | 3/2014 | Buan et al. |
| 8,708,998 B2 | 4/2014 | Weston et al. |
| 8,715,256 B2 | 5/2014 | Greener |
| 8,753,670 B2 | 6/2014 | Delmotte |
| 8,791,316 B2 | 7/2014 | Greener |
| 8,795,635 B2 | 8/2014 | Tamarkin et al. |
| 8,795,713 B2 | 8/2014 | Makower et al. |
| 8,801,685 B2 | 8/2014 | Armstrong et al. |
| 8,808,274 B2 | 8/2014 | Hartwell |
| 8,834,451 B2 | 9/2014 | Blott et al. |
| 8,843,327 B2 | 9/2014 | Vernon-Harcourt et al. |
| 8,894,620 B2 | 11/2014 | Swain |
| 8,916,742 B2 | 12/2014 | Smith |
| 8,968,773 B2 | 3/2015 | Thomas et al. |
| 8,998,866 B2 | 4/2015 | Hicks |
| 9,028,872 B2 | 5/2015 | Gaserod et al. |
| 9,067,003 B2 | 6/2015 | Buan et al. |
| 9,127,665 B2 | 9/2015 | Locke et al. |
| 9,173,777 B2 | 11/2015 | Zurovcik |
| 9,283,118 B2 | 3/2016 | Locke et al. |
| 9,302,033 B2 | 4/2016 | Riesinger |
| 9,375,353 B2 | 6/2016 | Vitaris et al. |
| 9,375,521 B2 | 6/2016 | Hudspeth et al. |
| 9,427,505 B2 | 8/2016 | Askem et al. |
| 9,474,661 B2 | 10/2016 | Fouillet et al. |
| 9,682,179 B2 | 6/2017 | May |
| 9,829,471 B2 | 11/2017 | Hammond et al. |
| 10,046,096 B2 | 8/2018 | Askem et al. |
| 10,070,994 B2 | 9/2018 | Dodd et al. |
| 2001/0004082 A1 | 6/2001 | Keller et al. |
| 2001/0043913 A1 | 11/2001 | Spaans et al. |
| 2002/0010299 A1* | 1/2002 | Guyuron ............. A61L 15/26 528/10 |
| 2002/0038826 A1 | 4/2002 | Hurray et al. |
| 2002/0122771 A1 | 9/2002 | Holland et al. |
| 2002/0143286 A1 | 10/2002 | Tumey |
| 2002/0145007 A1 | 10/2002 | Sawhney et al. |
| 2002/0146662 A1 | 10/2002 | Radl et al. |
| 2002/0183702 A1 | 12/2002 | Henley et al. |
| 2002/0187182 A1 | 12/2002 | Kramer et al. |
| 2002/0198490 A1 | 12/2002 | Wirt et al. |
| 2003/0040478 A1 | 2/2003 | Drucker et al. |
| 2003/0069535 A1 | 4/2003 | Shalaby |

(56) References Cited

U.S. PATENT DOCUMENTS

| | | |
|---|---|---|
| 2003/0069563 A1 | 4/2003 | Johnson |
| 2003/0093041 A1 | 5/2003 | Risk, Jr. et al. |
| 2003/0125646 A1 | 7/2003 | Whitlock |
| 2003/0143189 A1 | 7/2003 | Askill et al. |
| 2003/0183653 A1 | 10/2003 | Bills |
| 2003/0212357 A1 | 11/2003 | Pace |
| 2004/0006319 A1 | 1/2004 | Lina et al. |
| 2004/0033466 A1 | 2/2004 | Shellard et al. |
| 2004/0037897 A1 | 2/2004 | Benjamin et al. |
| 2004/0049187 A1 | 3/2004 | Burnett et al. |
| 2004/0057855 A1 | 3/2004 | Gerlach et al. |
| 2004/0073152 A1 | 4/2004 | Karason et al. |
| 2004/0084812 A1 | 5/2004 | Grunwald et al. |
| 2004/0121438 A1 | 6/2004 | Quirk |
| 2004/0167617 A1 | 8/2004 | Voellmicke et al. |
| 2004/0171998 A1 | 9/2004 | Marasco, Jr. |
| 2005/0020955 A1 | 1/2005 | Sanders et al. |
| 2005/0085795 A1 | 4/2005 | Lockwood |
| 2005/0100692 A1 | 5/2005 | Parker |
| 2005/0137272 A1 | 6/2005 | Gaserod et al. |
| 2005/0163904 A1 | 7/2005 | Walker et al. |
| 2005/0230422 A1 | 10/2005 | Muller et al. |
| 2006/0009577 A1 | 1/2006 | Hara |
| 2006/0009744 A1 | 1/2006 | Erdman et al. |
| 2006/0079599 A1 | 4/2006 | Arthur |
| 2006/0100586 A1 | 5/2006 | Karpowicz |
| 2006/0173253 A1 | 8/2006 | Ganapathy et al. |
| 2006/0173514 A1 | 8/2006 | Biel et al. |
| 2006/0217016 A1 | 9/2006 | Lin et al. |
| 2006/0228318 A1 | 10/2006 | Fabo |
| 2006/0253082 A1 | 11/2006 | Mcintosh et al. |
| 2006/0273109 A1 | 12/2006 | Keller |
| 2007/0004896 A1 | 1/2007 | Ito et al. |
| 2007/0009580 A1 | 1/2007 | DiCosmo et al. |
| 2007/0040454 A1 | 2/2007 | Freudenberger et al. |
| 2007/0055209 A1 | 3/2007 | Patel et al. |
| 2007/0141101 A1 | 6/2007 | Nugent et al. |
| 2007/0147947 A1 | 6/2007 | Stenton et al. |
| 2007/0164047 A1 | 7/2007 | Reidt et al. |
| 2007/0185463 A1 | 8/2007 | Mulligan |
| 2007/0186404 A1 | 8/2007 | Drew et al. |
| 2007/0203062 A1 | 8/2007 | Ellis-Behnke et al. |
| 2007/0219513 A1 | 9/2007 | Lina et al. |
| 2007/0225663 A1 | 9/2007 | Watt et al. |
| 2007/0237811 A1 | 10/2007 | Scherr |
| 2007/0248642 A1 | 10/2007 | Dornish et al. |
| 2008/0004549 A1 | 1/2008 | Anderson et al. |
| 2008/0031748 A1 | 2/2008 | Ihle et al. |
| 2008/0060550 A1 | 3/2008 | MacDonald et al. |
| 2008/0089173 A1 | 4/2008 | Lu et al. |
| 2008/0132821 A1 | 6/2008 | Propp et al. |
| 2008/0206155 A1 | 8/2008 | Tamarkin et al. |
| 2008/0208163 A1 | 8/2008 | Wilkie |
| 2008/0232187 A1 | 9/2008 | Miyano et al. |
| 2008/0249259 A1 | 10/2008 | Kashiwagi |
| 2008/0254103 A1 | 10/2008 | Harris et al. |
| 2008/0279807 A1 | 11/2008 | Belcheva et al. |
| 2008/0287880 A1 | 11/2008 | Keller |
| 2008/0306456 A1 | 12/2008 | Riesinger |
| 2008/0314929 A1 | 12/2008 | Keller |
| 2009/0020561 A1 | 1/2009 | Keller |
| 2009/0022779 A1 | 1/2009 | Kelly et al. |
| 2009/0030086 A1 | 1/2009 | Eady et al. |
| 2009/0093550 A1 | 4/2009 | Rolfes et al. |
| 2009/0098073 A1 | 4/2009 | MacDonald et al. |
| 2009/0098503 A1 | 4/2009 | Knispel et al. |
| 2009/0125004 A1 | 5/2009 | Shen et al. |
| 2009/0134186 A1 | 5/2009 | Keller |
| 2009/0157017 A1 | 6/2009 | Ambrosio |
| 2009/0157024 A1 | 6/2009 | Song |
| 2009/0196844 A1 | 8/2009 | Choi et al. |
| 2009/0227969 A1 | 9/2009 | Jaeb et al. |
| 2009/0234306 A1 | 9/2009 | Vitaris |
| 2009/0234309 A1 | 9/2009 | Vitaris et al. |
| 2009/0240185 A1 | 9/2009 | Jaeb et al. |
| 2009/0254053 A1 | 10/2009 | Svensby et al. |
| 2009/0275872 A1 | 11/2009 | Addison et al. |
| 2009/0299251 A1 | 12/2009 | Buan |
| 2009/0299255 A1 | 12/2009 | Kazala, Jr. et al. |
| 2009/0299306 A1 | 12/2009 | Buan |
| 2010/0012210 A1 | 1/2010 | Miyano et al. |
| 2010/0022972 A1 | 1/2010 | Lina et al. |
| 2010/0030132 A1 | 2/2010 | Niezgoda et al. |
| 2010/0036305 A1 | 2/2010 | Green |
| 2010/0036334 A1 | 2/2010 | Heagle et al. |
| 2010/0069850 A1 | 3/2010 | Fabo |
| 2010/0125258 A1 | 5/2010 | Coulthard et al. |
| 2010/0125259 A1 | 5/2010 | Olson |
| 2010/0135915 A1 | 6/2010 | Greener et al. |
| 2010/0137775 A1* | 6/2010 | Hu ................ A61M 1/0088 602/54 |
| 2010/0160880 A1 | 6/2010 | Weston |
| 2010/0230467 A1 | 9/2010 | Crisuolo et al. |
| 2010/0259406 A1 | 10/2010 | Caso et al. |
| 2010/0268177 A1 | 10/2010 | Hall |
| 2010/0268198 A1 | 10/2010 | Buan et al. |
| 2010/0305526 A1 | 12/2010 | Robinson et al. |
| 2010/0318052 A1 | 12/2010 | Ha et al. |
| 2010/0324510 A1 | 12/2010 | Andresen et al. |
| 2011/0004172 A1 | 1/2011 | Eckstein et al. |
| 2011/0021431 A1 | 1/2011 | Jones et al. |
| 2011/0028918 A1 | 2/2011 | Hartwell |
| 2011/0028919 A1 | 2/2011 | Johnnison et al. |
| 2011/0033503 A1 | 2/2011 | Sinko et al. |
| 2011/0036889 A1 | 2/2011 | Heinrich et al. |
| 2011/0066123 A1 | 3/2011 | Tout et al. |
| 2011/0086077 A1 | 4/2011 | McCrea et al. |
| 2011/0118683 A1 | 5/2011 | Weston |
| 2011/0144599 A1 | 6/2011 | Croizat et al. |
| 2011/0147432 A1 | 6/2011 | Heinrich et al. |
| 2011/0147435 A1 | 6/2011 | Heinrich et al. |
| 2011/0224631 A1 | 9/2011 | Simmons |
| 2011/0250447 A1 | 10/2011 | Taniguchi et al. |
| 2011/0257611 A1 | 10/2011 | Locke et al. |
| 2011/0282309 A1* | 11/2011 | Adie ................ A61M 1/0088 604/319 |
| 2011/0313374 A1 | 12/2011 | Lockwood et al. |
| 2011/0319804 A1 | 12/2011 | Greener |
| 2012/0041399 A1 | 2/2012 | Blott et al. |
| 2012/0051945 A1 | 3/2012 | Orndorff et al. |
| 2012/0083755 A1 | 4/2012 | Lina et al. |
| 2012/0095380 A1 | 4/2012 | Gergley et al. |
| 2012/0116334 A1 | 5/2012 | Albert et al. |
| 2012/0123356 A1 | 5/2012 | Greener |
| 2012/0123358 A1 | 5/2012 | Hall et al. |
| 2012/0222687 A1 | 9/2012 | Czajka, Jr. et al. |
| 2013/0023841 A1 | 1/2013 | Johnson et al. |
| 2013/0066285 A1 | 3/2013 | Locke et al. |
| 2013/0066289 A1 | 3/2013 | Song et al. |
| 2013/0090616 A1 | 4/2013 | Neubauer |
| 2013/0096519 A1 | 4/2013 | Blott et al. |
| 2013/0116635 A1 | 5/2013 | Fleischmann |
| 2013/0138054 A1 | 5/2013 | Fleischmann |
| 2013/0138060 A1 | 5/2013 | Haqqstrom et al. |
| 2013/0144227 A1 | 6/2013 | Locke et al. |
| 2013/0144230 A1 | 6/2013 | Wu et al. |
| 2013/0150814 A1 | 6/2013 | Buan |
| 2013/0165878 A1 | 6/2013 | Heagle |
| 2013/0245583 A1 | 9/2013 | Locke et al. |
| 2013/0274688 A1 | 10/2013 | Weston |
| 2013/0296762 A1 | 11/2013 | Toth |
| 2013/0302545 A1 | 11/2013 | Schnelker et al. |
| 2013/0310780 A1* | 11/2013 | Phillips ............ A61L 15/26 604/319 |
| 2013/0310781 A1 | 11/2013 | Phillips et al. |
| 2013/0331822 A1 | 12/2013 | Patel et al. |
| 2013/0338613 A1 | 12/2013 | Haggstrom et al. |
| 2014/0012214 A1 | 1/2014 | Miller et al. |
| 2014/0114268 A1 | 4/2014 | Auguste et al. |
| 2014/0171888 A1* | 6/2014 | Croizat ............ A61F 13/0236 604/319 |
| 2014/0200533 A1 | 7/2014 | Whyte et al. |
| 2014/0228791 A1 | 8/2014 | Hartwell |
| 2014/0228792 A1 | 8/2014 | Weston et al. |

(56) References Cited

U.S. PATENT DOCUMENTS

| | | |
|---|---|---|
| 2014/0249493 A1 | 9/2014 | Hartwell |
| 2014/0316359 A1 | 10/2014 | Collinson et al. |
| 2015/0032035 A1 | 1/2015 | Banwell et al. |
| 2015/0119831 A1 | 4/2015 | Robinson et al. |
| 2015/0119832 A1 | 4/2015 | Locke |
| 2015/0119833 A1 | 4/2015 | Coulthard et al. |
| 2015/0159066 A1 | 6/2015 | Hartwell et al. |
| 2015/0174304 A1* | 6/2015 | Askem ............... A61M 1/0088 604/319 |
| 2015/0190286 A1 | 7/2015 | Allen et al. |
| 2015/0216733 A1 | 8/2015 | Allen et al. |
| 2015/0306273 A1 | 10/2015 | Karim et al. |
| 2016/0000610 A1 | 1/2016 | Riesinger |
| 2016/0000611 A1 | 1/2016 | Niederauer et al. |
| 2016/0120706 A1 | 5/2016 | Collinson et al. |
| 2016/0136339 A1 | 5/2016 | Begin et al. |
| 2016/0144084 A1 | 5/2016 | Collinson et al. |
| 2016/0262942 A1 | 9/2016 | Riesinger |
| 2016/0298620 A1 | 10/2016 | Cordoba et al. |

FOREIGN PATENT DOCUMENTS

| | | |
|---|---|---|
| DE | 20 2004 017 052 | 7/2005 |
| EP | 0 251 810 | 1/1988 |
| EP | 0340018 A2 | 11/1989 |
| EP | 0 358 302 | 3/1990 |
| EP | 0 425 164 | 5/1991 |
| EP | 0 322 118 | 6/1992 |
| EP | 0 521 434 | 1/1993 |
| EP | 0 325 771 | 9/1993 |
| EP | 0 578 999 | 1/1994 |
| EP | 0 617 152 | 9/1994 |
| EP | 0 549 781 | 9/1996 |
| EP | 0 762 860 | 3/1997 |
| EP | 0 506 241 | 5/1997 |
| EP | 0 793 019 | 9/1997 |
| EP | 0 620 720 | 3/1998 |
| EP | 0 858 810 | 8/1998 |
| EP | 0 651 983 | 9/1998 |
| EP | 0 888 141 | 1/1999 |
| EP | 0 912 251 | 5/1999 |
| EP | 0 923 905 | 6/1999 |
| EP | 1 007 015 | 6/2000 |
| EP | 1 013 290 | 6/2000 |
| EP | 1 029 585 | 8/2000 |
| EP | 0 688 189 | 9/2000 |
| EP | 1 088 569 | 4/2001 |
| EP | 1 105 171 | 6/2001 |
| EP | 1 105 180 | 6/2001 |
| EP | 1 107 813 | 6/2001 |
| EP | 1 114 933 | 7/2001 |
| EP | 1 030 657 | 10/2001 |
| EP | 1 139 951 | 10/2001 |
| EP | 0 921 775 | 12/2001 |
| EP | 1 177 781 | 2/2002 |
| EP | 1 283 702 | 2/2003 |
| EP | 1 306 123 | 5/2003 |
| EP | 1 440 737 | 7/2004 |
| EP | 1 018 967 | 8/2004 |
| EP | 1 633 830 | 3/2006 |
| EP | 1 637 088 | 3/2006 |
| EP | 1 171 065 | 3/2007 |
| EP | 1 798 835 | 6/2007 |
| EP | 1 476 217 | 3/2008 |
| EP | 1 955 887 | 8/2008 |
| EP | 1 978 046 | 10/2008 |
| EP | 1 988 125 | 11/2008 |
| EP | 2 111 804 | 10/2009 |
| EP | 2 127 690 | 12/2009 |
| EP | 2 263 627 | 12/2010 |
| EP | 2 335 747 | 6/2011 |
| EP | 2 366 721 | 9/2011 |
| EP | 2 462 908 | 6/2012 |
| EP | 2 529 767 | 12/2012 |
| EP | 2 477 674 | 7/2013 |
| EP | 2 544 642 | 1/2015 |
| EP | 2 648 668 | 1/2015 |
| FR | 1 163 907 | 10/1958 |
| GB | 1255395 A | 12/1971 |
| GB | 2288734 | 11/1995 |
| GB | 2306580 | 5/1997 |
| GB | 2329127 | 3/1999 |
| GB | 2305610 | 7/1999 |
| GB | 2389794 | 12/2003 |
| GB | 2423019 | 8/2006 |
| GB | 2424582 | 10/2006 |
| GB | 2435419 | 2/2007 |
| GB | 2435422 | 8/2007 |
| GB | 2468905 A | 9/2010 |
| JP | S59-36608 | 2/1984 |
| JP | H05-070692 | 3/1993 |
| JP | 2005-261376 | 9/2005 |
| JP | 2005-334188 | 12/2005 |
| JP | 2009148393 A | 7/2009 |
| WO | WO-8300742 A1 | 3/1983 |
| WO | WO 1992/009301 | 6/1992 |
| WO | WO 1992/09651 | 6/1992 |
| WO | WO 1992/010983 | 7/1992 |
| WO | WO-9216245 A1 | 10/1992 |
| WO | WO 1993/06802 | 4/1993 |
| WO | WO 1993/09176 | 5/1993 |
| WO | WO 1993/009727 | 5/1993 |
| WO | WO 1994/020133 | 9/1994 |
| WO | WO 1994/021207 | 9/1994 |
| WO | WO 1995/004511 | 2/1995 |
| WO | WO 1995/029959 | 11/1995 |
| WO | WO 1996/001731 | 1/1996 |
| WO | WO 1996/005873 | 2/1996 |
| WO | WO 1996/40174 | 12/1996 |
| WO | WO 1997/03717 | 2/1997 |
| WO | WO 1997/11658 | 4/1997 |
| WO | WO 1997/14384 | 4/1997 |
| WO | WO 1997/33922 | 9/1997 |
| WO | WO 1997/038732 | 10/1997 |
| WO | WO 1997/42986 | 11/1997 |
| WO | WO 1997/043991 | 11/1997 |
| WO | WO 1998/06444 | 2/1998 |
| WO | WO 1998/013000 | 4/1998 |
| WO | WO 1999/17698 | 4/1999 |
| WO | WO 1999/019013 | 4/1999 |
| WO | WO 1999/30629 | 6/1999 |
| WO | WO 1999/39671 | 8/1999 |
| WO | WO 1999/047097 | 9/1999 |
| WO | WO 1999/048621 | 9/1999 |
| WO | WO 1999/65536 | 12/1999 |
| WO | WO 2000/00016 | 1/2000 |
| WO | WO 2000/017968 | 3/2000 |
| WO | WO 2000/38752 | 7/2000 |
| WO | WO 2000/040190 | 7/2000 |
| WO | WO 2000/061206 | 10/2000 |
| WO | WO 2000/62827 | 10/2000 |
| WO | WO 2000/064396 | 11/2000 |
| WO | WO 2000/074738 | 12/2000 |
| WO | WO 2001/010363 | 2/2001 |
| WO | WO 2001/037773 | 5/2001 |
| WO | WO 2001/049233 | 7/2001 |
| WO | WO 2001/062312 | 8/2001 |
| WO | WO 2001/066017 | 9/2001 |
| WO | WO 2001/072251 | 10/2001 |
| WO | WO 2001/087271 | 11/2001 |
| WO | WO 2001/089588 | 11/2001 |
| WO | WO 2002/02079 | 1/2002 |
| WO | WO 2002/005737 | 1/2002 |
| WO | WO 2002/17840 | 3/2002 |
| WO | WO 2002/024132 | 3/2002 |
| WO | WO 2002/038096 | 5/2002 |
| WO | WO 2002/070040 | 9/2002 |
| WO | WO 2002/094256 | 11/2002 |
| WO | WO 2002/102864 | 12/2002 |
| WO | WO 2003/005943 | 1/2003 |
| WO | WO 2003/022333 | 3/2003 |
| WO | WO 2003/041786 | 5/2003 |
| WO | WO 2003/065877 | 8/2003 |

(56) References Cited

FOREIGN PATENT DOCUMENTS

| | | |
|---|---|---|
| WO | WO 2003/072748 | 9/2003 |
| WO | WO 2004/016313 | 2/2004 |
| WO | WO 2004/037334 | 5/2004 |
| WO | WO-2004052982 A2 | 6/2004 |
| WO | WO 2004/054632 | 7/2004 |
| WO | WO 2004/060148 | 7/2004 |
| WO | WO 2004/077387 | 9/2004 |
| WO | WO 2004/098474 | 11/2004 |
| WO | WO 2004/108175 | 12/2004 |
| WO | WO 2005/009488 | 2/2005 |
| WO | WO 2005/017000 | 2/2005 |
| WO | WO 2005/018695 | 3/2005 |
| WO | WO 2005/019343 | 3/2005 |
| WO | WO 2005/025447 | 3/2005 |
| WO | WO 2005/046760 | 5/2005 |
| WO | WO 2005/082435 | 9/2005 |
| WO | WO-2005105180 A1 | 11/2005 |
| WO | WO 2005/118011 | 12/2005 |
| WO | WO 2005/123170 | 12/2005 |
| WO | WO 2006/005939 | 1/2006 |
| WO | WO 2006/014534 | 2/2006 |
| WO | WO 2006/028244 | 3/2006 |
| WO | WO 2006/030054 | 3/2006 |
| WO | WO 2006/034128 | 3/2006 |
| WO | WO 2006/034166 | 3/2006 |
| WO | WO 2006/046060 | 5/2006 |
| WO | WO 2006/052839 | 5/2006 |
| WO | WO 2006/081403 | 8/2006 |
| WO | WO 2006/114637 | 11/2006 |
| WO | WO 2006/116992 | 11/2006 |
| WO | WO 2006/135506 | 12/2006 |
| WO | WO 2006/135934 | 12/2006 |
| WO | WO 2007/031757 | 3/2007 |
| WO | WO 2007/031762 | 3/2007 |
| WO | WO 2007/092397 | 8/2007 |
| WO | WO 2007/095180 | 8/2007 |
| WO | WO 2007/106590 | 9/2007 |
| WO | WO 2007/106594 | 9/2007 |
| WO | WO 2007/116347 | 10/2007 |
| WO | WO-2007113597 A2 | 10/2007 |
| WO | WO 2007/123451 | 11/2007 |
| WO | WO 2007/124198 | 11/2007 |
| WO | WO 2007/133618 | 11/2007 |
| WO | WO 2007/143060 | 12/2007 |
| WO | WO 2008/008032 | 1/2008 |
| WO | WO-2008008032 A1 * | 1/2008 ......... A61F 13/0203 |
| WO | WO 2008/036162 | 3/2008 |
| WO | WO-2008028494 A2 | 3/2008 |
| WO | WO 2008/039223 | 4/2008 |
| WO | WO 2008/040681 | 4/2008 |
| WO | WO 2008/043067 | 4/2008 |
| WO | WO 2008/060475 | 5/2008 |
| WO | WO 2008/076407 | 6/2008 |
| WO | WO 2008/082444 | 7/2008 |
| WO | WO 2008/086397 | 7/2008 |
| WO | WO 2008/100437 | 8/2008 |
| WO | WO 2008/104609 | 9/2008 |
| WO | WO 2008/134544 | 11/2008 |
| WO | WO 2008/134774 | 11/2008 |
| WO | WO 2008/135997 | 11/2008 |
| WO | WO 2009/011856 | 1/2009 |
| WO | WO 2009/042514 | 4/2009 |
| WO | WO 2009/047524 | 4/2009 |
| WO | WO 2009/052193 | 4/2009 |
| WO | WO 2009/060327 | 5/2009 |
| WO | WO 2009/062327 | 5/2009 |
| WO | WO 2009/077722 | 6/2009 |
| WO | WO 2009/086580 | 7/2009 |
| WO | WO 2009/088925 | 7/2009 |
| WO | WO-2009090074 A1 | 7/2009 |
| WO | WO 2009/102021 | 8/2009 |
| WO | WO 2009/103031 | 8/2009 |
| WO | WO 2009/122989 | 10/2009 |
| WO | WO 2009/124100 | 10/2009 |
| WO | WO 2009/124407 | 10/2009 |
| WO | WO 2009/126102 | 10/2009 |
| WO | WO 2009/146441 | 12/2009 |
| WO | WO 2009/156709 | 12/2009 |
| WO | WO 2009/158128 | 12/2009 |
| WO | WO-2009147402 A2 | 12/2009 |
| WO | WO 2010/006182 | 1/2010 |
| WO | WO 2010/19997 | 1/2010 |
| WO | WO 2010/122665 | 10/2010 |
| WO | WO-2010121033 A2 | 10/2010 |
| WO | WO 2010/142959 | 12/2010 |
| WO | WO 2010/147533 | 12/2010 |
| WO | WO 2011/072840 | 6/2011 |
| WO | WO 2011/112870 | 9/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO-2011135284 A1 | 11/2011 |
| WO | WO 2012/009370 | 1/2012 |
| WO | WO-2012021553 A1 | 2/2012 |
| WO | WO 2012/041296 | 4/2012 |
| WO | WO 2012/069793 | 5/2012 |
| WO | WO 2012/069794 | 5/2012 |
| WO | WO 2012/074512 | 6/2012 |
| WO | WO 2012/078707 | 6/2012 |
| WO | WO 2012/131237 | 10/2012 |
| WO | WO 2012/140378 | 10/2012 |
| WO | WO 2012/143665 | 10/2012 |
| WO | WO 2013/010907 | 1/2013 |
| WO | WO 2013/029652 | 3/2013 |
| WO | WO-2013033131 A1 | 3/2013 |
| WO | WO 2013/064852 | 5/2013 |
| WO | WO 2013/076450 | 5/2013 |
| WO | WO 2013/083800 | 6/2013 |
| WO | WO 2013/090810 | 6/2013 |
| WO | WO 2013/110008 | 7/2013 |
| WO | WO 2013/136181 | 9/2013 |
| WO | WO 2013/149078 | 10/2013 |
| WO | WO 2014/008348 | 1/2014 |
| WO | WO 2014/020440 | 2/2014 |
| WO | WO 2014/020443 | 2/2014 |
| WO | WO 2014/113253 | 7/2014 |
| WO | WO-2015022340 A1 | 2/2015 |

OTHER PUBLICATIONS

"Technology Watch", May 1989, in 1 page.
Dethier, P. et al., "X-ray Sterilisation," The Technology of the Future, dated Feb. 1, 2010, in 3 pages. Retrieved from http://www.emdt.co.uk/article/x-ray-sterilisation-technology-future.
Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.
International Search Report and Written Opinion, re PCT Application No. PCT/GB2012/000866, dated Feb. 28, 2013.
International Search Report and Written Opinion, re PCT Application No. PCT/GB2014/050781, dated Jun. 13, 2014.
International Search Report and Written Opinion, re PCT Application No. PCT/GB2014/050786, dated Jun. 12, 2014.
International Preliminary Report on Patentability, re PCT Application No. PCT/GB2014/050786, dated Sep. 24, 2015.
International Search Report, re PCT Application No. PCT/GB2011/001649, dated Mar. 6, 2012.
International Search Report, re PCT Application No. PCT/GB2011/001652, dated May 18, 2012.
Jahns, B. et al., Poster "Problemwundversorgung mit einem neuen anschmiegsamen Silikonschaumverband mit Anwendung der Vakuumtechnik," 2nd Congress of German Wound Treatment Society 1998.
Kendall ULTEC Hydrocolloid Dressing (4"x4"), product ordering page, web page downloaded Jul. 13, 2014, in 1 page.
Khan, T. et al., "Influence of Chitosan Molecular Weight on its Physical Properties", IMJM (2003), vol. 2(1), pp. 1-8, in 8 pages.

(56) References Cited

OTHER PUBLICATIONS

Meissner, J., "X-ray Sterilisation," dated Mar. 1, 2008, in 3 pages. Retrieved from http://www.emdt.co.uk/article/x-ray-sterilisation.
Product Data Sheet, WACKER SilGel 612 A/B. Jun. 2014, in 3 pages.
Protz, K., "Moderne Wundauflagen unterstutzen Heilungsprozess", Wundversorgung: Indikation und Anwendung, Geriatrie Journal, Apr. 2005, pp. 3333-3339, with translation, in 17 pages.
He Sihuang, Beijeing: Quality Management in Drug Production, China Medical Science Press, p. 65-66, Feb. 28, 2009).
Sogias, I. et al., "Exploring the Factors Affecting the Solubility of Chitosan in Water", Macromol. Chem. Phys., 2010, vol. 211, pp. 426-433, in 8 pages.
Wacker SILPURAN 2445 data sheet, dated Oct. 11, 2014, in 3 pages.
Wooding-Scott, M. et al., "No Wound is Too Big for Resourceful Nurses," RN, Dec. 1988, pp. 22-25, USA, in 4 pages.
Advantec MFS, Inc., "Membrane Filters" (catalog), retrieved from http://www.advantecmfs.com/catalog/filt/membrane.pdf, on Jan. 29, 2016, Copyright 2001-2011, 17 pages.
International Preliminary Report on Patentability for Application No. PCT/GB2011/001649, dated Jun. 6, 2013.
International Preliminary Report on Patentability for Application No. PCT/GB2011/001652, dated Mar. 18, 2013, 23 pages.
International Preliminary Report on Patentability for Application No. PCT/GB2012/000866, dated Jun. 5, 2014, 8 pages.
Smith & Nephew, "PICO Single Use Negative Pressure Wound Therapy System," Spiral Booklet, Mar. 2011, 7 pages.
Letter/Objections from Dr. Tanja Bendele, LLM at RUHR for the European Patent No. 2643412, mailed on Apr. 1, 2015, 8 pages.
Letter/Observations from Dr. Tanja Bendele, LLM at Ruhr EP2643027, dated May 29, 2015, 10 pages.
Letter/Opposition from Dr. Tanja Bendele, LLM at RUHR for the European Patent No. 2643027, mailed on May 21, 2014, 17 pages.
Puleo J.R., et al., "Heat Sterilization of Activated Carbon," Biotechnology and Bioengineering, 1966, vol. VIII, No. 4, pp. 631-632.

\* cited by examiner

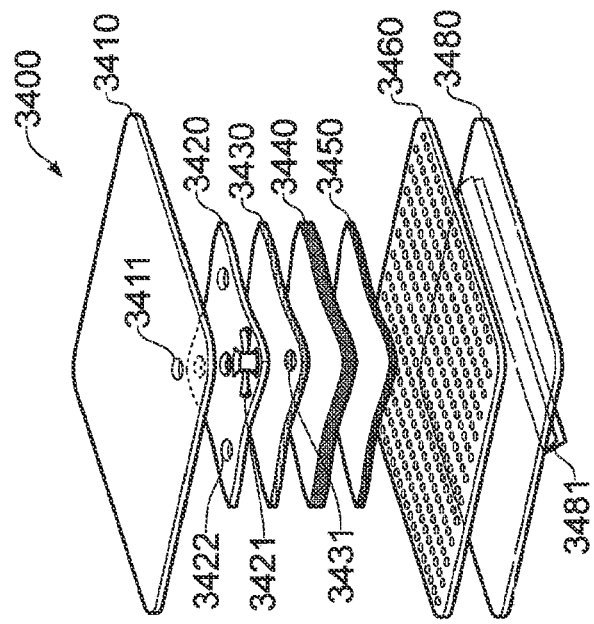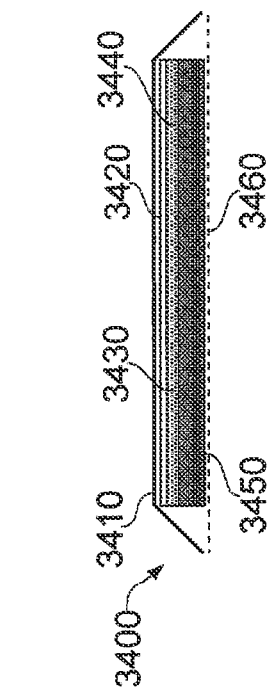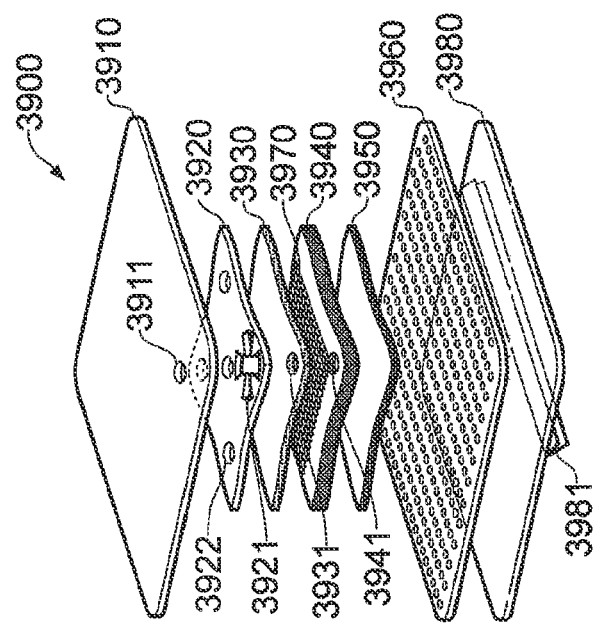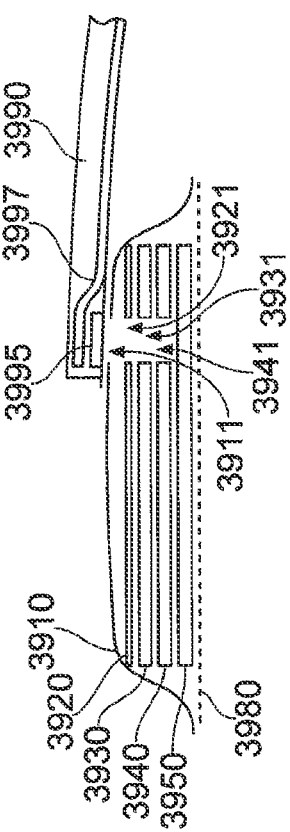

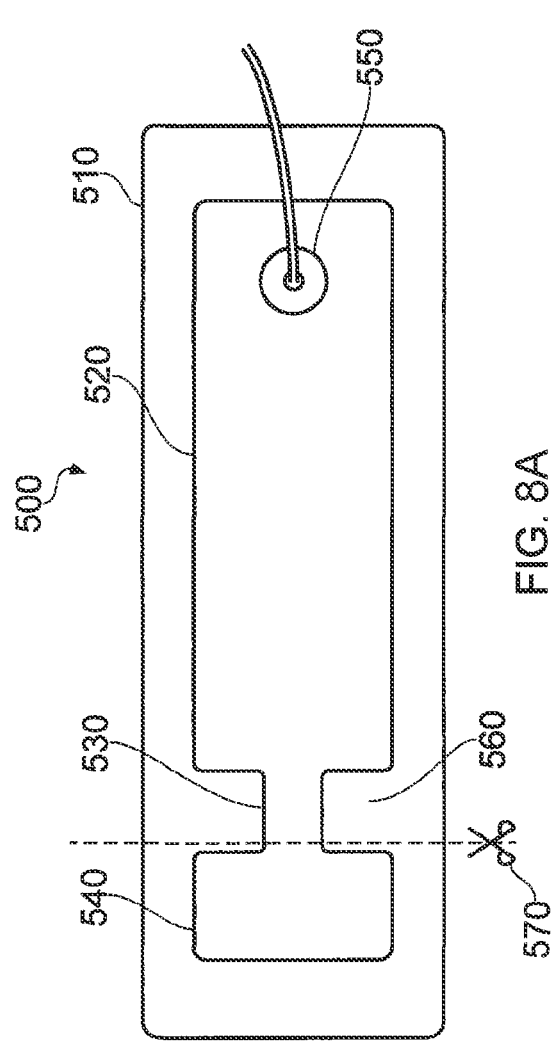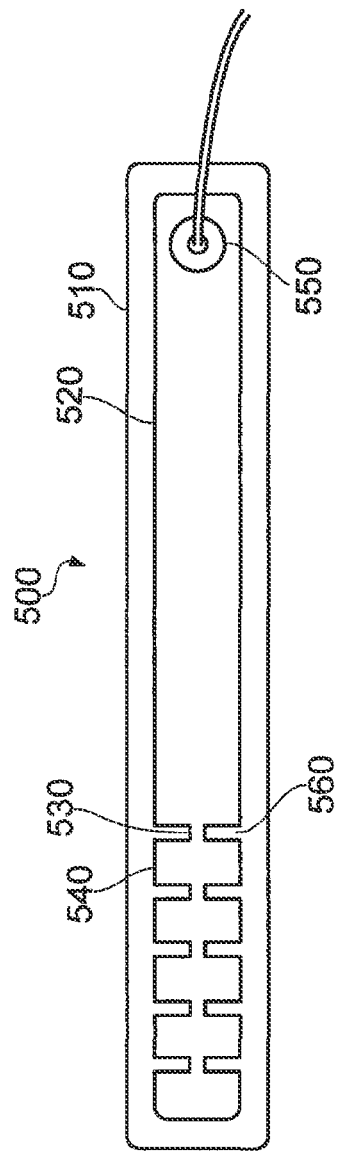

 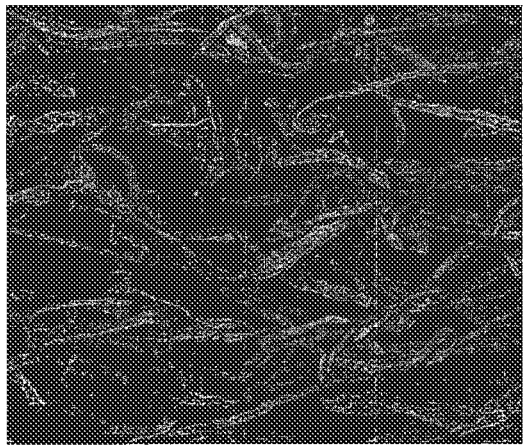
FIG. 13A         FIG. 13B
FIG. 13C
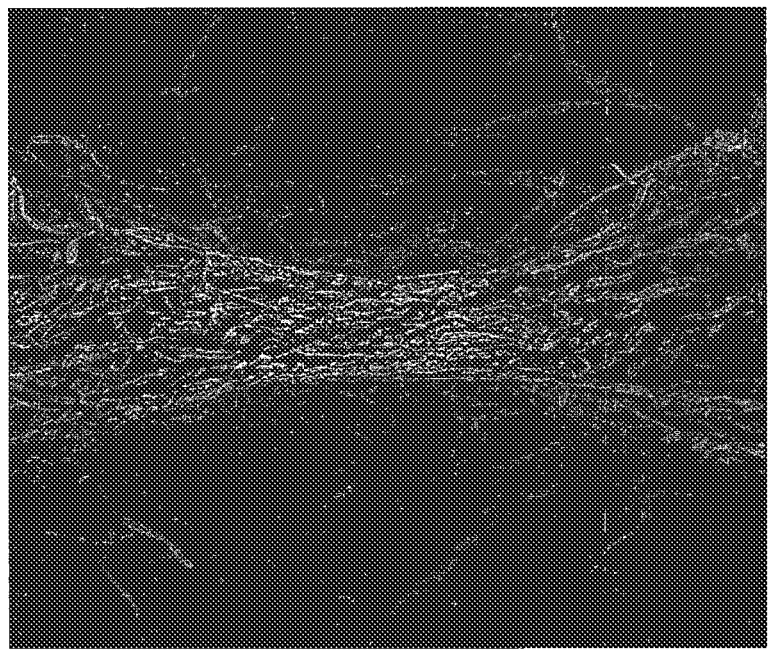
FIG. 13D

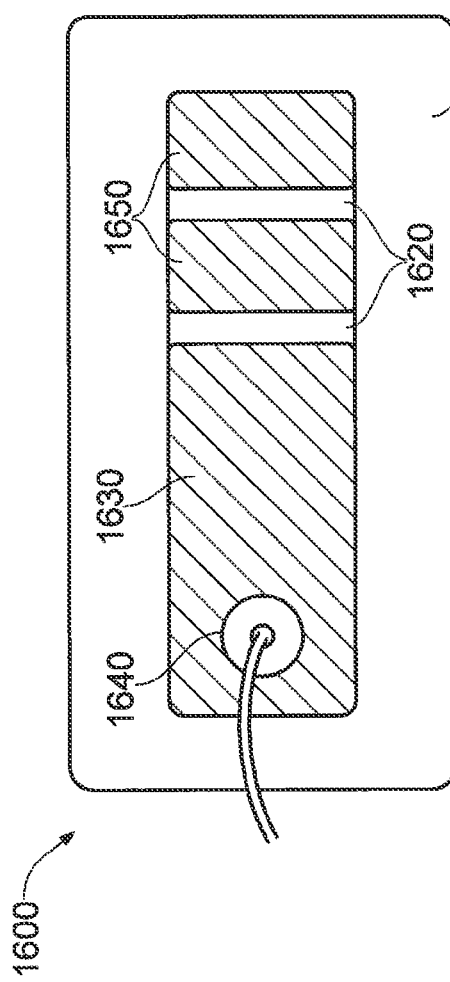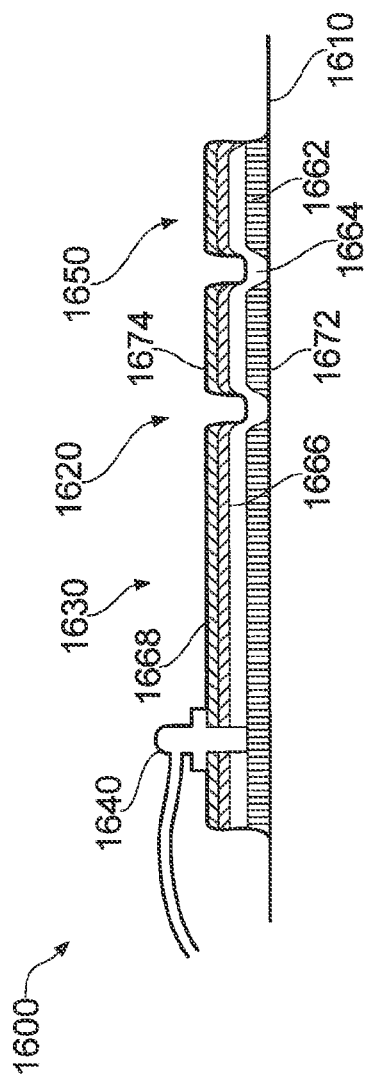

WOUND DRESSING SEALANT AND USE THEREOF

This application is a divisional application of U.S. application Ser. No. 14/776,088, filed on Sep. 14, 2015, which is a national stage application of International Patent Application No. PCT/GB2014/050786, filed on Mar. 14, 2014, which claims priority to U.S. Provisional Application Ser. No. 61/800,040, filed Mar. 15, 2013, titled "WOUND DRESSING AND METHOD OF TREATMENT," U.S. Provisional Application Ser. No. 61/828,604, filed May 29, 2013, titled "WOUND DRESSING AND METHOD OF TREATMENT," U.S. Provisional Application Ser. No. 61/829,187, filed May 30, 2013, titled "WOUND DRESSING AND METHOD OF TREATMENT," G.B. Provisional Application No. 1309662.3, filed May 30, 2013, G.B. Provisional Application No. 1309709.2, filed May 30, 2013, U.S. Provisional Application Ser. No. 61/906,865, filed Nov. 20, 2013, titled "WOUND DRESSING AND METHOD OF TREATMENT," and U.S. Provisional Application No. 61/907,350, filed Nov. 21, 2013, entitled "WOUND DRESSING AND METHOD OF TREATMENT."

Embodiments described herein relate to compositions, devices incorporating the same, apparatuses, kits, their uses in wound care, and methods for the treatment of wounds and for creating a main wound dressing portion for use in wound dressing, for example in advanced wound management, particularly, but not exclusively, in negative pressure therapy (TNP therapy).

Different types of wound dressing exist for aiding in the healing process of a human or animal subject in need thereof. These include different types of materials, for example, gauze and/or foam with overlying drapes, and composites thereof, provided in assembled layers and in a selection of sizes or shapes, typically square or rectangular shapes. Advanced wound management dressings address specific wound therapies by means of tailored dressing components, particularly, but not exclusively, TNP therapy dressings incorporate a means for transmitting negative pressure to the wound, and a fluid-tight drape for enclosing a negative pressure, provided as independent components or as a composite dressing.

We have found, as a first problem, that certain wounds and body topography cannot be adequately dressed using the existing selection of composite TNP dressings, for example vein harvest wounds extending the length of a subject's leg exceed available dressing dimensions or diabetic foot ulcers where complex topography prevents rectangular designs from conforming adequately to tight body contours.

We have found, as a further problem, that advanced wound therapy and in particular TNP therapy, cannot therefore be applied to those wounds which perhaps have the greatest need for this therapy, but rather conventional wound care must be relied on.

We have therefore defined a need for improved dressings, more particularly but not exclusively composite TNP therapy dressings, which exhibit enhanced adaptability in wound care.

It is an aim of certain embodiments to at least mitigate the above-mentioned problems. Certain embodiments disclosed herein relate to improved compositions and their use in combination with dressings to confer enhanced adaptability in wound care, preferably in TNP wound care. Dressings applied in combination with such compositions may have advantages over traditionally applied dressings which may be more difficult to apply, particularly around wounds such as lengthy incision sites or irregularly shaped wounds. Dressings applied to such wounds with use of such compositions may be of comparable effectiveness to dressings applied in traditional manner to more regular sized or shaped wounds. Wounds dressed with such dressings in combination with such compositions may enable the application of TNP therapy. Also disclosed are improved methods of use and systems for use of the compositions in combination with dressings, preferably in negative pressure wound therapy.

It is an aim of certain embodiments to provide means to enable composite wound dressings to more universally be used on wounds of different shapes or sizes.

It is an aim of certain embodiments to provide a dispensable sealant composition for a composite wound dressing which can more universally be used on wounds of different shapes or sizes.

It is an aim of certain embodiments to provide a device including such composition for dispensing in improved manner to a composite wound dressing to more universally be used on wounds of different sizes or shapes.

It is an aim of certain embodiments to provide a wound dressing kit including a composite dressing, preferably an advanced wound management dressing, more preferably a composite TNP therapy dressing, together with a sealant composition, adapted to be applied in conjunction at a wound site.

It is an aim of certain embodiments to provide an apparatus in the form of a composite wound dressing which can more universally be used on wounds of different shapes or sizes.

It is an aim of certain embodiments to provide a method of treating a wound by sealing a composite dressing which can more universally be used on wounds of different shapes or sizes.

In one embodiment, there is provided a dispensable composition for woundcare,
   wherein the composition is dispensed into a wound dressing location, said wound dressing comprising:
      a backing layer having an upper surface and a lower surface, otherwise termed a backing sheet having two faces, and defining a perimeter configured to be positioned over skin surrounding a wound site; an optional wound contact layer;
      one or more transmission layers provided directly or indirectly to the lower backing layer surface, or otherwise configured to be positioned below the backing layer, or otherwise positioned at or on one side of one face of the backing sheet,
      or enclosed between the backing layer and the wound contact layer, where present; and
      a port configured to transmit negative pressure through the backing layer for the application of topical negative pressure at the wound site
   wherein removing a portion of the wound dressing directly enclosing the transmission layer to create a main wound dressing portion with one or more exposed portions wherein the transmission layer is exposed at a portion thereof,
      said exposed portion(s) being the location as hereinbefore defined, the dispensed composition seals the exposed portion(s).

The composition is particularly for creating a main wound dressing portion for use in wound care more particularly for sealing a trimmable dressing, having a main dressing portion or cell in fluid (e.g., gas) communication with additional dressing portions or cells, for use in woundcare, more particularly for treatment of a wound site.

The composition may be dispensed into or onto the exposed portion or both. By this means the dispensed composition impregnates or envelopes the exposed portion or both.

Preferably the dispensed composition impregnates the exposed portion. This has the advantage of enhanced robustness whereby the seal forms part of the dressing.

Alternatively the dispensed composition envelopes the exposed portion. This more resembles a simple repair applied to the upper surface of the dressing. Choice of dispensing by impregnation or enveloping may be selected according to the nature of the dressing to be sealed, in particular its laminar structure, and more particularly the laminar structure at the exposed portion thereof. Optionally the composition impregnates and additionally envelopes the sealed portion thereby providing a seal operating at internal surfaces of the transmission layer and external surfaces of the dressing. Composition may be dispensed directly at the exposed portion through the exposed face thereof, or indirectly via the backing layer or backing sheet or via the optional wound contact layer, thereby internally penetrating the exposed portion.

Some embodiments may further comprise a device comprising the composition, an apparatus in the form of a dressing for use with the composition, kits thereof, uses and methods of therapy. Some embodiments may further comprise a source of negative pressure configured to supply negative pressure through the port. Some embodiments may further comprise retention strips or sealing strips configured to hold in place or seal the dressing to skin surrounding a wound.

In another embodiment, a method of creating a main wound dressing portion for use in dressing or otherwise of treating a wound comprises:

providing a wound dressing as hereinbefore defined comprising:
a backing layer, otherwise termed a backing sheet;
an optional wound contact layer; and
one or more transmission layers as hereinbefore defined
removing a portion of the wound dressing to create a main wound dressing portion with one or more exposed portions;
optionally positioning the main wound dressing portion over a wound and sealing the main wound dressing to skin surrounding the wound,
and dispensing a composition as hereinbefore defined to a location comprising the one or more exposed portions of the main wound dressing portion thereby sealing the exposed portion(s); and
optionally applying negative pressure to the wound through the backing layer of the main wound dressing portion.

Sealing a wound dressing to skin may be prior to creating a main wound dressing portion and prior to dispensing composition or may be subsequent to creating a main wound dressing portion and prior to or subsequent to dispensing composition. Accordingly the method may be a method relating to dressing manufacture for use in dressing wounds or may be a method relating to dressing wounds. As is used herein the backing layer represents a gas impermeable membrane. Also referred to herein as wound cover or drape. Some examples of materials suitable for backing layers included thin polyurethane films, which may optionally be coated with adhesive. It is also possible that a number of laminates be brought together to form multi-laminar backing layers, in such cases the description of the upper and lower surfaces of the backing layer are taken to mean the upper and lower surfaces of the complete backing layer.

As is used herein, a dressing also comprises one or more transmission layers and other layers (such as absorbent material) positioned beneath the backing layer. For example, one or more transmission layers or other layers may be positioned or enclosed between a backing layer and an optional wound contact layer, for example, sealed therebetween. The transmission layer(s) may be in turn positioned between the backing layer and (optional wound contact layer and) a wound site over which the dressing is configured to be positioned, for example sealed therebetween.

A transmission layer as described herein allows transmission of fluid such as air, and optionally additionally other gases and liquids, away from a wound site into upper layer(s) of the wound dressing, the port, and therefrom to a fluid canister if present and/or into a negative pressure pump. A transmission layer may assist in maintaining an open air channel to communicate negative pressure over the wound area even when the dressing is handling substantial amounts of exudates. The layer should remain open under the typical pressures that will be applied during negative pressure wound therapy. Preferably, a transmission layer remains open over an area corresponding to the wound site, and thereby ensures that the whole wound site sees an equalised negative pressure. Alternatively the transmission layer may comprise one or more specific air paths which remain open, such as in and between bridging portions of a wound dressing as described further below.

A transmission layer may comprise voids or may comprise one or more materials which transmit fluid, or may be a combination thereof. The transmission layer may incorporate other functional materials provided that it is still capable of transmitting negative pressure, and preferably also liquid fluids. In some embodiments, the transmission layer is capable of transmitting wound exudates and other compositions of matter.

Some examples of materials suitable for a transmission layer include a three dimensional structure, for example, a knitted or woven spacer fabric (for example Baltex 7970 weft knitted polyester), although other materials such as foam (e.g., reticulated foam), nonwoven materials (e.g., an acquisition distribution layer as described below) could of course be used. Alternatively or additionally the transmission layer may incorporate absorbent material and absorb liquid drawn away from the wound under the applied negative pressure.

Some embodiments described herein include a trimmable dressing, having a main dressing portion or cell in fluid (e.g., gas) communication with additional dressing portions or cells. As is used herein, a main dressing portion represents a portion which has a size or shape or profile or articulation which is compatible with a wound or wound site to be dressed. One or more additional portions or cells may be removed to provide a dressing having a size or shape or profile or articulation which is to be compatible with a wound or wound site to be dressed. Preferably a large surface area, or elongate main dressing portion is provided to dress a similarly large surface area or elongate wound; for example portions or cells may be retained to provide such a large surface area, or elongate main dressing portion, or portions or cells may be removed to dress a correspondingly reduced surface area or reduced length wound. preferably a shaped main dressing portion is provided to dress a similarly shaped wound; or a shaped main portion is provided to dress a wound incorporating or adjacent a protrusion such as a device, for example a pin, or such as a body part such as a digit, for example one or more additional portions or cells may be conformed to provide a shaped dressing; preferably a profiled main dressing portion is provided to dress a similarly profiled wound or wound site, such as a wound located on complex body topography, for example one or more additional portions or cells may be conformed to provide a profiled dressing; preferably an articulated main dressing portion is provided to dress a similarly articulated wound or wound site such as a wound located on a joint, for example one or more additional portions or cells may be articulated.

A main dressing portion or portions and additional portions or cells as described herein may be connected by one or more bridge portions including one or more transmission layers as described above, in other words a bridging portion underneath the backing layer, or otherwise positioned at or on one side of one face of the backing sheet, the bridging portion comprising at least one material layer configured to transmit negative pressure from the first portion through the bridging portion. In some embodiments, the at least one material layer in the bridging portion has a smaller dimension or a different material structure than a corresponding dimension or material structure of the first portion, for example the one or more transmission layers comprising one or more bridging portions having a smaller width than adjacent portions of the one or more transmission layers or than the main dressing portion, or the one or more transmission layers comprising one or more bridging portions having a smaller height than adjacent portions of the one or more transmission layers or than the main dressing portion.

As is used herein, an exposed portion of transmission layer represents a portion which the backing layer is not configured to enclose and seal against a surface such as a wound site, for example the backing layer and optional wound contact layer do not enclose the transmission layer. For example, a section of transmission layer and overlying backing layer is absent, whereby the remaining transmission layer terminates in open-ended manner, or the backing layer may be partially absent, and additionally the optional wound contact layer may be partially absent, at which the transmission layer terminates in open-ended manner. It may be desired to seal such exposed portion of transmission layer (and exposed portions of other layers). As is used herein, sealing represents sealing in manner to contain fluid, more preferably in manner to contain negative pressure.

As is used herein, fluid represents liquid and gas. However it is not intended that "fluid" should encompass "vapour", a favourable moisture vapour transmission rate (MVTR) being a requirement of dressings envisaged herein. The backing layer is impermeable or substantially impermeable to fluids including wound exudate. The backing layer is air-tight or substantially air-tight, whereby a negative pressure may be maintained at a wound site to which the dressing is applied and sealed with the composition. Wound exudates and other fluids may be contained within the wound site and/or dressing and any collection means associated therewith.

As is used herein, a dispensable composition represents a composition having viscosity in the range from 5 to 300 Pa·s, preferably 10-100 Pa·s. Viscosity (q) is determined in accordance with DIN EN ISO 3219: 1994, Annex B. For some embodiments viscosity is in the range 20-80 Pa·s. The composition parts may be combined and allowed to partially cure to a suitable viscosity for application, or may have properties such that a suitable viscosity reduction is achieved when subject to shear forces during application. The composition may have flow properties such that it can be drawn within transmission layer(s) at exposed portion(s) by the prevailing negative pressure and then cure. The composition ay for example flow to a distance of up to 25 mm, eg 1 mm to 25 mm. The cured sealant preferably retains a degree of flow or conformability, for example extensibility, such that it can accommodate the dynamic conditions encountered when on the skin.

As is used herein a TNP system may be operated with any suitable source of negative pressure, including and not limited to pumps, springs (SNaP) and any other functional equivalents.

As is used herein, a wound dressing represents a composite wound dressing, preferably an advanced wound management dressing tailored to include specific wound therapy provision for i.a. management of wound exudates (eg ALLEVYN Gentle Border, DURAFIBER, ALLEVYN Life), infection management (eg ACTICOAT, IODOSORB), iv site care (eg IV3000), management of compromised skin about the wound, TNP (eg RENASYS F/AB, PICO, KCl Prevena, Kalypto Medical Inc NPD1000 NP Wound Therapy System), post operative care such as surgical drapes (eg OPSITE), temporary bioskin dressings (eg BIOBRANE) and the like, most preferably a TNP dressing.

BRIEF DESCRIPTION OF THE DRAWINGS

FIGS. 4A and 4C illustrate an exploded view of an embodiment of a wound dressing;

FIGS. 4B and 4D illustrate a cross sectional view of an embodiment of a wound dressing;

Figure 8C:
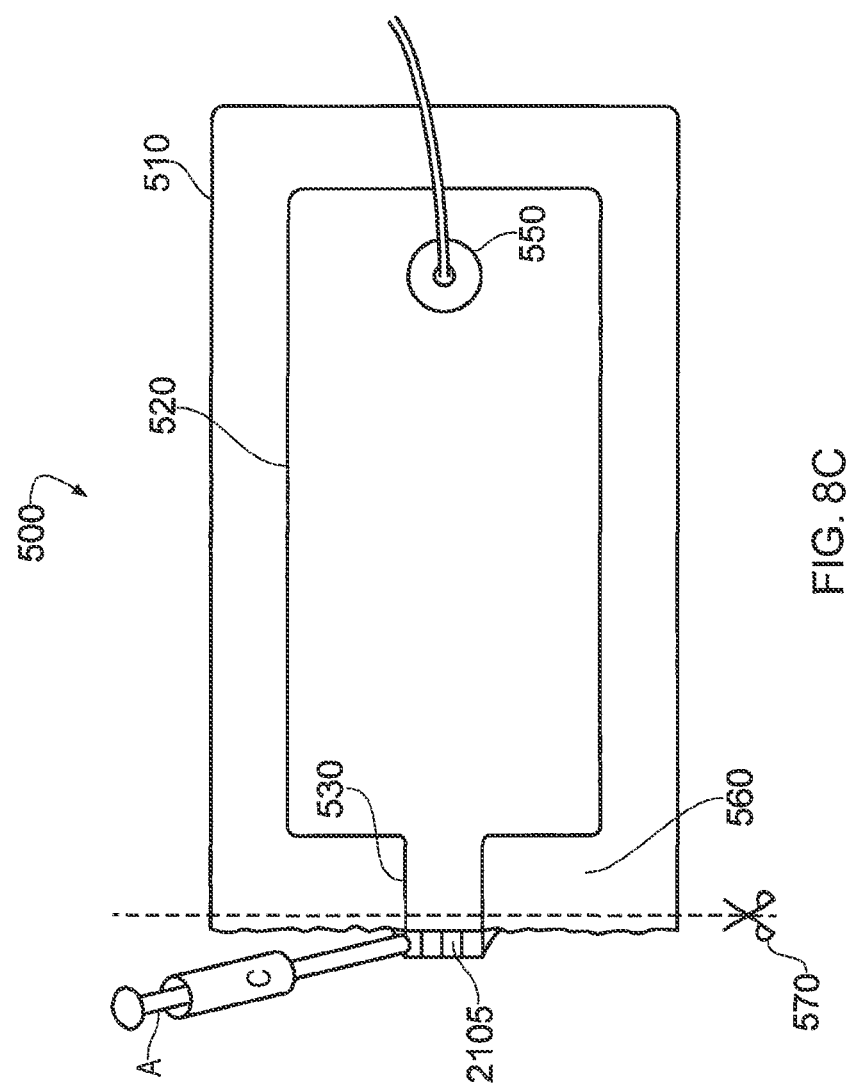
Figure 8D:
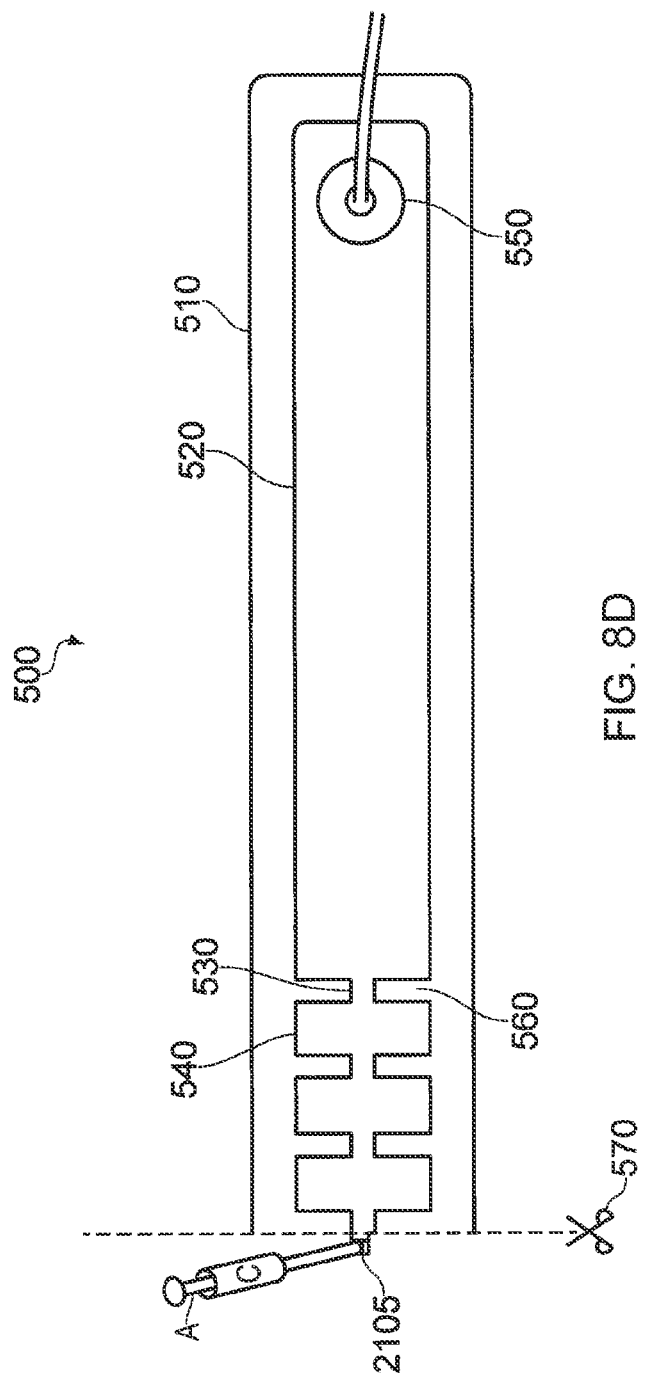
Figure 9A:
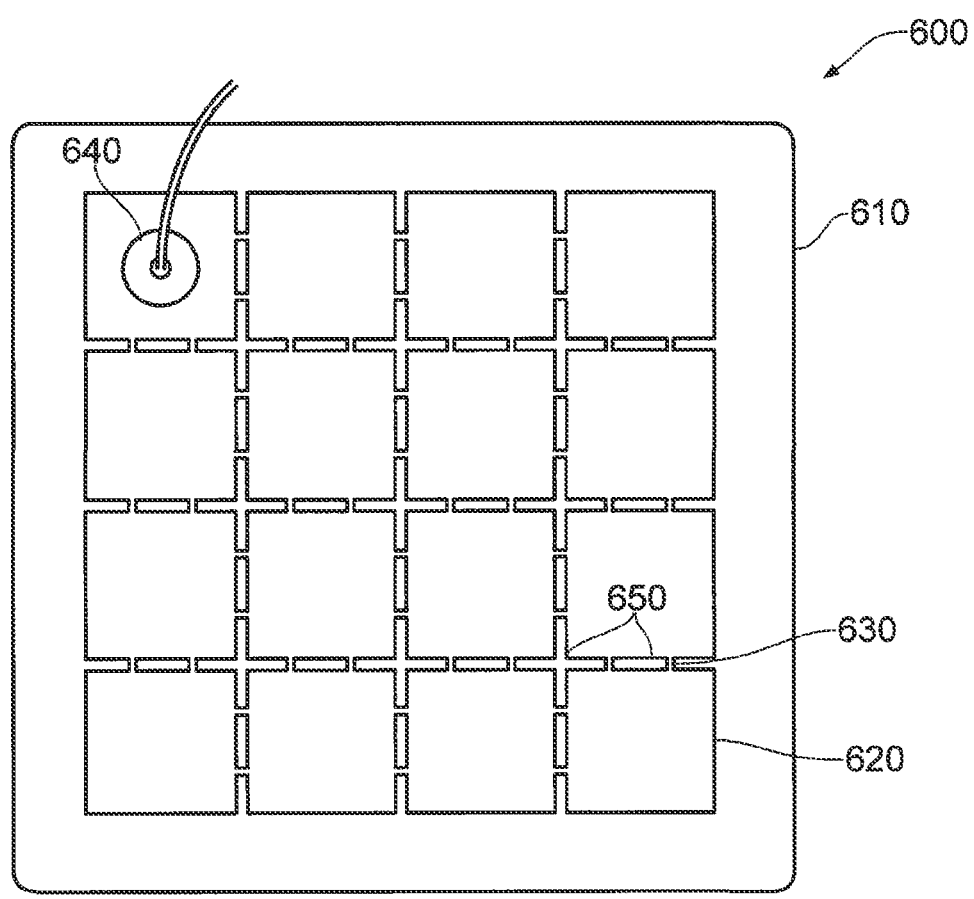
Figure 9B:
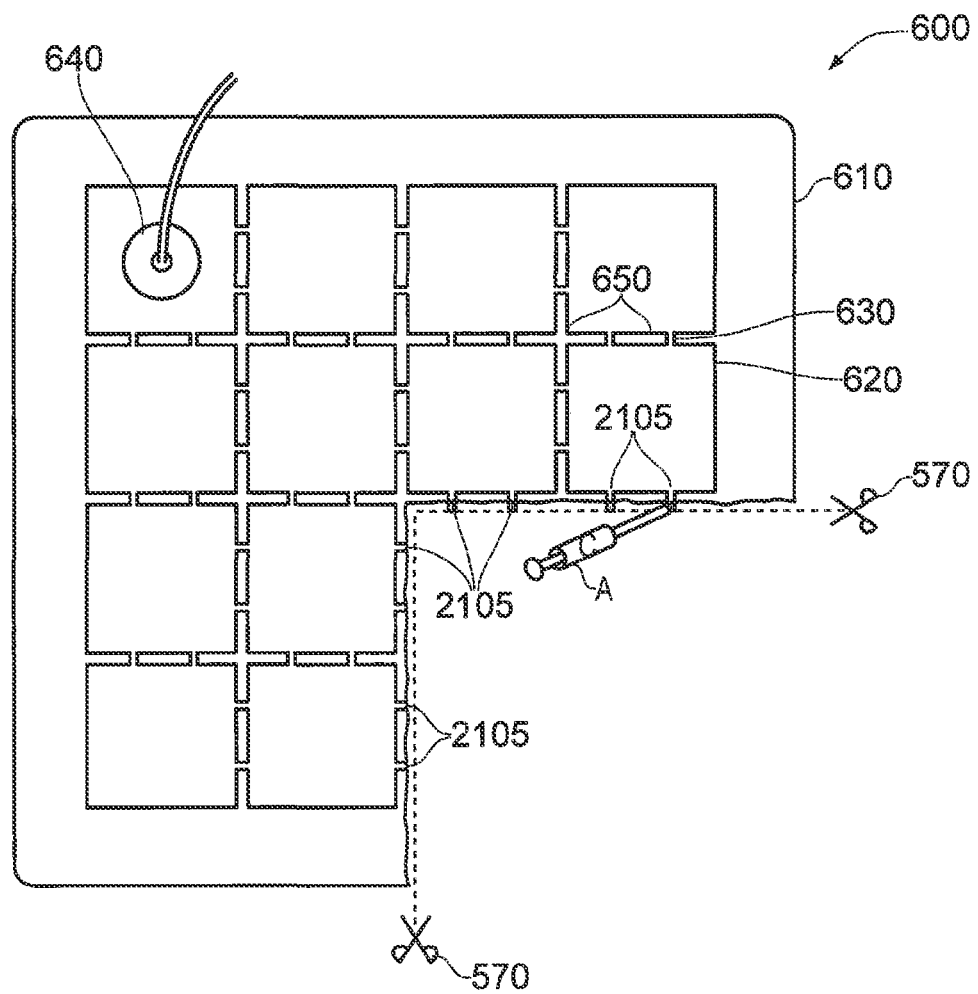
Figure 10A:
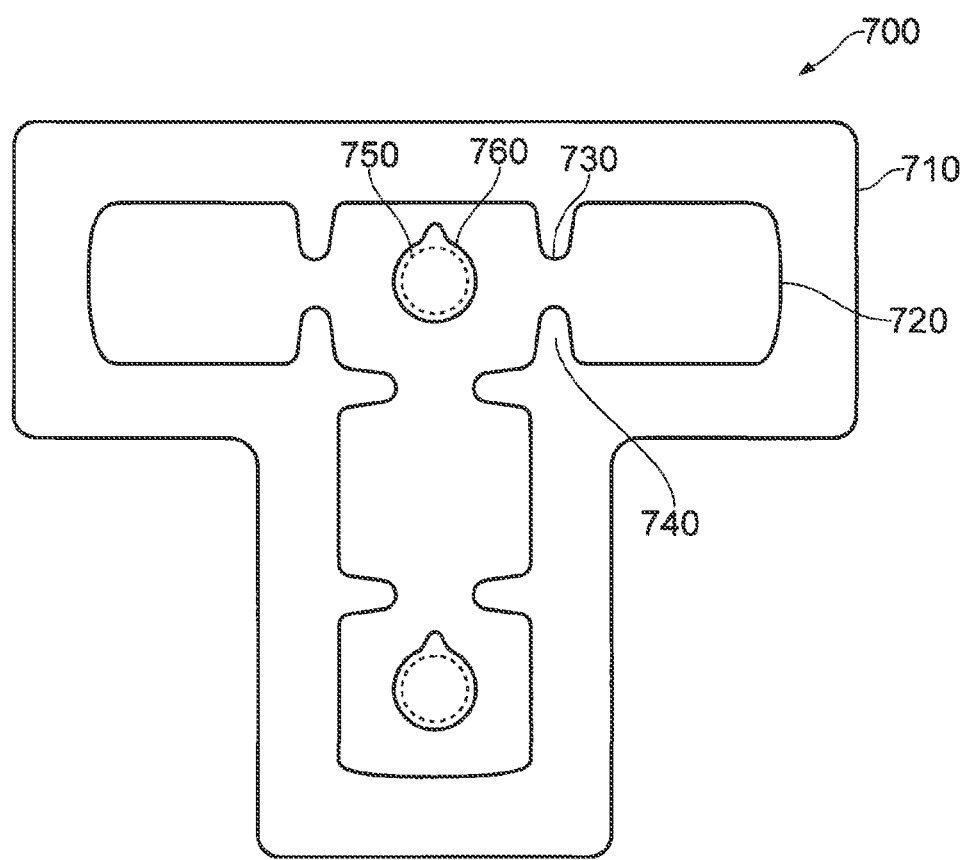
Figure 10B:
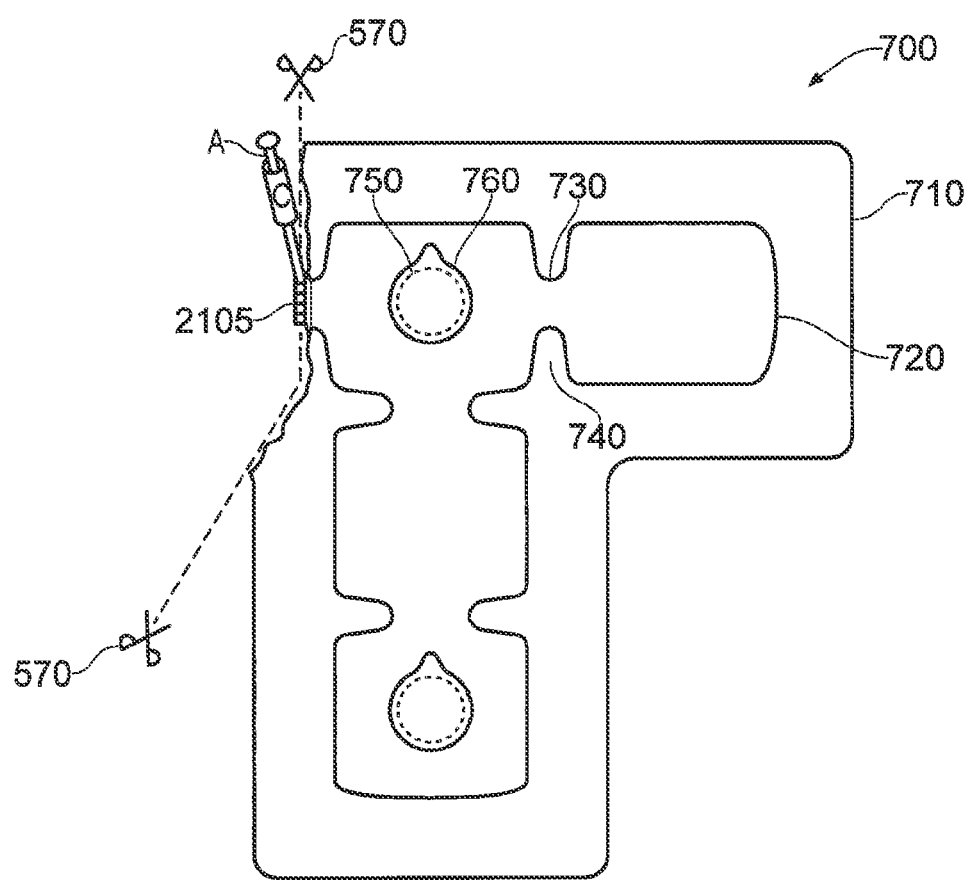
Figure 11A:
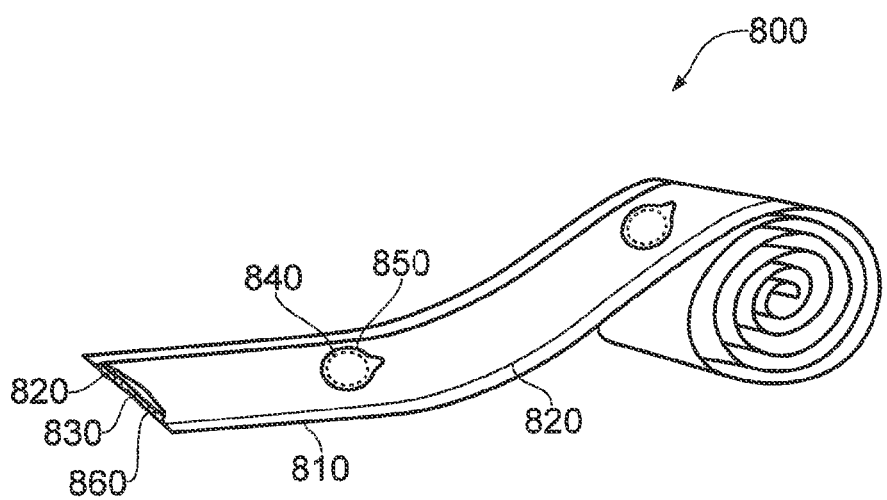
Figure 11B:
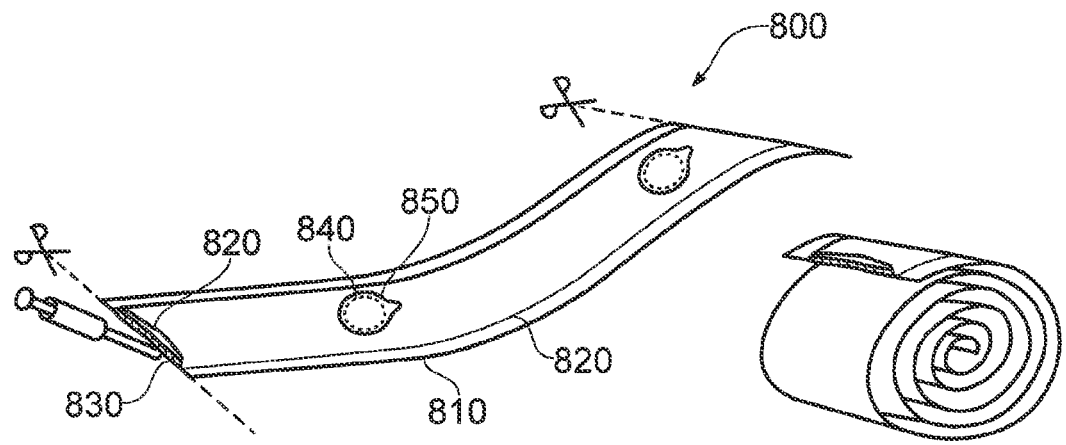

and 7A-7D also illustrate the sealing of embodiments of wound dressings; and 7G also illustrates a novel nozzle head for an applicator;

FIG. 8A illustrates an embodiment of a wound dressing trimmable at a bridge portion; FIG. 8B illustrates another embodiment of a wound dressing trimmable at a bridge portion;

FIGS. 8C and 8D illustrate the use and application and sealing of embodiments of FIGS. 8A-8B onto a patient;

FIG. 9A illustrates an embodiment of a trimmable wound dressing comprising a plurality of portions or cells;

FIG. 9B illustrates the use and application and sealing of an embodiment of FIG. 9A onto a patient;

FIG. 10A illustrates an embodiment of a trimmable T-shaped wound dressing comprising a plurality of portions with multiple port attachment sites;

FIG. 10B illustrates the use and application and sealing of an embodiment of FIG. 7 onto a patient;

FIG. 11A illustrates an embodiment of a trimmable wound dressing with multiple port attachment sites; and FIG. 11B illustrates the use and application and sealing of an embodiment of FIG. 11A onto a patient.

Figure 12A:
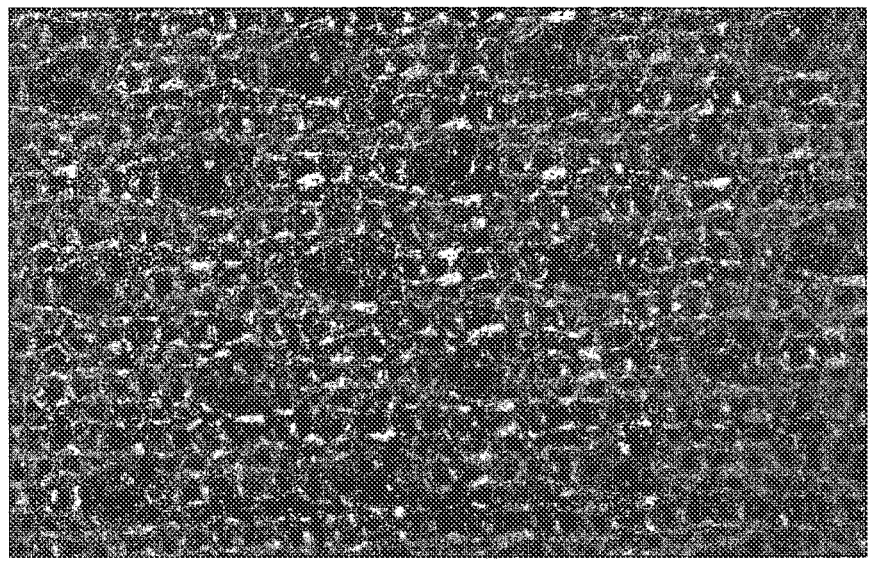
Figure 12B:
Figure 14A:
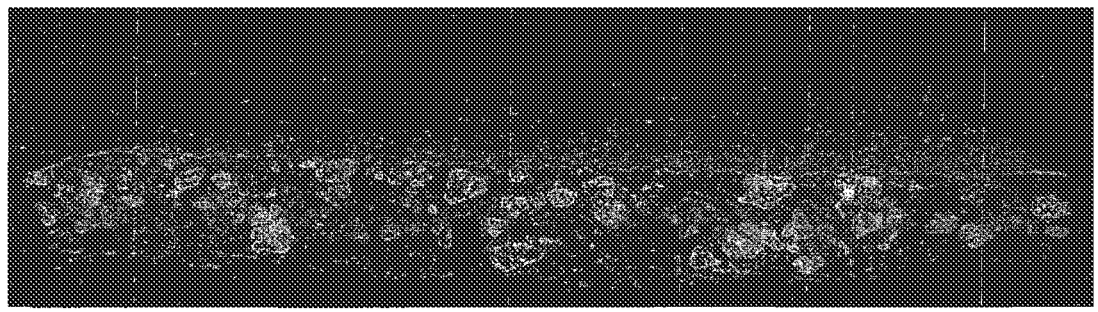
Figure 14B:
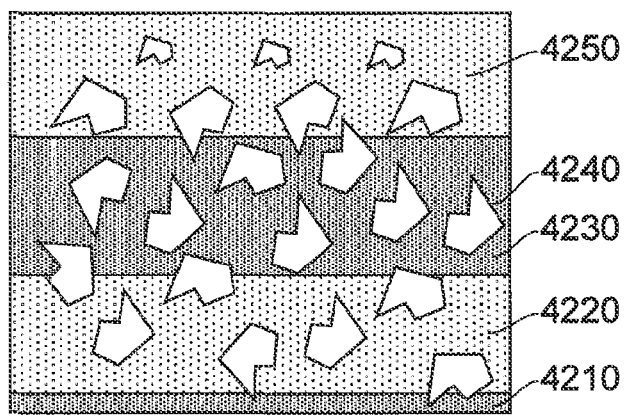
Figure 15A:
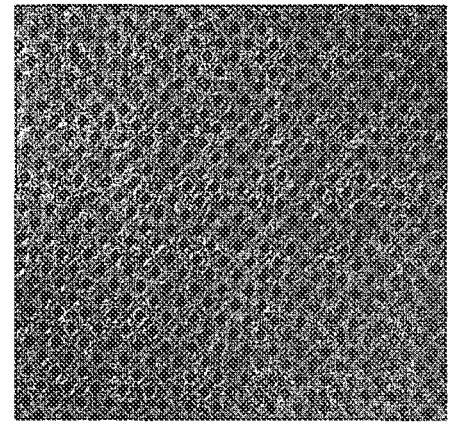
Figure 15B:
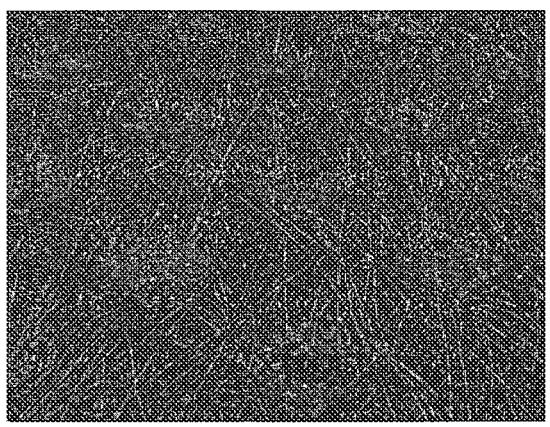
Figure 16:
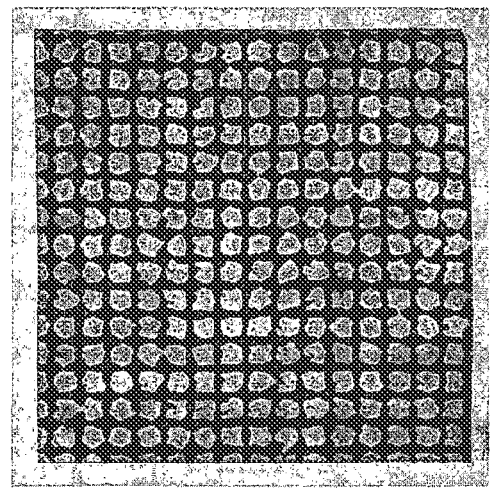
Figure 18:
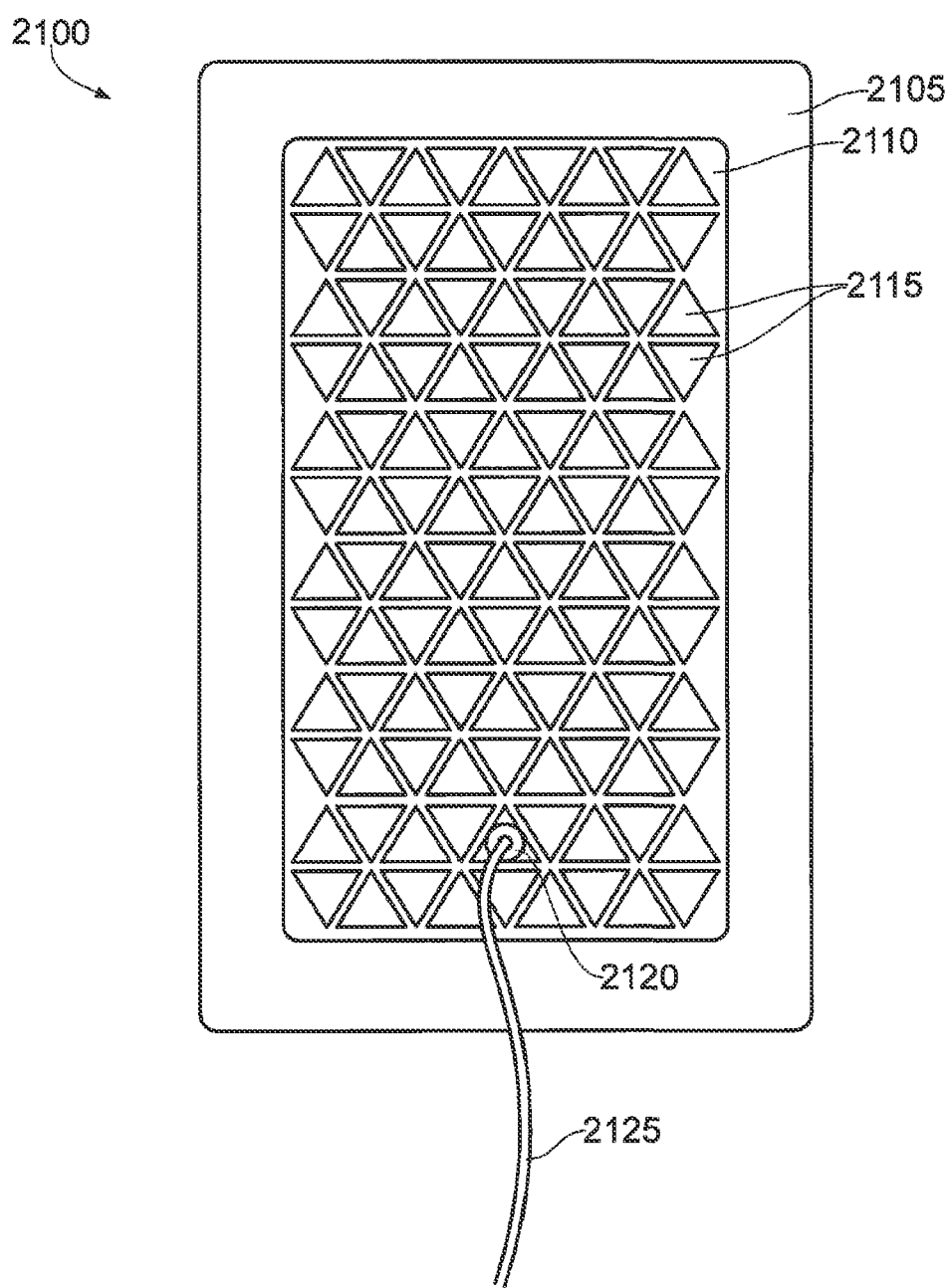
Figure 19A:
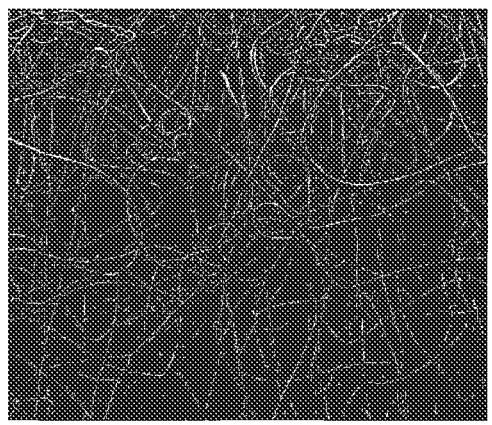
Figure 19B:
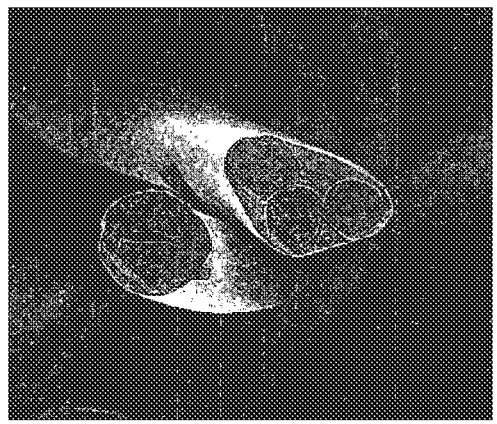
Figure 20A:
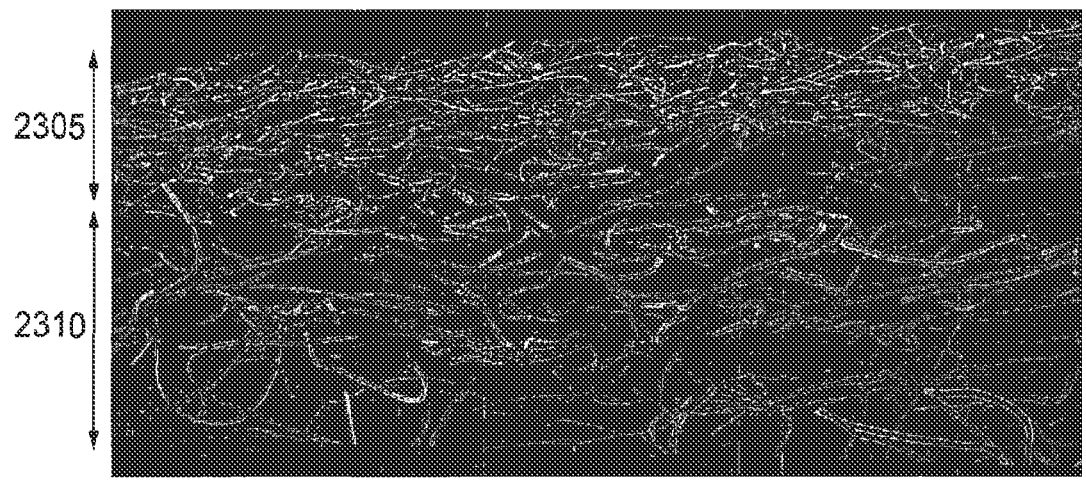
Figure 20B:
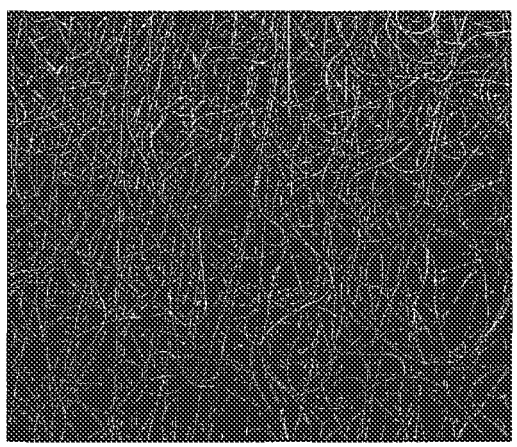
Figure 20C:

FIGS. 12A and 12B illustrate one embodiment of spacer layer material;

FIGS. 13A-13D illustrate one embodiment of acquisition distribution layer material;

FIGS. 14A and 14B illustrate one embodiment of absorbent layer material;

FIGS. 15A and 15B illustrate one embodiment of obscuring layer material;

FIG. 16 illustrates one embodiment of an adhesive spread on cover layer material;

FIGS. 17A-17B illustrate one embodiment of a trimmable dressing having a reduced height bridging portion;

FIG. 18 illustrates an embodiment of a trimmable wound dressing comprising a plurality of portions or cells;

FIGS. 19A and 19B illustrate another embodiment of acquisition distribution layer material; and FIGS. 20A through 20C illustrate another embodiment of acquisition distribution layer material.

DETAILED DESCRIPTION OF THE PREFERRED EMBODIMENTS

Embodiments disclosed herein relate to compositions, devices, apparatuses, uses, kits and methods of treating a wound with reduced pressure, including pump and wound dressing components and apparatuses. The apparatuses and components comprising the wound overlay and packing materials, if any, are sometimes collectively referred to herein as dressings, unless otherwise indicated or intimated. Throughout the specification, the terms sealant and composition are hereinafter used interchangeably unless otherwise indicated or intimated.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, stemiotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, cosmetic wounds, trauma and venous ulcers or the like. Wounds may include readily accessible and difficult to access wounds, exposed and concealed wounds, large and small wounds, regular and irregular shaped wounds, planar and topographically irregular, uneven or complex wounds, more preferably on a site selected from the torso, limb and extremities such as heel, sacrum, axial, inguinal, shoulder, neck, leg, foot, digit, knee, axilla, arm and forearm, elbow, hand or for sealing a crevice adjacent or adjoining a wound site, selected from such as sacral cleft, fossa and the like.

It will be understood that embodiments of the present disclosure are generally applicable to use in topical negative pressure ("TNP") therapy systems. TNP therapy sometimes referred as vacuum assisted closure V.A.C.® or negative pressure wound therapy (NPWT) using sub-atmospheric pressure is applicable to a broad range of wounds such as chronic wounds, incisional wounds, open wounds and abdominal wounds or the like.

Briefly, TNP assists in the closure and healing of many forms of wound, by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

During TNP therapy, a suction source such as a vacuum pump or the like is utilised to create a negative pressure region. That is to say, a region where an experienced pressure is below that of the surroundings. The suction source creates a negative pressure via a dressing or drape positioned over and sealed about or around the periphery of the wound. Wound exudate and other potentially harmful material is enclosed under the dressing or drape and extracted therefrom.

As is used herein, reduced or negative pressure levels such as $-X$ mmHg, represent pressure levels that are below standard atmospheric pressure, which corresponds to 760 mmHg (or 1 atm, 29.93 in Hg, 101.325 kPa, 14.696 psi, etc.). Accordingly, a negative pressure value of $-X$ mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (e.g., $-40$ mmHg is less than $-60$ mmHg). Negative pressure that is "more" or "greater" than $-X$ mmHg corresponds to pressure that is further from atmospheric pressure (e.g., $-80$ mmHg is more than $-60$ mmHg).

The negative pressure range for some embodiments of the present disclosure can be approximately $-80$ mmHg, or between about $-20$ mmHg and $-200$ mmHg. Note that these pressures are relative to normal ambient atmospheric pressure. Thus, $-200$ mmHg would be about 560 mmHg in practical terms. In some embodiments, the pressure range can be between about $-40$ mmHg and $-150$ mmHg. Alternatively a pressure range of up to $-75$ mmHg, up to $-80$ mmHg or over $-80$ mmHg can be used. Also in other embodiments a pressure range of below $-75$ mmHg can be used. Alternatively, a pressure range of over approximately $-100$ mmHg, or even 150 mmHg, can be supplied by the negative pressure apparatus. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Canisterless NPWT (omitting a dedicated canister to contain wound exudate) has also been considered using negative pressure values in the same range as conventional NPWT. More preferably −40 to −200 mmHg. More preferably −40 to −140 mmHg.

Embodiments address the problem of providing dressings in a range of sizes and shapes to accommodate irregularly shaped wounds and body topography, for example vein harvest wound dressings accommodating variations in height and leg-length of individuals, which is impractical both to the manufacturer and to the user. Embodiments enhance adaptability of existing dressings, and of more recently introduced multisite dressings such as trilobes and quadrilobes. Embodiments enable a portion of a dressing to be removed to create a main wound dressing of desired size or shape or profile or articulation, and sealing exposed portion(s) thereof to contain a negative pressure.

Exposed portion(s) as hereinbefore defined are the result of removing a portion of the wound dressing, which may be by any envisaged means, for example cutting the wound dressing or tearing along a weakened line. Composite wound dressings may comprise a border for affixing around a wound, about a central wound contact portion. The dressing as hereinbefore defined may include a backing layer and wound contact layer of similar footprint or surface area to the transmission layer or other layers enclosed therebetween (i.e. a borderless dressing) or of greater footprint or surface area than the transmission layer enclosed therebetween (i.e a bordered dressing). Exposed portion(s) as hereinbefore defined result from removing a portion of the wound dressing as hereinbefore defined directly enclosing the transmission layer, for example by cutting into or through the backing layer and wound contact layer and the transmission layer therebetween.

The portion(s) of the wound dressing may be removed to size the main wound dressing portion for positioning over a wound as hereinbefore defined, for example an incisional wound, an elongate leg wound, an arcuate incisional wound and the like. Similarly the portion(s) of the wound dressing may be removed to shape the main wound dressing portion for positioning over a wound as hereinbefore defined, such as a flap wound, over a protruding device such as a fixation device or a protruding body part, to profile the main wound dressing for positioning over a wound as hereinbefore defined, for example on complex body topography, or to articulate the main wound dressing for positioning over a wound as hereinbefore defined for example on a flexing joint.

Preferably a dressing is skin compatible. Skin compatible as used herein refers to the ability to apply or reapply a dressing and in particular a backing layer or wound contact layer to skin and remove from skin without trauma to the wearer, and without causing substantial damage to the skin. Skin compatible materials include adhesive or non-adhesive materials such as pressure sensitive adhesive (PSA), typically acrylic, hydrocolloid, silicone and silicone based materials and other materials as hereinbelow recited. A particularly well known skin compatible material comprises silicone or is silicone based, and skin compatible materials are envisaged having properties corresponding to silicone or silicone based material.

Composition and Method for Dispensing

The composition may be selected from a curing system and a non-curing system. Ideally this is a material that will not flow substantially from its application site but that during application is either shear thinning or shape conformable when subject to load. A curing system may be selected from a curable one or more parts composition, for example silicone curing systems which may include one, two or more part silicone systems and may include a range of curing mechanisms, epoxy curing systems, cyanoacrylate curing systems, polyurethane curing systems, polymeric systems functionalised with silicone chain linking functional groups, polymeric system functionalised with polyurethane curing functional groups, drying system such as an elastomer rendered fluid by the presence of a volatile solvent, spray on elastomers such as acrylic in water or solvent base, UV or light curing systems.

A non-curing system may be selected from a one or more part composition, for example a putty, a jelly such as petroleum jelly, grease such as silicone grease, a gel such as a hydrogel, organogel or xerogel, a paste, a colloidal system such as a hydrocolloid.

Preferably the composition dispensed to a location as hereinbefore defined forms an elastomeric seal.

Curing time of a curable composition is not a limiting feature. A curing composition usefully has curing time at 23° C. in the range from 0.05 min to 24 hours, eg 0.5 to 20 min, more preferably from 0.5 to 18 min, more preferably from 0.5 to 16 min, most preferably 12 min, most preferably 0.5 to 5 min. Cure time is manual kinetic as known in the art.

A number of methods are known in the art to monitor the cure of liquid polymers and in particular RTV-2 silicones, these vary from continuous monitoring across the full cure profile of the material with instruments such as scanning vibrating needle curemeters (B. G. Willoughby and K. W. Scott, *Understanding cure with the scanning vibrating needle curemeter* (scanning VNC), RTL/2844, Rapra Technology Limited, Shawbury) or differential scanning calorimeters (L. M. Lopez, A. B. Cosgrove, J. P. Hernandez-Ortiz, T. A. Osswald, *Modeling the Vulcanization Reaction of Silicone Rubber*, Polym. Eng. Sci., 2007, 47, 675-683) through to empirical single point determinations typically based on clear physical changes, for example recording the time taken to reach the gel point.

During the trials described in the examples it was found that transfer of uncured sealant from the application site to other surfaces was a clear disadvantage. For the purpose of defining an unambiguous single point on the cure profile, cure time is taken to mean manual kinetic cure time. Manual kinetic cure time is herein defined as the cure time (at a specified temperature) at which material is no longer transferred to skin (i.e. a fingertip) when subject to a light, brief touch.

Due to the temperature dependence of the cure profile on addition cure RTV silicones it is important that comparison between any measurements is carried out at the same temperature and that the temperature be reported. Guidance set out in *Methods of Test for Surgical Dressings* in the British Pharmacopoeia (BP), 1993, 14$^{th}$ edition, A222, Appendix XX is that the temperature of a regulated atmosphere is taken as 20° C.±2° C. Within the silicone industry there are many instances where curing parameters of addition cure RTV-2 silicones are reported at a nominal temperature of 23° C., this falls in line with standard test methods for other temperature dependant properties such as viscosity (when measuring viscosity DIN EN ISO 3219: 1994 describes a preferred measurement temperature of 23.0° C.±0.2° C.), examples of this include: Pot Life reported by Wacker Silicones (at 23° C. on Technical data sheet for Silpuran® 2445 A/B, Version 1.3 & Technical data sheet for Silpuran® 2450 A/B, Version 1.3, Wacker Chemie AG, Munchen); *Maximum Working Time* reported by Bluestar Silicones (at 23° C. on The Silbione® Difference, Silicones for Healthcare Applications, Bluestar Silicones France SAS, Lyon) and Pot Life reported by Momentive (defined as the time for initial viscosity to double at 23° C. on Silicone Gels for Healthcare Applications, 152-053-00E-GL, Momentive Performance Materials Inc., Columbus). When considering the temperature of a material applied to skin, it should be noted that the temperature of skin is nominally taken as 32° C. In a clinical environment, when a curing RTV-2 silicone is applied as a thin bead, layer or film in intimate contact with the skin, it has been assumed that the material will reach thermal equilibrium with the skin rapidly.

Within the literature other discrete points along the cure profile are routinely used, of note are: pot life, this usually indicates the maximum period of time after which the mixed silicones may still be worked, poured, spread etc. Where flow is an important requirement pot life is usually quoted as the time required for the initial viscosity to double (Elastosil, Processing RTV-2 silicone rubbers, 6020e/06.06, Wacker Chemie AG, München) and tack free time, this is an appropriate measure when considering a rubber (by definition the material must not have any discernible tack or grab once cured) and may be assessed in a similar way to manual kinetic.

Preferably the composition has cure time as hereinbefore defined at 23° C. in the range from 0.5 min to 20 min, more preferably from 0.5 to 18 min, more preferably from 0.5 to 16 min, most preferably 12 min, most preferably 0.5 to 5 min. Cure time is manual kinetic as hereinbefore defined.

Values at 32° C. are particularly instructive in the present application, preferably cure time at 32° C. is in the range 0.5 to 10 minutes, more preferably 0.5 to 8 minutes, most preferably in the range 0.5 to 7 minutes.

Tack

Tack is hereinbelow measured as maximum force required to separate a probe from cured composition. However for the purpose of determining tack-free or low tack time, a touch and lift test was performed at intervals with the finger, on controlled samples, and tack free or low tack time determined as the time at which the sample did not adhere to and lift with touch.

Preferably tack-free time is in the range from 0.5 to 25 minutes, more preferably from 0.5 to 22 minutes. Preferably the composition has tack as hereinbeforedefined at a period in the range from 0.5 minutes to 22 minutes after combining such as to not adhere items such as paper or clothing which contact the composition. Finger tack is a relatively subjective evaluation which can be obtained by touching the surface of the dispensed composition to determine the "stickyness" thereof. Descriptive terms such as high H), low (L) and moderate (M) can then be attributed as a preliminary measure.

Preferably a composition intended for external seal of the exposed portion forms a substantially tack free seal in a period as hereinbefore defined. Preferably a composition intended for internal seal within the bridging portion forms a substantially tack free to moderate tack seal.

Viscosity

Preferably as hereinbefore defined, compositions having low viscosity in the range 11-14 $Pa.s^{-1}$ are of particular advantage when dispensed internally.

A composition may be shear thinning, to assist application, for example exhibiting change in viscosities with shear rate, for example as follows:

| Target shear rate ($s^{-1}$) | viscosity (eg range) $mPa.s^{-1}$ |
|---|---|
| 1.0 | 250 (240-270) |
| 2.50 | 80 (65-94) |
| 5.00 | 55 (42-63) |
| 10.00 | 40 (33-51) |
| 25.00 | 20 (20-25) |
| 50.00 | 15 (9-21) |
| 100.00 | 10 (5-13) |

Shear thinning compositions advantageously revert to their rest viscosity and remain in place once the dispensing force or applicator force is removed.

Alternatively a rapid onset of cure stabilises the composition in position. Preferably composition penetrates within the transmission layer and optional additional layers to a distance of from 1 mm to 10 mm, for example substantially 5 mm. Penetration should not exceed 25 mm.

Extensibility

A dressing as hereinbefore defined should approximate as closely as possible to skin, to minimize discomfort and to maximize the beneficial effects thereof. WO02009/156709 discloses the properties of skin specifically in relation to extensibility, which are to be approximate by a dressing. Preferably the composition cures to a seal which approximates to the extensibility of the dressing which it seals and/or the extensibility of the skin of the wearer. Preferably the composition after curing as a sample with a height of 1 mm has extensibility comparable to or greater than the main dressing portion, bridging portion, trimming portion(s) or component layers thereof up to a maximum corresponding to the backing sheet. For example for the backing sheet the load required to produce a 20% extension at a rate of extension of 300 mm per minute is in the range of less than or equal to 1.4 kgf per cm width ($kgfcm^{-1}$), preferably in the range 0.001 to 1.4 $kgf cm^{-1}$ expressed preferably as 0.001 to 14.0 $kgf cm^2$ to produce 20% extension, more preferably in the range 0.001 to 5.0 $kgf cm^2$.

The extensibility of a typical spacer layer is approximately: 0.08 $kgfcm^{-1}$ (Direction A); 0.07 $kgfcm^{-1}$ (Direction B) The extensibility of a typical superabsorber layer (Laminate EU33 top film, superabsorbent airlaid (Chempositie 11C/450 airlaid superabsorbent pad, spacer layer Baltex 7970 and perforated Si wound contact layer is approximately 0.59 $kgfcm^{-1}$ (Direction A); 0.78 $kgfcm^{-1}$ (Direction A).

Preferably extensibility of seal as hereinbefore defined is 0.04 to 3.00, more preferably 1.00 to 2.50.

Permanent Set

Permanent set for the cured seal enclosed within the layers may be substantially 0. In the case of a seal enclosed within the layers then permanent set is preferably in the range comparable to Allevyn dressings.

Tensile Strength

In the case of a seal enclosed within the layers the composition benefits from the support of the dressing and tensile strength values may be widely variable. In the case of a seal enclosed within the layers then tensile strength is preferably in the range comparable to Allevyn dressings.

Elongation at Break

In the case of a seal enclosed within the layers the composition benefits from the support of the dressing and elongation at break values may be widely variable. In the case of a seal enclosed within the layers then elongation at break is preferably in the range comparable to the spacer materials typically present in dressings. Spacer elongation at break is 115%. Preferably elongation at break is in the range 5-15%.

Compressibility

Preferably the composition forms a seal having equal or greater compressibility than the bridging layer. Further detail is given herein in relation to preferred compressibility of the bridging layer and bridging layer materials when subject to negative pressure. Preferably a seal does not protrude above the exposed portion which is seals, preferably a protruding seal is compressible. Compressibility is measured according to penetrometry ASTM 82137, more preferably is in the range 20-500/10 mm.

It will be clear that viscosity for each of Parts A and B is for the as-provided components, prior to mixing. Suitably the components mix to a dispensible viscosity.

Preferably the cured composition has elongation at break as hereinbelow defined, greater than or equal to 50%.

Preferably the cured composition has tensile strength, as hereinbelow defined, greater than or equal to 5 kgfcm$^{-2}$.

Preferably for the cured composition permanent set is in the range 20% to 0%.

Figure 7A:
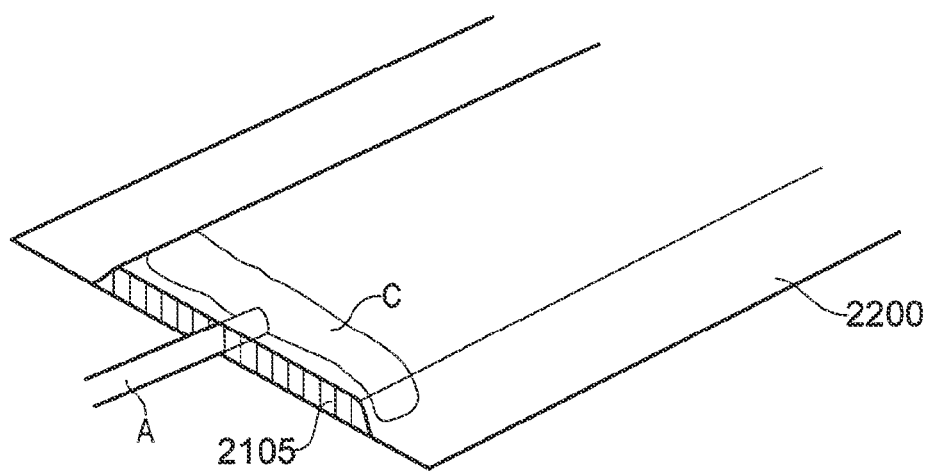

Preferably the composition is a Silpuran composition as hereinabove recited, more preferably is Silpuran 2400™, or a functional analogue thereof, optionally incorporating viscosity and/or cure time modifier providing increased viscosity and reduced cure time. Preferably the composition has translucent appearance after curing. Preferably the composition is dispensed within the transmission layer by the first embodiment method disclosed herein (FIG. 7A).

In a first embodiment the composition is dispensing into a location as hereinbefore defined, the location being substantially internal to or received within the transmission layer at the exposed portion as hereinbefore defined. In this embodiment, composition is required to be dispensed from an outlet of a dispensing device such as a static mixer, said outlet being capable of being received within the transmission layer at the exposed portion as hereinbefore defined. Suitably a dispenser comprises a syringe or static mixer comprising a nozzle having an outlet. Preferably the nozzle is capable of being received within the transmission layer at the exposed portion in manner that the location at which composition is to be dispensed is a short distance within the exposed portion, for example is up to 25 mm distant from the exposed portion, more preferably from 2 mm to 20 mm, more preferably from 3 mm to 18 mm, for example in the range from 5 mm to 12 mm. Composition may be dispensed via the exposed portion face or via the backing layer or sheet, for example by injection through the backing layer or sheet. Dispensing may be before or after trimming a dressing. Dispensing by this means may be by puncturing the film either singly or in multiple places as described above. Preferably the film is punctured with use of one or more resiliently deformable needles, for example a plastic needle or with use of one or more limited penetration depth needles. Such needle minimizes risk of skin puncture. Alternatively the injection could take place prior to dressing placement and removal of the dressing handle, thus confining the sealant to between the backing layer or sheet and the handle. Dispensing may be prior to trimming the dressing alongside or through the cured sealant to leave a sealed edge. Composition may alternatively be dispensed to intact skin and exposed portion of the dressing located thereover. Composition so dispensed flows into or is drawn into the dressing to the transmission layer thereby sealing.

Composition so dispensed is dispensed to a location deeper into the exposed portion distanced from its face. Composition is dispensed as a band returning back to the face of the exposed portion as the dispensing device is withdrawn. A seal so generated is more secure, with more comprehensive blocking of passageways within the exposed portion of the transmission layer. Such a seal has a lesser likelihood of presenting leaks when negative pressure is applied. A suitable nozzle for a dispensing device includes low aperture nozzles, needles and the like. Nozzles may be formed from plastic. Such nozzles are disposable and present no hazard, being non-perforating to human skin. Such nozzles are currently available for use with pipette tips.

Composition may be dispensed via multiple point injection at intervals along the exposed face, for example through the spaces between the spacer layer struts. Composition may flow to some extent on initial application, either or both laterally to the direction of dispensing and advancing and receding, flow becoming less as composition hardens or cures. This may aid in providing a continuous lateral seal, whereby dispensing intervals along the face of exposed portion may be increased. Nozzle insertion distance within the exposed portion may be selected to confine the seal spaced a short distance in from the face of the exposed portion, or to allow some spill of composition out of the exposed portion and onto surrounding surfaces such as a preparation plate or skin. Advantages of this embodiment include minimizing the amount of composition required to be dispensed. This in turn allows use of a lower capacity dispensing device, for example a 5 ml or 10 ml or 15 ml or 25 ml syringe or static mixer. The back pressure encountered on dispensing from a static mixer increases with the mixer volume, which in turn leads to a decrease in the viscosity which the static mixer is able to dispense. It is generally advantageous to this embodiment to deliver composition at as high a viscosity as possible to ensure that composition is confined within the exposed portion. A further element in the total back pressure or resistance encountered on dispensing composition is the nozzle aperture of static mixer. For this embodiment, it is desired to dispense composition from a small aperture nozzle, and this adds to the back pressure. The advantage that this embodiment delivers of enabling a relatively small volume syringe or mixer to be employed, allows greater freedom to operate a small aperture nozzle.

Finally we have found that a seal generated by dispensing composition internally to the exposed portion according to this embodiment, is highly effective. The dressing should be trimmed, as hereinbefore described, such that the exposed portion overlies intact skin about a wound, and does not overly the wound itself. In the case of a dressing having an adhesive or tacky wound contact layer, such as a silicone contact layer as hereinbefore described, the wound contact layer adheres to the skin about the wound and seals the dressing to skin about the exposed portion and the dispensed seal. Preferably the exposed portion is bordered by a border region at the 2 extremities thereof, for example a border of backing sheet or layer as hereinbefore defined, preferably having depth in the range 5 mm to 25 mm, more preferably 7 mm to 25 mm, for example 14 mm to 25 mm. The wound contact layer is perforated or otherwise porous to allow transmission of fluids to and from the wound bed, and this may permit flow of composition onto skin directly proximal to the internal seal. This may beneficially enhance the seal between the wound contact layer and skin. In the event that flow of composition to skin directly proximal to the internal seal is not desired, composition suitably has a sufficiently high viscosity to restrict flow, alternatively the wound contact layer may be non-porous or non-permeable in the region proximal to an envisaged exposed portion, for example at a bridging portion or trimmable portion as hereinbefore defined. Composition may be dispensed to a location as hereinbefore defined in a dressing having no obscuring layer, or having window(s) in obscuring layer at bridging portions or trimmable portion(s). This allows visual control of nozzle insertion distance within the exposed portion of composition, of volume dispensed, and/or of lateral flow enabling a suitable dispensing interval across the face of exposed portion to be determined. In the case that no obscuring layer is present it is preferred that the composition incorporates ADL as hereinbefore defined as transmission layer, rather than spacer layer which may pose a risk of penetrating the backing sheet.

In this embodiment preferably the dressing does rot comprise absorbent layer such as ADL in the bridging portion or at the trimmable portion.

In a further embodiment of the composition for dispensing into a location as hereinbefore defined, the location comprises the backing layer or backing sheet adjacent the exposed portion, whereby composition flows across and covers the exposed portion. In some cases composition flows a short distance into or is drawn a short distance within the exposed portion. It may be desired to dispense or smooth composition at the perimeters or extremities of the exposed portion for example adjoining a border region, and for example directed slightly back along the perimeter or extremity. This has the advantage of advancing composition a short distance at the perimeter of the exposed portion, ensuring a total seal and also securing the seal in place. As composition hardens or cures, the viscosity typically increases and flow ceases whereby composition is retained at or in the dispensing location and forms an effective seal.

This further embodiment places performance requirements on the composition and the resulting seal, additional to those of the first embodiment of sealing and mode of dispensing. Specifically composition requires a continuous film to be dispensed and formed across the surface of the backing layer or sheet bridging onto the exposed portion of any additional layers and the exposed portion of the transmission layer and bridging onto the skin surface. Therefore composition must be sufficiently viscous and/or cohesive to form an intact film. Such film may be thin or may be of appreciable depth and/or thickness of for example from the order of depth and/or thickness of the backing sheet to the order of depth and/or thickness of the dressing or of the component layers at the exposed portion thereof, for example 1 mm to 5 mm. Should such film rupture or fail prior to setting or curing of composition then the seal will fail. After setting or curing of an intact film, the exposed nature of the seal and its presentation as a film place additional requirements of robustness, both to external influences and also, to its ability to retain integrity across interfaces between adjacent layers. These requirements are likely to be greater in the case of a thin film. Preferably therefore a seal according to this further embodiment is characterized by properties of tensile strength, permanent set, and elongation at break, optionally also extensibility, in ranges as hereinbefore defined. In contrast a seal generated according to the first embodiment, as hereinabove, is supported in large part by the fabric of the dressing enclosing the seal, whereby requirements of tensile strength, permanent set, elongation at break, are significantly lower, also being enclosed within the lower extensibility dressing, the requirement for extensibility is significantly lower than for the further embodiment as herein.

A seal according to this embodiment may be effective from the backing layer surface across the exposed portion. As will be apparent, a seal across the exposed portion alone is susceptible to failure at the interface of the backing sheet and exposed portion and any intervening layers.

This further embodiment is likely to be more effective when adopted in relation to a dressing comprising no additional layers as hereinbefore defined, thereby better resisting strains introduced by separation at the interface of additional layer(s) and transmission layer. Additional layer(s) if present may beneficially be secured at their interfaces with each other and with transmission layer, by needling, stitching and other means as known in the art.

The further embodiment moreover requires that a seal have low profile and/or have compressibility greater than or equal to the surrounding dressing. This is of advantage in minimizing discomfort to the wearer imposed by a protruding ridge at the exposed portion of the dressing.

In one embodiment the composition may comprise any polymers that follow a hydrosilylation reaction. One polymer (i) preferably contains alkenyl groups, the other (ii) preferably contains Si—H moieties. The group of siloxane polymers is based on a structure comprising alternate silicon and oxygen atoms with various organic moieties attached to the silicon. Curing can be defined as a treatment that decreases the flow of an elastomer. This change is generally brought about by linking reactions between polymer molecules. Where the silicon hydride (Si—H) moiety is part of a polysiloxane, it is possible for the alkenyl group to either be part of a siloxane polymer or otherwise part of a non-siloxane polymer. The position of the alkenyl functional group is not critical and it may be either at the molecular chain terminals or in non-terminal positions along the molecular chain.

A curing system is preferably apportioned between at least one Part A and at least one Part B and comprises: one or more alkenyl-group containing polymers (i) having at least one alkenyl group or moiety per molecule, one or more SiH-containing polymers (ii) having at least one Si—H unit per molecule; and a catalyst (iii) for curing by addition of alkenyl-containing polymer (i) to SiH-containing polymer (ii).

A "unit" as herein referred represents a group or moiety or part thereof. A "moiety" as herein referred is a group of atoms having further atoms disposed on two or more sides thereabout, ie having two or more valencies unspecified.

A "group" as herein referred represents a group of atoms having further atoms disposed on one side thereof, ie having one valency unspecified. Si—H units herein have the same meaning as SiH units.

Polymers (i) and (ii) as hereinbefore defined are fluid-phase polymers incorporating reactive groups which cross-link in presence of catalyst to form a copolymer more preferably a cured elastomer. Suitably Part A comprises catalyst together with polymer (i), and Part B comprises polymer (ii) optionally together with any remaining polymer (i). Suitably polymers, catalyst and optional further components are apportioned in manner to balance volumes and viscosities of both Parts. Preferably polymer (i) is an alkenylsiloxane-containing polymer.

Preferably the Parts are combined and intimately admixed prior to or during to dispensing.

Suitably the components and Parts mix to a dispensible viscosity.

Polymers (i) and/or (ii) are commercially available or may be obtained by known techniques. Suitably polymers (i) and/or (ii) are independently selected from known and novel fluid phase homopolymeric, and copolymeric polymers, and their entangled systems and mixtures thereof. The compositions, in turn, cure to form copolymers, and may also include their entangled systems and mixtures with other non-reactive polymers if present in the composition.

Copolymeric polymers include all hybrids derived from two or more monomeric species, including alternating, periodic, statistical, random, block, linear, branched, star, graft and pendant copolymers. Entangled systems include interpenetrating networks (IPNs) and semi-interpenetrating networks (SIPNs). It is also the case that these polymers can incorporate both organic and inorganic moieties.

Preferably polymers (i) and (ii) are selected from silicones, including siloxanes and modified siloxanes, polyurethanes (PU) including polyester and polyether urethanes, elastomeric polyether polyesters, polyglycolic acid, polyacetates such as ethyl vinyl acetate, polyacrylate, polyacid derivatives of polysaccharides, such as carboxyalkylcellulose, carboxyalkylchitosan and copolymers thereof, and their hybrids including copolymers, entangled systems and mixtures thereof.

The composition may make use of an addition cure reaction between organohydrogensiloxane units and organoalkenylsiloxane units. These units may be incorporated into a wide range of polymeric, copolymeric, entangled and mixed polymers as hereinbefore defined. Preferred siloxane polymers (i) and (ii) therefore include these respective units and are more preferably polyorganosiloxanes. Polymer (i) is preferably a polydiorganosiloxane polymer comprising alkenyl-containing units, more preferably is a polydiorganoalkenylsiloxane polymer. Preferably polymer (ii) is a polydiorganosiloxane polymer comprising SiH units, more preferably is a polydiorganohydrogensiloxane polymer.

Examples of hybrid organic-inorganic polymeric systems that have used both siloxane and organic units include: acrylate functionalized siloxane copolymers, which have found use in contact lenses (U.S. Pat. No. 3,808,178); hybrid grafts where organic polymers are grafted onto a polysiloxane chain or where siloxanes are grafted onto organic polymers, for example in silane graft technology for cross linkable HDPE (U.S. Pat. No. 3,646,155) where hybrid grafts have been used to allow the cross linking of organic polymers through siloxane bond formation; hybrid block copolymers for example silicone-polycarbonate block copolymers (U.S. Pat. No. 3,274,155); and copolymers of hybrids of silicone and ethylene copolymers, cross-linked with vinyl-containing silicone copolymers which have found use in coating textiles (US 2005/0100692);

IPNs represent a special class of hybrid polymeric systems, these systems use a combination of mechanical entanglement and crosslinking in which one polymer is cured about another; these include thermoplastics entangled with platinum catalyzed addition cure silicones such as silicone-urethane IPNs and semi-IPNs including silicone-urethane and silicone-polyamide systems which are of general application or have found specific use in coating textiles (U.S. Pat. Nos. 4,714,739, 7,543,843); hydrophilic components immobilised in a silicone polymer (U.S. Pat. No. 5,397,848) which have found use as contact lens material; and silicone polymer cured about a non-reactive polymer of comparable adhesion, which have found use in coating textiles (U.S. Pat. No. 7,132,170).

Polymers may also be selected from modified silicones (MS) which find use as adhesives in catheter tubing and the like.

Preferred compositions comprise a polydiorganosiloxane polymer (i) and/or (ii) and/or their respective combinations with the aforementioned polymers. A composition in which polymers comprise or consist essentially of polydiorganosiloxane polymers (i) and (ii) has particular advantages, for example in applications where low toxicity is an advantage, preferably in medical or dental applications or in non-medical or non-dental applications requiring low toxicity or favorable biocompatibility.

Alternatively or additionally polymers (i) and (ii) are as commercially available (Cavi-Care™ A/B, and the like) or variants thereof, optimised for viscosity and curing to give a fluid-tight exposed surface (hereinafter skin-formation or "skinning") as hereinbefore defined.

Polymer (i) and (ii) may comprise respective alkenyl-containing units and organohydrogensiloxane units situated along the length of polymer chains, and/or as polymer chain end-capping units or a combination thereof. Polymer (i) in-chain and end-capping alkenyl units preferably comprise alkenyl group or moiety $R^{Alk}$ selected from $C_{2-20}$ alkenyl optionally substituted or including one or more aryl groups or moieties. $R^{Alk}$ may comprise terminal or non terminal unsaturation, and may be of the formula i-I:

$$—R^{Alk1}—CR^{Alk1}{=}CR^{Alk2}{}_2 \qquad \text{(i-I)}$$

in which the groups $R^{Alk1}$ and $R^{Alk2}$ are independently selected from H, $C_{1-20}$ alkyl and $C_{5-20}$ aryl groups and combinations thereof and a moiety $R^{Alk1}$ is selected from a single bond, $C_{1-20}$ alkyl and $C_{5-20}$ aryl groups and combinations thereof. One of $R^{Alk2}$ may be a moiety linking to polymer chain. More preferably each $R^{Alk}$ is independently selected from vinyl, allyl, propenyl, and from terminally and non-terminally unsaturated butenyl, pentenyl, hexenyl, heptenyl, octenyl, nonenyl and decenyl groups, most preferably selected from vinyl and hexenyl groups.

Preferably polymer (i) comprises a polydiorganosiloxane polymer or copolymer comprising alkenyl-containing units of the formula (i-II):

$$\equiv Si—R^{Alk}, \qquad \text{(i-II)}$$

more particularly of the formula (i-III) and/or (i-IV):

$$—O—SiR^1R^{Alk}—O— \qquad \text{(i-III)}$$

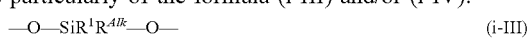
$$—O—SiR^1{}_2R^{Alk} \qquad \text{(i-IV)}$$

wherein $R^{Alk}$ is as hereinbefore defined and one or more groups $R^1$ are organo groups suitably independently selected from alkyl and aryl groups, more preferably $C_{1-20}$ alkyl and $C_{5-20}$ aryl groups and combinations thereof, for example from methyl, ethyl, propyl, butyl, pentyl, hexyl, heptyl, octyl, nonyl and/or decyl groups and moieties.

More particularly polymer (i) is selected from the formula i-V and i-VI:

$$P^i—O—SiR^1R^{Alk}—O—P^i \qquad \text{i-V:}$$

$$P^i—O—SiR^1{}_2R^{Alk} \qquad \text{i-VI}$$

wherein $P^i$ denotes the remainder of the polymer chain which may incorporate same or different units, and $R^1$ is as hereinbefore defined.

Polymer (i) may also comprise a polyorganosiloxane exhibiting, per molecule, at least two $C_2$-$C_6$ alkenyl groups bonded to the silicon and having, for example, a viscosity of between 10 and 300000 mPa·s, that is to say 0.01 to 300 Pa·s, such that when combined in Part A with further Part A components and optionally additionally in Part B with further Part B components, Part A, and Part B as appropriate, is (are) of viscosity in a range as hereinbefore defined, which can in particular be formed of at least two siloxyl units of formula:

$$Y_d R_e SiO_{\frac{(4-d-e)}{2}} \qquad \text{(III)}$$

in which:
Y is a $C_2$-$C_6$ alkenyl such as vinyl, allyl or hexenyl groups, preferably vinyl,
R is a monovalent hydrocarbon group with no unfavorable effect on the activity of the catalyst which is generally chosen from alkyl groups having from 1 to 8 carbon atoms inclusive, such as the methyl, ethyl, propyl and 3,3,3-trifluoropropyl groups, cycloalkyl groups, such as the cyclohexyl, cycloheptyl and cyclooctyl groups, and aryl groups, such as xylyl, tolyl and phenyl,
d is 1 or 2, e is 0, 1 or 2 and d+e=1, 2 or 3,
optionally all the other units being units of average formula:

$$R_f SiO_{\frac{4-f}{2}} \qquad (IV)$$

in which R has the same meaning as above and f=0, 1, 2 or 3.

Examples of polymer (i) are, for example, dimethylpolysiloxanes comprising dimethylvinylsilyl ends, (methylvinyl)(dimethyl)polysiloxane copolymers comprising trimethylsilyl ends or (methylvinyl)(dimethyl)polysiloxane copolymers comprising dimethylvinylsilyl ends.

A convention accepted in the art for denoting the units of silicones according to the number of oxygen atoms bonded to the silicon is used here. This convention uses the letters M, D, T and Q (abbreviations for "mono", "di", "tri" and "quatro") to denote this number of oxygen atoms. This nomenclature of silicones is described, for example, in the work by Walter Noll, "Chemistry and Technology of Silicones", Academic Press, 1968, 2nd edition, on pages 1 to 9.

Polymer (i) may also be a silicone resin bearing at least two alkenyl, preferably vinyl groups. Such silicone resin comprising at least two different siloxane units chosen from those of M siloxane unit of formula $R_3SiO_{1/2}$, D siloxane unit of formula $R_2SiO_{2/2}$, T siloxane unit of formula $RSiO_{3/2}$ and Q siloxane unit of formula $SiO_{4/2}$,
wherein R denotes a monovalent hydrocarbon group, with the conditions that at least one of these siloxane units being a T or Q siloxane unit and that at least two of the M, D and T siloxane units comprises an alkenyl group.

The silicone resin could be selected from the group consisting of:
an organopolysiloxane resin of formula $MT^{Vi}Q$ consisting essentially of:
(a) trivalent siloxane units $T^{Vi}$ of the formula $R'SiO_{3/2}$;
(b) monovalent siloxane units M of the formula $R_3SiO_{1/2}$, and
(c) tetravalent siloxane units Q of the formula $SiO_{4/2}$
an organopolysiloxane resin of formula $MD^{Vi}Q$ consisting essentially of:
(a) divalent siloxane units $D^{Vi}$ of the formula $RR'SiO_{2/2}$;
(b) monovalent siloxane units M of the formula $R_3SiO_{1/2}$, and
(c) tetravalent siloxane units Q of the formula $SiO_{4/2}$
an organopolysiloxane resin of formula $MDD^{Vi}Q$ consisting essentially of:
(a) divalent siloxane units $D^{Vi}$ of the formula $RR'SiO_{2/2}$;
(b) divalent siloxane units D of the formula $R_2SiO_{2/2}$
(b) monovalent siloxane units M of the formula $R_3SiO_{1/2}$, and
(c) tetravalent siloxane units Q of the formula $SiO_{4/2}$
an organopolysiloxane resin of formula $M^{Vi}Q$ consisting essentially of:
(a) monovalent siloxane units $M^{Vi}$ of the formula $R'R_2SiO_{1/2}$; and
(b) tetravalent siloxane units Q of the formula $SiO_{4/2}$, and
an organopolysiloxane resin of formula $M^{Vi}T^{Vi}Q$ consisting essentially of:
(a) monovalent siloxane units $M^{Vi}$ of the formula $R'R_2SiO_{1/2}$;
(b) trivalent siloxane units $T^{Vi}$ of the formula $R'SiO_{3/2}$, and
(c) tetravalent siloxane units Q of the formula $SiO_{4/2}$
wherein R denotes a monovalent hydrocarbon group such as methyl and R' denotes a vinyl group:

Such resins are well-known branched organopolysiloxane oligomers or polymers which are commercially available.

They are provided in the form of solutions, preferably siloxane solutions.

Polymer (ii) in-chain and end-capping polyorganohydrogensiloxane units are preferably selected from the formula ii-I and ii-II:

$$—O—SiR^2H—O— \qquad \text{ii-I}$$

$$—O—SiR^{22}H, \qquad \text{ii-II}$$

more preferably polymer (ii) is selected from formula ii-III and ii-IV:

$$P^{ii}—O—SiR^2H—O—P^{ii} \qquad \text{ii-III}$$

$$P^{ii}—O—SiR^{22}H \qquad \text{ii-IV}$$

wherein
$P^{ii}$ denotes the remainder of the polymer chain which may incorporate same or different units and one or more groups $R^2$ are organo groups suitably independently selected from $C_{1-20}$ alkyl, $C_{5-20}$ aryl and combinations thereof, for example from methyl, ethyl, propyl, butyl, pentyl, hexyl, heptyl, octyl, nonyl and/or decyl groups.

Polymer (ii) preferably comprises a polyorganohydrogensiloxane—polydiorganosiloxane copolymer, incorporating one or more units ii-I and/or ii-II:

$$—O—SiR^2H—O— \qquad \text{ii-I}$$

$$—O—SiR^{22}H \qquad \text{ii-II}$$

and one or more units ii-V and/or ii-VI:

$$—O—SiR_{22}—O— \qquad \text{ii-V}$$

$$—O—SiR^{23} \qquad \text{ii-VI}$$

wherein $R^2$ is as hereinbefore defined, more preferably copolymer incorporating polyorganohydrogensiloxane end-capping units, i.e polymer chains terminate with the group or moiety ii-VII:

$$≡Si—H, \qquad \text{ii-VII}$$

more particularly with the unit of formula ii-II:

$$—O—SiR^{22}H \qquad \text{ii-II}$$

as hereinbefore defined. Most preferably polymer (ii) comprises methylhydrogensiloxane-dimethylsiloxane copolymers.

Polymer (ii) may also comprises a polyorganosiloxane, exhibiting, per molecule, at least two hydrogen atoms bonded to the silicon and preferably at least three ≡SiH units and having, for example, a viscosity of between 1 and 5000 mPa·s, that is to say between 0.001 and 5 Pa·s, up to 300 Pa·s as hereinbefore defined, such that when combined in Part B with further Part B components, Part B is of viscosity in a range as hereinbefore defined, which can in particular be formed of siloxyl units of formula:

in which:
- X is a monovalent hydrocarbon group with no unfavorable effect on the activity of the catalyst which is generally chosen from alkyl groups having from 1 to 8 carbon atoms inclusive, such as the methyl, ethyl, propyl and 3,3,3-trifluoropropyl groups, cycloalkyl groups, such as the cyclohexyl, cycloheptyl and cyclooctyl groups, and aryl groups, such as xylyl, tolyl and phenyl,
- g=1 or 2, preferably=1, i=0, 1 or 2 and g+i=1, 2 or 3, optionally all the other units being units of average formula:

in which X has the same meaning as above and j=0, 1, 2 or 3.

Examples of polymer (ii) are polymethylhydrosiloxanes or methylhydrodimethylsiloxane copolymers.

In the case that polymers include other units additional to iIII, iIV, iiI and iiII for example, these are suitably not reactive with the respective polymer at ambient temperature or under sterilising conditions.

Suitably the ratio of silicon-bonded hydrogen atoms provided by (ii) to silicon-bonded alkenyl moieties provided by (i) is at least 0.5:1, preferably 1:1.

Preferably embodiments of the curable composition follow the catalysed addition cure reaction according to the following scheme:

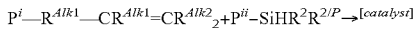

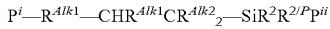

more preferably:

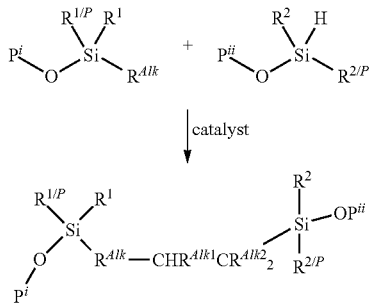

wherein integers are as hereinbefore defined and $R^{1/P}$ is selected from $P^i$ and $R^1$ as hereinbefore defined and $R^{2/P}$ is selected from $P^{ii}$ and $R^2$ as hereinbefore defined.

The polymers (i) and (ii) and catalyst (iii) may be apportioned in at least one Part A and at least one Part B in manner to provide respective Parts A and B which in isolation are not reactive at ambient temperature, nor under sterilisation conditions, such as heat or radiation. Apportioning may also be determined according to volume and viscosity.

Polymers (i) and (ii) and catalyst (iii) may be apportioned in at least one Part A and at least one Part B in manner such that polymer (ii) is absent from Part A and polymer (i) is absent from Part B or Part B incorporates a trace amount of polymer (i) represented as molar ratio (Si—H unit or moiety)/(alkenyl unit or moiety) of greater than or equal to 2000. Such composition may be sterilised at effective gamma or radiation dose for example as disclosed in WO2012/069794, the contents of which are incorporated herein by reference.

The at least one Part A and at least one Part B may be of substantially equal volume and viscosity or of different volume and/or viscosity. Part A or Part B may incorporate a suitable viscosity moderator or diluent, in amount to increase or reduce volume and/or viscosity. By this means Part A and Part B having different volume and viscosity may be volume and viscosity matched for improved ease and intimacy of mixing and dispensing. A suitable diluent is for example a silicone oil which is available in any desired viscosity for thickening or thinning effect. Alternatively or additionally at least one Part A and at least one Part B are sealed in respective receptacles or on respective supports which are thermally stable at an elevated temperature of 121° C. or more for a period of up to 28 hours, for example as disclosed in WO2012/069793, the contents of which are incorporated herein by reference.

The composition may thereby be rendered terminally sterile by being sterilised in its primary packaging and this property may be characterised by a Sterility Assurance Level (SAL). The SAL is defined in ISO 11139:2006 as the probability of a single viable microorganism occurring on an item after sterilization. The term SAL takes a quantitative value, in the format of $10^{-n}$, where typically n=3, 4, 5 or 6, preferably SAL=$10^{-3}$ or $10^{-6}$.

A catalyst as hereinbefore defined may be any catalyst which is effective in catalysing the addition curing reaction as hereinbefore defined, more preferably as hereinabove illustrated. Suitable catalysts are selected from any known form of platinum, rhodium, palladium, nickel and like addition curing hydrosilylation catalysts, for example as disclosed in U.S. Pat. No. 5,153,231, US 2006/0217016, U.S. Pat. Nos. 3,928,629 and 4,529,553 the contents of which are incorporated herein by reference.

A platinum catalyst may be selected from platinum black platinum as deposited on carriers including silica such as silica gel or carbon such as powdered charcoal, platinic chloride or chloroplatinic acid and alcohol solutions thereof, salts of platinic and chloroplatinic acids and platinum complexes such as platinum/olefin, platinum/alkenylsiloxane, platinum/beta-diketone, platinum/phosphine and the like. Chloroplatinic acid may be the hexahydrate or anhydrous form. A platinum complex may be prepared from chloroplatinic acid and its hexahydrate, or from platinous chloride, platinum dichloride, platinum tetrachloride and their neutralised complexes with divinyltetramethyldisiloxane, optionally diluted with dimethylvinylsiloxy endcapped polydimethylsiloxane.

A palladium catalyst may be selected from palladium on carbon, palladium chloride and the like.

A rhodium catalyst may be selected from rhodium chloride and one or more complexes of rhodium having the general formula iii-I or iii-II:

wherein each X represents a halogen atom and each R represents an alkyl or aryl radical or combination thereof having from 1 to 8 inclusive carbon atoms or the R'$_3$SiQ group in which Q represents a divalent aliphatic hydrocarbon radical having from 1 to 6 inclusive carbon atoms and R' represents an alkyl or aryl radical or combination thereof having from 1 to 8 inclusive carbon atoms or a (CH$_3$)$_3$Si—group, not more than one R' per molecule being (CH$_3$)$_3$Si—. For example rhodium chloride/di(n-butyl)sulfide complex and the like.

A nickel catalyst is preferably a zero valent nickel selected from M$_2$Ni$^{(0)}$ such as bis(1,5-cyclo-octadienyl) nickel (Ni(COD)$_2$) and from MNi$^{(0)}$G wherein M is a bidentate alkene cyclic hydrocarbon ring of C$_{8-12}$ and G is selected from monodentate and bidentate phosphorous groups having hydrogen atoms, substituted or unsubstituted hydrocarbon radicals or mixtures thereof bonded to the phosphorous atoms of the phosphorous groups.

The composition may include a catalyst inhibitor. Suitable inhibitors are known in the art. For example a catalyst inhibitor may be selected from a polymethylvinylsiloxane cyclic compound and an acetylenic alcohol, such as methyl butynol for example as in Cavi-Care or disclosed in U.S. Pat. No. 5,153,231, the contents of which are incorporated herein by reference.

Preferably the composition comprises an addition-reaction retardant or a crosslinking inhibitor chosen, for example, from the following compounds:
polyorganosiloxanes substituted with at least one alkenyl that may optionally be in cyclic form, tetramethylvinyltetrasiloxane being particularly preferred,
organic phosphines and phosphites,
unsaturated amides,
alkyl maleates, and
acetylenic alcohols.

These acetylenic alcohols (see FR-A-1 528 464 and FR-A-2 372 874), which are among the preferred thermal blockers of the hydrosilylation reaction, have the formula:

(R')(R")C(OH)—C≡CH in which formula
R' is a linear or branched alkyl radical, or a phenyl radical;
R" is H or a linear or branched alkyl radical, or a phenyl radical; the radicals R', R" and the carbon atom alpha to the triple bond possibly forming a ring; and
the total number of carbon atoms contained in R' and R" being at least 5 and preferably from 9 to 20.
Examples that may be mentioned include:
1-ethynyl-1-cyclohexanol;
3-methyl-1-dodecyn-3-ol;
3,7,11-trimethyl-1-dodecyn-3-ol;
1,1-diphenyl-2-propyn-1-ol;
3-ethyl-6-ethyl-1-nonyn-3-ol;
2-methyl-3-butyn-2-ol;
3-methyl-1-pentadecyn-3-ol.

These α-acetylenic alcohols are commercial products. Such a retardant is present in a maximum proportion of 3000 ppm relative to the total weight of the polyorganosiloxanes in the silicone composition. Methyl butynol could be chosen as in Cavi-Care.

The composition may be non-foamable or may be foamable, comprising (iv) an expansion or "blowing" agent, selected from any agent which evolves gas or vapour as part of or during the curing reaction, for example selected from H-donors, OH-containing agents, H-bonding agents such as:
alcohols including methanol, ethanol, n-propanol, isopropanol, n-butanol, 2-butanol, tert-butanol, n-hexanol, n-octanol and benzyl alcohol. n-Propanol, n-butanol, n-hexanol and n-octanol are particularly preferred,
polyols such as diols including, 4-butanediol, 1,5-pentanediol and 1,7 heptanediol,
silane or polysilane having at least one silanol group, or water.

The composition forms, after hydrosilylation, a silicone elastomer which may be foamed or have gel properties. A foamed composition does not transmit air through the body of the foam or through the foam surface or both, for example incorporates cells closed either by chemical or mechanical means. The term "silicone gel" denotes a crosslinked silicone product characterized by a degree of penetration of, for example, between 20 and 500 tenths of a mm (measured by ASTM D 2137 penetrometry, weight of the rod and of the cone: 62.5 g).

When the composition is prepared for a silicone gel it may have at least one nonfunctionalized polyorganosiloxane comprising:
a) end siloxyl units of type M=(R$^6$)$_3$SiO$_{1/2}$
in which the R$^6$ radicals which are identical or different, correspond to an optionally substituted linear or branched C1-C$_6$ alkyl group and/or a substituted or unsubstituted aryl group, and
b) identical or different siloxyl units of type D=(R$^7$)$_2$SiO$_{2/2}$ in which the R$^7$ radicals correspond to the same definition as R$^6$.

The physical properties of these gels are adjusted according to the use by varying the levels of siloxyl units carrying Si-alkenyl and SiH functional groups and when it is present by varying the percentage by weight of nonfunctionalized polyorganosiloxane, which is well known in the prior art.

To enhance the adhesive properties of a silicone gel, the composition may further comprise a monofunctional polyorganosiloxane carrying a single Si-alkenyl group per molecule as taught by European patent application EP-1633830-A2.

Further, a composition may also comprise inorganic filler such as reinforcing or bulking fillers. These fillers can be provided in the form of very finely divided products, the mean particle diameter of which is less than 0.1 µm. These fillers include in particular fumed silicas and precipitated silicas; their specific surface is generally greater than 10 m$^2$/g and generally lies within the range 20-300 m$^2$/g.

These fillers can also be provided in the form of more coarsely divided products, with a mean particle diameter of greater than 0.1 µm. Mention may in particular be made, as examples of such fillers, of ground quartz, calcium carbonate, diatomaceous silicas, calcined clay, titanium oxide of the rutile type, iron, zinc, chromium, zirconium or magnesium oxides, the various forms of alumina (hydrated or nonhydrated), boron nitride, lithopone or barium metaborate; their specific surfaces are generally less than 30 m$^2$/g.

The filler may have a hydrophobic surface, which may be obtained by treating the filler, e.g. with suitable silanes, short chain siloxanes, fatty acids or resinous silicone materials.

Hexamethyldisilazane treated fumed silica may be considered, or if translucence is to be maintained, vinyl "Q" reinforcing resins may be used. A filler may be hydroplobic. Suitable materials and processes for rendering the surface of fillers hydrophobic have been described in the literature, and are known to the person skilled in the art. The fillers can also be composed of a mixture of several types of fillers with different particle sizes.

The composition may comprise a thixotropic agent. A thixotropic agent confers on a composition properties whereby it becomes viscous during application and reverts to higher viscosity after application when no longer being worked. Thixotropes include fillers such as silica, and certain silicone-based substances.

A composition may include additional components including other adjuvants, preservatives including propyl gallate, extenders, rheology regulators, adhesion promoters or adhesion reducers, moisture vapor permeability (MVP) or moisture vapor transmission rate (MVTR) promoters to prevent maceration of skin having composition applied thereto, whereby skin can transpire and pass liquid but still function as a sealant and bacterial barrier, and the like. Suitably such additional components confer properties as hereinbefore defined on the composition.

The composition may comprise active agents, which may have any desired activity for the intended purpose, and include active pharmaceutical ingredients (API's) and the like.

Antimicrobial agents, biocides and disinfectants may be selected from silver, in particular nano crystalline silver, and derivatives including silver complexes and salts such as ionic silvers, silver zeolite, silver oxide, silver nitrate, silver acetate, silver chloride, silver sulphadiazine), biguanides including polyhexamethylene biguanide, chlorhexidine digluconate and its acetate salts chlorhexidine acetate and diacetate, manuka honey, peroxides (e.g. hydrogen peroxide), iodine (e.g. povidone iodine), sodium hypochlorite, copper, copper complexes; zinc (e.g. zinc oxide, zinc pyrithione), gold, gold complexes; phosphates, amines, amides and sulphonamides (e.g. hexatidine, proflavine. mafenide, nitrofurazone, norfloxacin); antibiotics (e.g. gentamicin, bacitracin, rifampicin; alcohols and acids (e.g. ethanol, phenoxy ethanol, mupirocin).

Nutrients, pain killers and other pain management techniques suitably include analgesics and anasthetics and may be selected from amethocaine, lignocaine, non-steroidal anti-inflammatory drugs, anti inflammatories such as hydrocortisone, paraffin to reduce adherence to the skin, urea to reduce dehydration of the skin; buffering components to promote healing of the skin.

Heamostats may be selected from chitin, chitosan, kaolin; antifibrinolytics such as amino acids, aminocaproic acid, tranexamic acid, aminomethylbenzoic acid; Proteinase inhibitors including aprotinin, alfal antitrypsin, C1-inhibitor, camostat; Vitamin K and other hemostatics including vitamin K, phytomenadione, menadione; fibrinogen including human fibrinogen; local hemostatics including absorbable gelatin sponge, oxidized cellulose, tetragalacturonic acid hydroxymethylester, adrenalone, thrombin, collagen, calcium alginate, epinephrine; blood coagulation factors including coagulation factor IX, II, VII and X in combination, coagulation factor VIII, factor VIII inhibitor bypassing activity, coagulation factor IX, coagulation factor VII, von Willebrand factor and coagulation factor VIII in combination, coagulation factor XIII, eptacog alfa (activated), nonacog alfa, thrombin and systemic hemostatics: etamsylate, carbazochrome, batroxobin romiplostim, eltrombopag.

Active agents may further include combination materials including superabsorbers, odour management agents, wovens and non wovens, gellable fibres; growth factors, wound debridements—mechanical, autolytic and enzymatic; resorbable dressings and micro structure to influence cell ingrowth; cells, tissue (e.g. autologous treatments); indicators; dyes and colourants and coloured indicators, whiteners such as zinc oxide and titanium oxide.

The composition may be in a form that it may be dispensed in any known manner, such as by pallet knife, syringe, static mixer, roll-on applicator, spray, wipe, brush, foam, sponge, non-woven, part integrated or fully integrated into dressing, or manually applied. An applicator using a sponge is demonstrated with Chloraprep i.e. http://www.chloraprep.co.uk. For a two part curing system that requires mixing, a static mixer such as a double barreled syringe with a mixing head may be used.

Preferably therefore the curable two part composition is provided as at least one Part A and at least one Part B sealed in or on respective receptacles or supports suitable for cooperatively dispensing from a cooperative dispensing device, preferably sealed in respective barrels or respective cassettes for a static mixer such as a double barrel syringe, more preferably provided together with a cooperating dispensing device such as a static mixer.

More preferably a syringe with a nozzle to allow insertion of material into exposed transmission layer, or a spreader tip to allow spread of material across the severed transmission layer edge, or a combination thereof (spreader having plural projecting apertures) may be used (e.g. Double-Syringe Prefilled Delivery System (L-System), Medmix Systems Ag, fitted with static mixer and spreader tip http://www.medmix.ch/L-SYSTEM.html).

For certain embodiments there is a clear advantage in using an applicator with an integral spreader. Where material is applied directly to the severed dressing edge, particularly in the case of an extended severed edge, it is advantageous to manipulate this material to ensure optimal placement. An integral spreader minimises cross contamination when the sealant is manipulated. During the manipulation cross contamination could relate to: contamination of the sealant with a microbiological burden, contamination of the sealant with foreign bodies, contamination of the sealant with chemicals (such chemicals may have an influence on the sealant) and contamination of personnel or equipment with the sealant. For other embodiments there is advantage in using an applicator without a spreader, for example for filling body crevices etc.

Where the composition is a curing system chemical contamination may adversely affect the cure process. For example where the composition is a platinum catalysed RTV-2 silicone, contact with latex or nitrile containing gloves may affect the curing. The problem caused by the example given has been documented in the dental press with regards to the delayed setting of polyvinyl siloxane dental impression materials when mixed with certain types of glove (Y. Walid, Z. Al-Ani and R. Gray, Silicone impression materials and latex gloves. Is interaction fact or fallacy?, Dent Update, 2012, 39, pp. 39-42).

In a medical setting an integral applicator with spreader therefore overcomes the obstacle of a clinician being unable to use a gloved finger (subject to the chemical composition of the glove) to manipulate the sealant, overcomes the possibility of using an ungloved finger, thus eliminating direct hand to patient contact (not only would this approach be inappropriate for most clinical settings, it would likely result with transfer of the curing composition to the clinician's fingertip) and overcomes the requirement to contaminate any other medical devices or implements with the curing composition.

Dispensing may be by means of syringe or static mixer having a nozzle head comprising a combination of spreader tip with plural nozzles as hereinbefore and hereinbelow defined, for example a spreader having plural projecting apertures. Preferably a nozzle head comprises 2 to 10 nozzles for example 3 to 6 nozzles such as 3 or 5 nozzles. Nozzles preferably have low aperture to dispense sealant to the interior portion within the exposed portion of transmission layer. For example the spread of the nozzle head may match the width of the bridging portion enabling dispensing on a single insertion. This embodiment of dispenser for and mode of dispensing composition benefits from a decreased burden and decreased requirement for accuracy on the part of the operator, an increase in mechanical accuracy of dispensing location and continuous seal formation. It may also slightly reduce the back-pressure at the syringe allowing the use of higher viscosity composition. A substantial border region as hereinbefore defined may contribute to seal integrity.

Preferably a nozzle head has moderate width or spread of head for dispensing into exposed portion of a transmission layer on a curve, e.g. a body contour, for example having from 2 to 4 nozzles, such as 2 or 3 nozzles. An alternative multi nozzle head is flexible or deformable in two locations facilitating dispensing into exposed portion of a transmission layer on a curve, e.g. a body contour and/or dispensing into a location having obstructed access. Such nozzle head comprises a flexible arm or restraint through which the plural nozzles emerge. The arm is joined to the main nozzle head and thereby to releasably to the static mixer, optionally via flexible tubes. The arm may be bent to conform to an arc. The tubes may similarly be bent to conform to generate an angled nozzle. The tubes may beneficially increasing the entry angle for dispensing.

The flexible arm is typically not elastic, i.e. it retains the shape conferred for dispensing until bent to return to its original shape or a different conformation. The flexible arm could be formed of a deformable polymer or putty or the like or it could be a mechanical flexible or deformable arm (i.e. http://snakeclamp.com/ or http://joby.com/gorillapod).

Preferably a dispenser has low profile and can be contained within an imaginary cone. This dictates the maximum dimensions that may advantageously be considered in the design of the dispenser to allow a shallow entry angle relative to the skin to allow a nozzle to be inserted into an exposed portion of transmission layer in a dressing adhered to a patient.

Preferably the sealant is a TNP sealant which generates or enhances a fluid-tight, preferably an air-tight, seal.

In one embodiment a composition comprises a RTV-2 silicone such as Silpuran 2445$^{TRM}$ which may optionally be modified to have viscosity as hereinbefore defined. Modification of viscosity is as known in the art and is suitably by incorporating filler such as for example fumed silica or optionally translucent filler or resin or reinforcing resin as hereinbefore defined, to achieve the hereinbefore defined viscosity, or by combining Parts A and B and allowing to pre-react to the hereinbefore defined viscosity before application, or the like. Increasing cure rate is as known in the art, for example increasing the amount of catalyst or reducing the amount of catalyst inhibitor present, if any.

Method of Preparation

A further aspect is the preparation of a composition as hereinbefore defined. Methods for preparing non-curing or curable compositions as hereinbefore defined in 1 or more Parts are known in the art. Preferably the method comprises loading composition or respective parts thereof into an applicator or cassettes therefore as hereinbefore defined.

A further aspect is a method for preparing a curable composition as hereinbefore defined comprising the steps of:
combining polymers (i) and (ii) and catalyst (iii) as hereinbefore defined to form at least one Part A and at least one Part B; in manner suitable for cooperatively dispensing, for example for cooperatively dispensing from a double barrel syringe.

Method of Sterilisation

A further aspect is a method of sterilising the curable composition as hereinbefore defined comprising heating the one or more parts, for example the at least one Part A and at least one Part B sealed in respective thermally stable receptacles or supports at an elevated temperature of 121° C. or more for a period of up to 28 hours, or by irradiating wherein in the case of a 2 part curable composition the polymers (i) and (ii) and catalyst (iii) are apportioned in at least one Part A and at least one Part B in manner such that polymer (ii) is absent from Part A and polymer (i) is absent from Part B or Part B incorporates a trace amount of polymer (i) represented as molar ratio (Si—H unit or moiety)/(alkenyl unit or moiety) of greater than or equal to 2000 with a radiation source selected from the group consisting of gamma, x-ray, and e-beam radiation in effective sterilising dose.

Device

A further aspect is in the form of a device suitable for use in the field of woundcare, comprising a dispensing device having one or plural barrel(s) or cassette(s), advancing means and optional mixing means, said barrel(s) or cassette(s) comprising the composition as hereinbefore defined, in the case of a two or more part composition such that Parts A and B are contained in respective barrels or cassettes, the device having means for contacting respective Parts.

Preferably optional mixing means, contacting means and/or advancing means are provided integral with or separate from the device. Mixing means may be static or active. The device may incorporate a dwell chamber for mixed Parts A and B to partially cure to higher viscosity before being dispensed.

Preferably the device is disposable comprising integral barrel(s) or cassette(s).

Preferably the device comprises an applicator for applying composition comprising means to configure composition on application, for example comprising an applicator with nozzle or integral spreader or a combination thereof.

Preferably a device comprises a nozzle head comprising a combination of spreader tip with plural nozzles as hereinbefore and hereinbelow defined, for example a spreader having plural projecting apertures. Preferably a nozzle head comprises 2 to 10 nozzles for example 3 to 6 nozzles such as 3 or 5 nozzles. Nozzles preferably have low aperture to dispense sealant to the interior portion within the exposed portion of transmission layer. For example the spread of the nozzle head may match the width of the bridging portion enabling dispensing on a single insertion. This embodiment of dispenser for and mode of dispensing composition benefits from a decreased burden and decreased requirement for accuracy on the part of the operator, an increase in mechanical accuracy of dispensing location and continuous seal formation. It may also slightly reduce the back-pressure at the syringe allowing the use of higher viscosity composition. A substantial border region as hereinbefore defined may contribute to seal integrity.

Preferably a nozzle head has moderate width or spread of head for dispensing into exposed portion of a transmission layer on a curve, e.g. a body contour, for example having from 2 to 4 nozzles, such as 2 or 3 nozzles. An alternative multi nozzle head is flexible or deformable in two locations facilitating dispensing into exposed portion of a transmission layer on a curve, e.g. a body contour and/or dispensing into a location having obstructed access. Such nozzle head comprises a flexible arm or restraint through which the plural nozzles emerge. The arm is joined to the main nozzle head and thereby to releasably to the static mixer, optionally via flexible tubes. The arm may be bent to conform to an arc. The tubes may similarly be bent to conform to generate an angled nozzle. The tubes may beneficially increasing the entry angle for dispensing.

The flexible arm is typically not elastic, i.e. it retains the shape conferred for dispensing until bent to return to its original shape or a different conformation. The flexible arm could be formed of a deformable polymer or putty or the like or it could be a mechanical flexible or deformable arm (i.e. http://snakeclamp.com/ or http://joby.com/gorillapod).

Preferably a dispenser has low profile and can be contained within an imaginary cone. This dictates the maximum dimensions that may advantageously be considered in the design of the dispenser to allow a shallow entry angle relative to the skin to allow a nozzle to be inserted into an exposed portion of transmission layer in a dressing adhered to a patient.

In a further embodiment there is provided a novel device as hereinbefore defined comprising a nozzle head comprising a combination of spreader tip with plural nozzles as hereinbefore and hereinbelow defined, for example a spreader having plural projecting apertures. Preferably a nozzle head comprises 2 to 10 nozzles for example 3 to 6 nozzles such as 3 or 5 nozzles. Further features are as hereinbefore described.

If required these systems may be used together with a suitable skin-compatible sealant at the perimeter as defined in PCT GB2012/000866.

A dressing as hereinbefore defined may be any wound dressing, preferably is a wound dressing having a Si wound contact surface, more preferably is a TNP dressing, optionally modified to comprise a perimeter region as hereinbefore defined. Known TNP dressings include: Smith & Nephew Disposable Kits for TNP such as Smith & Nephew, RENA-SYS-F/AB, Abdominal Dressing Kit; Smith & Nephew, RENASYS-F/P, Foam Dressing Kit With Port; Smith & Nephew, RENASYS-G, Gauze Dressing Kit; Smith & Nephew, PICO™ dressing kit; and KCl Kits for TNP including, V.A.C.™ GranuFoam Dressings Kits; and the like. Additional dressings and methods of treating wounds with negative pressure are disclosed in the following applications that are hereby incorporated by reference: U.S. application Ser. No. 13/381,885, filed 30 Dec. 2011 and published as US2012/0116334; U.S. application Ser. No. 12/886,088, filed 20 Sep. 2010 and published as US2011/0213287; U.S. application Ser. No. 13/092,042, filed 21 Apr. 2011 and published as US2011/0282309; U.S. application Ser. No. 12/744,277, filed 20 Sep. 2010 and published as US2011/0028918; and U.S. application Ser. No. 12/744,218, filed 20 Sep. 2010 and published as US2011/0054421, also WO2011/000622, WO 2011/000621, WO2011/135285, WO2011/135286, U.S. Pat. Nos. 7,964,766 and 7,615,036 (all Smith & Nephew) the contents of which are incorporated herein by reference. Conventional TNP dressings are applied with a drape placed thereover, of which the second face is air-tight. Such dressings can additionally comprise a tissue (wound) contact layer, a negative pressure distribution and transmission layer and an optional wound exudate absorbing layer as hereinbefore defined.

Preferably the composition is dispensed to a composite TNP dressing such as the PICO™ dressing. A composite dressing incorporates an integral air-tight backing layer (also referred to herein as a wound cover or drape), that may be made of a gas impermeable membrane and integral TNP therapy layers, such as one or more negative pressure transmission or distribution layers, a tissue (wound) contact layer, an absorbent material layer such as a wound exudate absorbing layer or acquisition distribution layer (ADL) any of these optionally including a superabsorbent polymer (SAP), said layers positioned beneath the backing layer, and the backing layer or wound cover optionally allows transpiration or liquid evaporation from wound exudate, as for example with the PICO™ dressing.

For example, one or more transmission layers or other layers may be positioned or enclosed between a backing layer and an optional wound contact layer. The transmission layer(s) may be in turn enclosed between the backing layer and (optional wound contact layer and) a wound site over which the dressing is configured to be positioned, for example sealed therebetween. The composite dressing may be supplied together with a number of adhesive strips comprised of drape material or may omit such strips with sealing by means of a sealant as disclosed in PCT/GB2012/000866, the contents of which are incorporated herein by reference.

The composition may therefore be applied to any dressing which it is desired to cut to size or shape or to profile or articulate. Cutting is simply by removing the excess portion and retaining the required portion including negative pressure port.

Preferably the composition is dispensed to a trimmable dressing, having a main dressing portion in fluid (gas) communication with additional dressing portions or cells. One or more additional portions or cells may be removed to provide a dressing having size or shape or profile or articulation to be compatible with a wound or wound site to be dressed. Preferably portions or cells may be retained to provide a large surface area, or elongate, dressing to dress a similarly large surface area or elongate wound, or portions or cells may be removed to dress a correspondingly reduced surface area or reduced length wound; preferably one or more additional portions or cells may be conformed to provide a shaped dressing to dress a similarly shaped wound or to dress a wound incorporating or adjacent a protrusion such as a fixation device, for example a pin, or such as a body part such as a digit; preferably one or more additional portions or cells may be conformed to provide a profiled dressing to dress a similarly profiled wound or wound site, such as a wound located on complex body topography; preferably one or more additional portions or cells may be articulated to dress a similarly articulated wound or wound site such as a wound located on a joint.

In an advantage the composition may be used to seal a trimmable dressing as disclosed in U.S. Provisional Application Ser. No. 61/800,040, filed Mar. 15, 2013, titled "WOUND DRESSING AND METHOD OF TREATMENT," the contents of which are incorporated herein directly and by reference.

A trimmable dressing is preferably a wound treatment apparatus for treatment of a wound site comprising:
  a backing layer having an upper surface and a lower surface and defining a perimeter configured to be positioned over skin surrounding a wound site;
  a transmission layer configured to be positioned below the backing layer; and
  one or more ports configured to transmit negative pressure through the backing layer for the application of topical negative pressure at the wound site;
  wherein the apparatus comprises a plurality of cells or regions separated by one or more trimmable portions. Trimmable portion(s) may be bridging portions as hereinbefore defined.

In some embodiments, the plurality of cells forms a plurality of repeating negative pressure treatment modules.

In one embodiment, one or more of the modules can be removed and the removed module(s) can subsequently be used to provide negative pressure to the wound site. In another embodiment, one or more modules can be removed and the remaining module(s) can subsequently be used to provide negative pressure to the wound site. In further embodiments, the trimmable portions may have a maximum width of 50 mm (or approximately 50 mm), 40 mm (or approximately 40 mm), 30 mm (or approximately 30 mm), 20 mm (or approximately 20 mm), or even 15 mm (or approximately 15 mm). In some embodiments, the trimmable portion may be from 10 mm to 20 mm (or approximately 10 mm to approximately 20 mm). The one or more trimmable portions may comprise one or more bridging portions having a smaller width as compared to the width of an adjacent cell or region. For example, the bridging portion may have a maximum width of ⅛, ¼, or ⅓ (or approximately ⅛, ¼, or ⅓) of a width of an adjacent cell or region. The plurality of cells or regions may comprise an absorbent material, the absorbent material positioned between the transmission layer and the backing layer. The one or more trimmable portions may comprise an absorbent material, the absorbent material positioned between the transmission layer and the backing layer. In other embodiments, no absorbent material is positioned between the transmission layer and the backing layer. Some embodiments may further comprise an acquisition distribution layer having a similar footprint to the transmission layer, the acquisition distribution layer configured to be positioned above the transmission layer. The apparatus is preferably as further hereinbelow defined.

Exposed portion(s) as hereinbefore defined are the result of removing a portion of the wound dressing, which may be by any envisaged means, for example cutting the wound dressing or tearing along a weakened line. Composite wound dressings may comprise a border for affixing around a wound, about a central wound contact portion. The dressing as hereinbefore defined may include a backing layer and wound contact layer of similar footprint or surface area to the transmission layer or other layers enclosed therebetween, for example is a borderless dressing) or of greater footprint or surface area than the transmission layer enclosed therebetween (for example is a bordered dressing). Exposed portion(s) as hereinbefore defined result from removing a portion of the wound dressing as hereinbefore defined directly enclosing the transmission layer or other layers, for example by cutting into or through the backing layer and wound contact layer and the transmission layer therebetween.

Embodiments of dressings described herein address the problem of providing dressings in a range of sizes or shapes to accommodate irregularly shaped wounds or body topography, for example vein harvest wound dressings accommodating variations in height and leg-length of individuals, the provision of which is impractical both to the manufacturer and to the user. Embodiments enhance adaptability of existing dressings, including more recently introduced multisite dressings such as trilobes and quadrilobes. Certain embodiments enable a portion of a dressing to be removed to create a main wound dressing of desired size or shape or profile or articulation, and sealing exposed portion(s) thereof to contain a negative pressure.

The portion(s) of the wound dressing may be removed to size the main wound dressing portion for positioning over a wound as hereinbefore defined, for example an incisional wound, an elongate leg wound, an arcuate incisional wound and the like. Similarly the portion(s) of the wound dressing may be removed to shape the main wound dressing portion for positioning over a wound as hereinbefore defined, such as a flap wound, about a protruding device such as a fixation device or a protruding body part, to profile the main wound dressing for positioning over a wound as hereinbefore defined, for example on complex body topography, or to articulate the main wound dressing for positioning over a wound as hereinbefore defined for example on a flexing joint.

The wound treatment apparatus may be rolled into a tape which can be cut along the one or more bridging portions. Cutting along the bridging portion may sever adjacent cells.

The composition may alternatively be advantageously dispensed to seal a dressing for treatment of a wound site comprising:
 a backing layer having an upper surface and a lower surface otherwise a backing sheet as hereinbefore termed and defining a perimeter configured to be positioned over skin surrounding a wound site;
 a transmission layer configured to be positioned beneath the backing layer; or otherwise positioned at or on one side of one face of the backing sheet and
 a plurality of ports configured to transmit negative pressure spaced apart on the backing layer.

The wound treatment apparatus may be configured to be rolled into a tape. The plurality of ports each may comprise an opening in the backing layer covered with a releasable tab. The transmission layer may comprise one or more bridging portions having a smaller width than adjacent portions of the transmission layer. A negative pressure may be established at a wound site by means of any one of the plurality of ports, the remainder of which may remain sealed or may be removed with a section of dressing. The wound treatment apparatus may be used in any desired length by cutting between adjacent ports.

In above dressings, the wound treatment apparatus further comprises an optional wound contact layer, with the transmission layer(s) positioned between the backing layer and the wound contact layer. The transmission layer(s) may be in direct or indirect contact with a lower surface of the backing layer. In some embodiments, the one or more transmission layers comprise a first layer comprising a spacer material configured to vertically wick fluid. The one or more transmission layers may further comprise a second layer comprising an acquisition distribution material configured to horizontally wick fluid, the second layer positioned above the first layer. One of the first layer and the second layer, or both, may be present in the one or more bridging portions. In other embodiments, the one or more transmission layers comprise an acquisition distribution material configured to horizontally wick fluid. In some embodiments, the port may comprise an opening in the backing layer. The port may comprise a port member attached to the backing layer over an opening in the backing layer. The port member may be sealed to the upper surface of the backing layer. Some embodiments may further comprise an absorbent material between the backing layer and the transmission layer having a similar footprint to that of the transmission layer(s). Absorbent material may be present or absent in bridging portion(s) as hereinbefore defined. Some embodiments of the one or more transmission layers may further comprise an acquisition distribution layer between the backing layer and the optional wound contact layer and the transmission layer and/or absorbent layer having a similar footprint to that of the absorbent material and/or absorbent layer. The one or more transmission layers may further comprise a spacer material configured to distribute negative pressure, the spacer material having a similar footprint to the acquisition distribution material, the spacer material configured to be positioned beneath the acquisition distribution material. Acquisition distribution layer or material may be present or absent in bridging portion(s) as hereinbefore defined. The acquisition distribution material may be provided as the transmission material or layer.

The transmission layer (hereinafter layer(s)) may have a rectangular shape having a longitudinal axis extend along its length. The transmission layer may comprise one or more bridging portions centered on the longitudinal axis. The transmission layer may comprise three or more bridging portions centered on the longitudinal axis. The one or more bridging portions may also be offset from the longitudinal axis. The one or more bridging portions may have a width that is less than ⅓ the width of adjacent portions of transmission layer. The one or more bridging portions may have a width that is less than ¼ the width of adjacent portions of transmission layer. The one or more bridging portions may have a width that is less than ⅛ the width of adjacent portions of transmission layer. As is used herein, a smaller width represents a narrowing of or neck or constriction in transmission layer with respect to adjacent portions thereof. The transmission layer may have a T-shape with a bridging portion on each leg of the T. The transmission layer may have a T-shape with at least one bridging portion on each leg of the T. The transmission layer may comprise a plurality of cells each separated by one or more bridging portions. The transmission layer may comprise a plurality of cells, and wherein each of the plurality of cells is connected to at least one adjacent cell by one or more bridging portions, preferably the bridges provide for gas communication between adjacent cells.

Some embodiments may further comprise a fluidic connector configured to supply negative pressure to the port. Some embodiments may further comprise a source of negative pressure configured to supply negative pressure through the port. Negative pressure may be established at a wound site by means of any one of the plurality of ports, or by means of multiple ports of the plurality of ports, the remainder of which may remain sealed or may be removed with a section of dressing. Some embodiments may further comprise one or more separate or integral adhesive strips or sealing strips. Strips are configured to retain and seal the backing layer to skin surrounding a wound after the apparatus is cut along or across the one or more bridging portions, i.e between adjacent cells or ports. Strips may be comprised of backing layer material, such as polyurethane or hydrocolloid, or silicone based material such as OPSITE◊ FLEXIFIX◊ or OPSITE◊ FLEXIFIX◊ Gentle.

In a further aspect there is provided a novel apparatus as hereinbefore defined. Accordingly there is provided a wound treatment apparatus for treatment of a wound site comprising:
- a backing layer having an upper surface and a lower surface and defining a perimeter configured to be positioned over skin surrounding a wound site;
- a transmission layer configured to be positioned below the backing layer; and
- one or more ports configured to transmit negative pressure through the backing layer for the application of topical negative pressure at the wound site;
- wherein the apparatus comprises a plurality of cells or regions separated by one or more trimmable portions. Features are as hereinbefore defined.

The one or more ports may each comprise an opening in the backing layer covered with a releasable tab, and negative pressure may be applied to the backing layer through at least one of the openings. Some embodiments may comprise multiple ports configured to transmit negative pressure through the backing layer, each port corresponding to a separate negative pressure treatment module. Some embodiments may further comprise a wound contact layer configured to be positioned beneath the transmission layer, the wound contact layer further configured to seal to the backing layer around the perimeter.

In some embodiments, the plurality of cells may be approximately the same size, approximately square, and configured in a grid. In other embodiments, the plurality of cells may be configured in a T-shape. In other embodiments, the plurality of cells may be configured into a roll. In other embodiments, the plurality of cells may be configured in a linear arrangement. In some embodiments, each of the plurality of cells may be configured with one of the one or more ports. In other embodiments, at least two of the plurality of cells may be each configured with one of the one or more ports. The apparatus may further comprise a source of negative pressure connected to some or all of the one or more ports. In some embodiments, the dressing may comprise an exposed portion of transmission layer. The exposed portion may be sealed with a sealant or adhesive material. The apparatus is preferably as further hereinbefore defined.

In some embodiments, the at least one material layer of the first portion comprises one or more of a transmission layer such as reticulated open-cell foam, woven material, non-woven material, 3D knit fabric, Baltex 7970 weft knitted polyester, acquisition distribution material, DryWeb TDL2, SlimCore TL4, or the like. The at least one material of the first portion can additionally or alternatively comprise an absorbent layer, for example a superabsorbent pad comprising cellulose fibers and superabsorbent particles, MH460.101, ALLEVYN™ foam, Freudenberg 114-224-4, or Chem-Posite™ 11C-450. In some embodiments, the bridging portion comprises at least one material layer comprising one or more of reticulated open-cell foam, woven material, non-woven material, 3D knit fabric, Baltex 7970 weft knitted polyester, acquisition distribution material, DryWeb TDL2, SlimCore TL4, or the like. In some embodiments, the at least one material layer of the bridging portion should transmit a negative pressure of at least −40 mmHg against a set point in the range −60 to −200 mmHg with an air leak of 50 cc/minute. In some embodiments, the at least one material layer of the bridging portion should experience a pressure differential of approximately −25 mmHg or less (that is, closer to zero) at a set point of −200 mmHg with an air leak of 50 cc/minute over an approximately 20 mm±1 mm distance. In other embodiments, the at least one material layer of the bridging portion should experience a pressure differential of approximately −5 mmHg or less (that is, closer to zero) at a set point of −200 mmHg with an air leak of 50 cc/minute over an approximately 20 mm±1 mm distance. In some embodiments, the at least one material layer of the bridging portion has a height, in an uncompressed state, of at least 1 mm (or approximately 1 mm), at least 3 mm (or approximately 3 mm), at least 4 mm (or approximately 4 mm), or at least 5 mm (or approximately 5 mm), and a width of at least 1 mm (or approximately 1 mm), or at least 2 mm (or approximately 2 mm), at least 3 mm (or approximately 3 mm), at least 4 mm (or approximately 4 mm), or at least 5 mm (or approximately 5 mm). In some embodiments, the at least one material layer of the bridging portion has a maximum height, in an uncompressed state, of 9 mm (or approximately 9 mm) for purposes of being more easily re-sealable when cut. In some embodiments in which the dressing is sealed with a sealant, the at least one material layer can be resilient to compression such that a height of a sealed portion, in a compressed state, is substantially the same as the height of the sealed portion in an uncompressed state. In one embodiment, the at least one material layer of the bridging portion comprises a spacer material having a height of at least 2 mm (or approximately 2 mm) and a width of at least 1 mm (or approximately 1 mm). In one embodiment, the at least one material layer of the bridging portion comprises a reticulated open-cell foam having a height of at least approximately 5 mm and a width of at least approximately 3 mm, which, when wet, may experience a pressure differential of −8.9 (or approximately −8.9) mmHg. In another embodiment, the at least one material layer of the bridging portion comprises an acquisition distribution layer (e.g., SlimCore TL4) having a height of at least approximately 2 mm and a width of at least approximately 4 mm. Such dimensions can represent an uncompressed dimension of the material layer of the bridging portion. In one embodiment, the at least one material layer of the bridging portion is not compressible.

We have found that a composition when dispensed to seal a dressing in manner as hereinbefore defined, may provide an advantageous seal in relation to an exposed trimmed portion or bridging portion comprising material layer(s) which undergo no change or substantially no change in compressibility on initiation of negative pressure, i.e. is resilient to or substantially resilient to compression induced by negative pressure, or which undergo a substantially similar compression to or lesser compression than the composition seal, on initiation of negative pressure, i.e is substantially equally resilient or less resilient than the composition seal to compression induced by negative pressure. In particular in relation to a curing or hardening system, this relative compressibility is in relation to the cured elastomer or hardened seal. Preferably a composition forms a seal which is compressible to touch in relation to material layer(s) which are substantially non-compressible or compressible to a lesser degree, on initiation of negative pressure, than the seal. Preferably the one or more trimmable portions or briding portions comprise material substantially resilient to the application of negative pressure, preferably the bridging portion(s) have height which is substantially unchanged on the application of negative pressure, preferably having height which is reduced by less than or equal to 10%, more preferably 8%, most preferably 5%, on the application of negative pressure. This ensures a smooth surface to the dressing and minimal discomfort provided to the wearer, if negative pressure is applied after sealing the dressing, and also ensures that the seal remains intact and is not ruptured if negative pressure is applied before sealing the dressing and is subsequently temporarily interrupted.

In some embodiments, the bridging portion comprises the same layer(s) as the first portion. In other embodiments, the bridging portion comprises fewer layers than the first portion. In some embodiments, the layer(s) in the bridging portion have a smaller width than the layer(s) in the first portion. In some embodiments, the layer(s) in the bridging portion have a dimension that is smaller than the layer(s) in the first portion (for example, the individual or combined height of the layer(s) in the bridging portion is smaller than the height of the layer(s) in the first portion. In other embodiments, the layer(s) in the bridging portion have the same width as the layer(s) in the first portion. In some embodiments, the bridging portion connects the first portion to an adjacent portion having a similar layered construction and/or width as the first portion. In some embodiments, there are multiple bridging portions that may connect a first portion to multiple adjacent portions, or may connect between multiple adjacent portions.

Kit and Components Thereof

A further aspect is a kit for use in the field of wound care comprising a dressing for overlying a wound and skin thereabout which may be cut to size or shape as hereinbefore defined together with a composition as hereinbefore defined.

Some kits comprise a vacuum pump.

In a particular advantage, the kit, sealant composition and/or dressing or wound cover may be terminally sterile. Techniques are known for sterilising apparatus, such as dry heat, steam, radiation and the like. GB1020005.3, GB 1019997.4 and GB1104512.7 disclose terminally sterilisable 2 part compositions and methods for their sterilisation. Methods include heat sterilisation and radiation sterilisation, in particular gamma, e-beam or x-ray radiation sterilisation. Preferably the sealant is terminally sterilisable or sterile and is sterilized prior to dispensing by heating the first and second parts in a thermally stable receptacle or support at an elevated temperature of 121° C. or more for a period of up to 28 hours, or by irradiating the first and second parts with a radiation source selected from the group consisting of gamma, x-ray, and e-beam radiation with a dose that provides an effective sterility assurance level.

A further aspect is a method for dispensing or releasing, and curing a composition as hereinbefore defined, comprising dispensing into a desired location at curing temperature for curing time.

The composition may be manually mixed and dispensed. Alternatively any form of dispensing device may be employed, for example the composition may be dispensed by means of a cooperative dispensing device cooperatively dispensing, for example by means of a double barrel syringe, for example by activating respective barrels of a double barrel syringe, or loading respective cassettes therefore and activating.

A further aspect is an elastomer comprising a cured composition as hereinbefore defined.

Method of Use

A further aspect is a method for dispensing a composition as hereinbefore defined comprising:
  optionally combining Parts A and B of a curable composition as hereinbefore defined thereby initiating cure;
  dispensing composition into a location as hereinbefore defined;
  after a suitable period an optionally elastomeric seal is formed.

A further aspect is a method for sealing a woundcare dressing comprising:
  cutting a dressing to size or shape;
  positioning the dressing overlying a wound and skin thereabout;
  optionally combining Parts A and B of a curable composition as hereinbefore defined thereby initiating cure;
  dispensing composition into a location as hereinbefore defined;
  after a suitable period an optionally elastomeric seal is formed at the severed dressing edge.

Preferably the composition is dispensed by means of a syringe for example a cooperative dispensing device as hereinbefore defined cooperatively dispensing, for example by means of a double barrel syringe, for example by activating respective barrels of a double barrel syringe, or loading respective cassettes therefore and activating, preferably wherein the syringe incorporates integral means to configure the dispensed sealant, for example an integral spreader head.

Method of Treatment

A further aspect is a method for sealing a dressing or for treating a wound site, of a human or animal subject in need thereof comprising:
dressing the wound site with a dressing, as hereinbefore defined, exposing a portion thereof as hereinbefore defined and
dispensing a composition as hereinbefore defined.
Preferably the method comprises:
providing a wound dressing as hereinbefore defined comprising:
a backing layer; and
a transmission layer positioned beneath the backing layer,
removing a portion of the wound dressing to create a main wound dressing portion with one or more exposed portions;
positioning the main wound dressing portion over a wound;
sealing the main wound dressing to skin surrounding the wound, and further sealing further sealing the one or more exposed portions of the main wound dressing portion; and
applying negative pressure to the wound through the backing layer of the main wound dressing portion.

In some embodiments of the method, removing a portion of the wound dressing comprises cutting the wound dressing across at least one of the one or more bridging portions. At least a portion of the wound dressing may comprise pre-cut score marks to facilitate removing of the portion of wound dressing. The dressing may comprise a plurality of openings in the backing layer covered with a releasable tab, and negative pressure may be applied to the backing layer through one of the openings. The dressing may comprise a plurality of openings in the backing layer covered with a releasable tab, and negative pressure may be applied to the backing layer through two or more of the openings.

The portions of the wound dressing may be removed to size the main wound dressing portion for positioning over an incisional wound. The portions of the wound dressing may be removed to size the main wound dressing portion for positioning over an elongate leg wound. The portions of the wound dressing may be removed to size the main wound dressing portion for positioning over an arcuate incisional wound.

In another embodiment, a method of treating a wound is provided, comprising:
providing a wound dressing comprising a backing layer, a transmission layer beneath the backing layer, and a plurality of spaced apart openings in the backing layer each covered with a releasable tab, the wound dressing configured into a length or roll;
optionally unrolling a portion of the wound dressing from the roll;
removing a portion of the wound dressing from the length or roll, the removed portion comprising at least one opening in the backing layer covered with a releasable tab;
positioning the removed portion of the wound dressing over a wound; and applying negative pressure through at least one opening in the backing layer after a releasable tab has been removed.

Preferably dispensing a sealant composition is by means of a device as hereinbefore defined.

Preferably the dressing is adhered over the wound site with at least an adhesive underside of the dressing or an adhesive disposed on at least an underside of the dressing.

Preferably the method further comprises adjusting the position of the dressing before the composition is dispensed.

Preferably the sealant is dispensed after dressing the wound site with the dressing.

Preferably the wound dressing is adapted to contain a negative pressure, the method additionally comprising applying negative pressure to the wound site using a source of negative pressure connected to the wound site.

Preferably applying negative pressure is conducted before and after dispensing sealant.

Preferably applying negative pressure is by means of a portable negative pressure source in fluid communication with the wound dressing located over a wound site.

Preferably the method includes monitoring transmitted negative pressure at the wound against generated negative pressure.

Preferably a dressing is a combination TNP therapy dressing incorporating fluid-tight backing layer, functional wound therapy layers and an integral attachment for a negative pressure source, preferably a portable and/or periodic negative pressure source by means of which negative pressure is applied to the wound site through or under the backing layer. Preferably an aperture is created into or under the drape so as to connect the wound site to the source of negative pressure.

A wound packing material may be located so as to partially or completely fill the wound site.

Providing the sealant may be by means of dispensing a sealant composition as hereinbefore defined by the method as hereinbefore defined.

The method may include monitoring transmitted negative pressure against generated negative pressure. This may be used to provide the user with feedback during the dressing application. Typically NP is monitored at the pump, or alternatively at end of port.

Preferably the dressing is applied, the NP source activated, pump down initiated, detecting for alarms indicating NP loss, rub down dressing to close off any sites of NP loss, apply sealant at severed edges.

In an advantage, providing the sealant is by means of dispensing a sealant composition, wherein the composition is a fluid that when dispensed forms a material capable of making a substantially fluid-tight seal.

Preferably the method comprises combining at least two pre-polymers to form the sealant.

Preferably the dressing is part of a portable NPWT system. The exudate is managed in a portable canister or within the dressing. The negative pressure source is portable or may be connected intermittently. Preferably the skin contact layer is an adhesive silicone gel, other adhesive or combination of adhesive silicone gel and other adhesive.

Portable composite TNP dressings are commercially available and include Prevena (KCl), NPD1000 NP wound Therapy System (Kalypto Medical Inc), PICO (Smith & Nephew), amongst others, and are more extensively described in the literature, for example in PCT/GB2011/000629, the contents of which are incorporated herein by reference.

Upon the application of negative pressure with the pump, the dressing may in some embodiments partially collapse and present a wrinkled appearance as a result of the evacuation of some or all of the air underneath the dressing. In some embodiments, the pump may be configured to detect if any leaks are present in the dressing, such as at the interface between the dressing and the skin surrounding the wound site. Should a leak be found, such leak is preferably remedied prior to continuing treatment.

Treatment of the wound site preferably continues until the wound has reached a desired level of healing. In some embodiments, it may be desirable to replace the dressing after a certain time period has elapsed, or if the dressing is full of wound fluids. During such changes, the pump may be kept, with just the dressing being changed.

A further aspect provides the use of a composition, kit or apparatus as hereinbefore defined for dressing wounds, preferably for negative pressure wound therapy dressing of wounds as hereinbefore defined. The sealant composition, kit and apparatus may be useful for example in sealing medical dressings, for example in restraining egress of wound exudate or ingress of air or infection, in addition to providing a vacuum seal for TNP application.

Such use includes use on wounds selected from chronic, acute, traumatic, sub-acute and dehisced wounds, ulcers (such as pressure or diabetic), partial-thickness burns and flaps and grafts. These include open, moist, granulating wounds, preferably surgical wounds such as those resulting from excision of ulcers, cancerous tissue such as perianal and perineal wounds and the like. For optimum healing of such wounds, the wound should be prevented from closing in on itself and allowing fluids to accumulate, whilst at the same time allowing the tissue around the wound to progressively contract, and the wound to shrink. Wound filling materials in NPWT therefore function as a type of "stent", supporting the wound and holding it open.

A sealant composition, kit or apparatus is particularly suited for use in clean, aseptic or sterile applications. Preferably the composition, kit or apparatus is rendered sterile, as known in the art or as hereinbefore defined, and packaged within barrier means. Further barrier means provide a barrier to infection, whereby the composition, kit or apparatus is a double wrapped item, this allows for the removal of the first layer of sterile sealed packaging to reveal receptacles or supports such as cartridges for or incorporated in a syringe, adhesive strips and the like, which are completely sterile inside and out, facilitating entry into a sterile environment. The composition omitting a further barrier means would comprise a non-sterile external surface of receptacles or supports and associated barrier means. If it is not possible to sterilise the composition using standard conditions for medical apparatus as hereinbefore described, it may not be possible to take such a composition into a sterile field.

A sealant for medical dressings may be applied in any known or novel manner. WO 00/74738 (Guyuron) discloses use of silicone based RTV-2 compositions to seal wounds i.a to minimise potential infections. The sealant may suitably therefore be used by casting on top of the wound and surrounding skin and allowing to cure.

A further aspect provides the medical use of a kit, sealant or apparatus as hereinbefore defined.

Embodiments have one or more of the following advantages: Allows severed dressing edges to be sealed readily.

Sealing of 3-dimensional dressing perimeters following complex body contours enhancing the ability to remove or reduce leaks.

Sealing of custom sized, shaped, contoured, articulated dressings.

Sealing of dressings where the borders conform to body geometries with tight external radii or are otherwise subject to high levels of deformation.

Sealing of systems where the dressing will be subject to a great deal of movement (e.g. neck, shoulder, underarm, elbow, forearm, wrist, hand, groin, knee, ankle, heel, foot).

A number of specific embodiments are given hereinbelow, appropriate for conventional Advanced Wound Dressings, conventional NPWT Drapes/Dressings or PICO™ and a sealant as hereinbefore defined. General references hereinbelow are however not to be construed as limiting to the specific figure or embodiment which they are intended to illustrate, rather for the sake of avoiding undue duplication such description may be present in the following section although of equal or greater relevance and equally pertinent to the foregoing.

Figure 1:
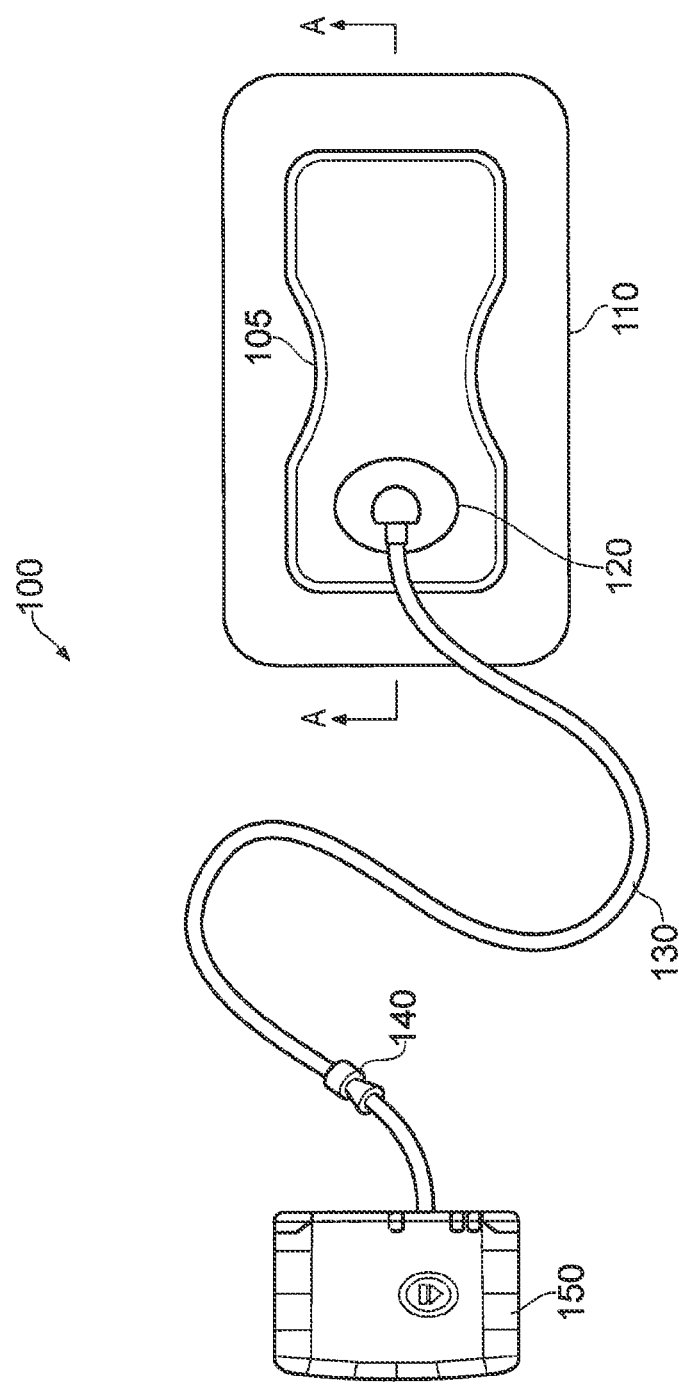
FIG. 1 illustrates an embodiment of a wound treatment system.

FIG. 1 illustrates an embodiment of a TNP wound treatment system 100 comprising a wound dressing 110 in combination with a pump 150. As stated above, the wound dressing 110 can be any wound dressing embodiment disclosed herein including without limitation dressing embodiment or have any combination of features of any number of wound dressing embodiments disclosed herein. Here, the dressing 110 may be placed over a wound as described previously, and a conduit 130 may then be connected to the port 120, although in some embodiments the dressing 101 may be provided with at least a portion of the conduit 130 preattached to the port 120. Preferably, the dressing 110 is provided as a single article with all wound dressing elements (including the port 120) pre-attached and integrated into a single unit. The wound dressing 110 may then be connected, via the conduit 130, to a source of negative pressure such as the pump 150. The pump 150 can be miniaturized and portable, although larger conventional pumps may also be used with the dressing 110. In some embodiments, the pump 150 may be attached or mounted onto or adjacent the dressing 110. A connector 140 may also be provided so as to permit the conduit 130 leading to the wound dressing 110 to be disconnected from the pump, which may be useful for example during dressing changes.

Figure 2A:
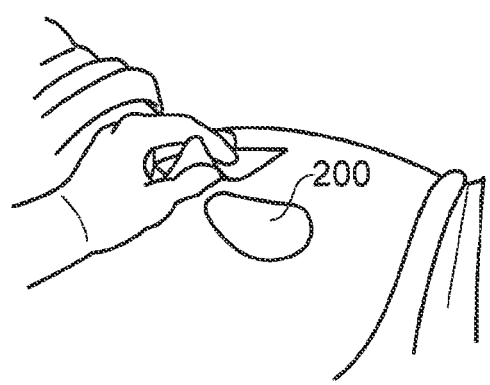
FIGS. 2A-D illustrates the use and application of an embodiment of a wound treatment system onto a patient.

FIGS. 2A-D illustrates the use of an embodiment of a TNP wound treatment system being used to treat a wound site on a patient. FIG. 2A shows a wound site 200 being cleaned and prepared for treatment. Here, the healthy skin surrounding the wound site 200 is preferably cleaned and excess hair removed or shaved. The wound site 200 may also be irrigated with sterile saline solution if necessary. Optionally, a skin protectant may be applied to the skin surrounding the wound site 200. If necessary, a wound packing material, such as foam or gauze, may be placed in the wound site 200. This may be preferable if the wound site 200 is a deeper wound.

Figure 2B:
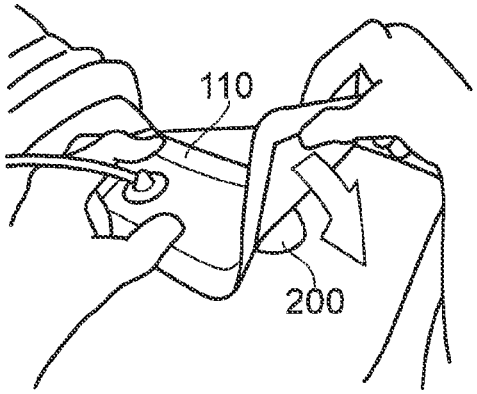

After the skin surrounding the wound site 200 is dry, and with reference now to FIG. 2B, the wound dressing 110 may be positioned and placed over the wound site 200. Preferably, the wound dressing 110 is placed with the wound contact layer 2102 over and/or in contact with the wound site 200. In some embodiments, an adhesive layer is provided on the lower surface 2101 of the wound contact layer 2102, which may in some cases be protected by an optional release layer to be removed prior to placement of the wound dressing 110 over the wound site 200. Preferably, the dressing 110 is positioned such that the port 2150 is in a raised position with respect to the remainder of the dressing 110 so as to avoid fluid pooling around the port. In some embodiments, the dressing 110 is positioned so that the port 2150 is not directly overlying the wound, and is level with or at a higher point than the wound. To help ensure adequate sealing for TNP, the edges of the dressing 110 are preferably smoothed over to avoid creases or folds.

Figure 2C:
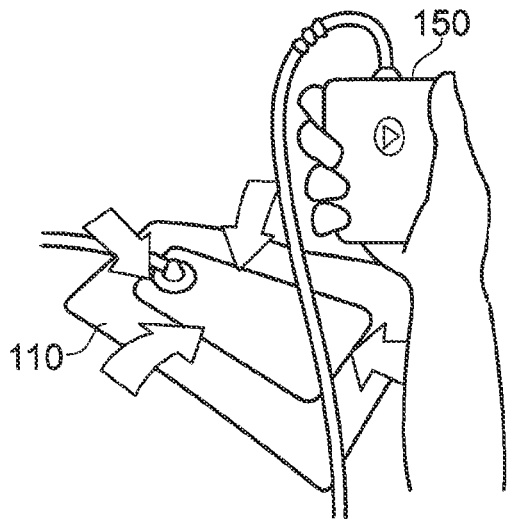

With reference now to FIG. 2C, the dressing 110 is connected to the pump 150. The pump 150 is configured to apply negative pressure to the wound site via the dressing 110, and typically through a conduit. In some embodiments, and as described above in FIG. 1, a connector may be used to join the conduit from the dressing 110 to the pump 150. Upon the application of negative pressure with the pump 150, the dressing 110 may, in some embodiments, partially collapse and present a wrinkled appearance as a result of the evacuation of some or all of the air underneath the dressing 110. In some embodiments, the pump 150 may be configured to detect if any leaks are present in the dressing 110, such as at the interface between the dressing 110 and the skin surrounding the wound site 200. Should a leak be found, such leak is preferably remedied prior to continuing treatment.

Figure 2D:
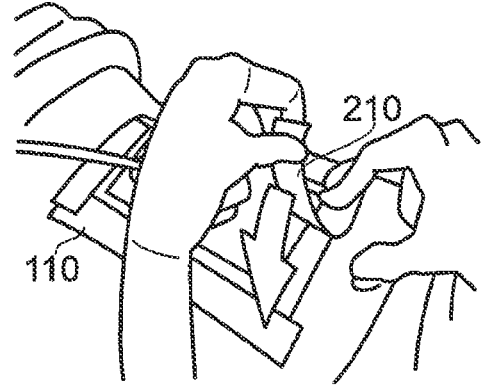

Turning to FIG. 2D, additional fixation strips 210 may also be attached around the edges of the dressing 110. Such fixation strips 210 may be advantageous in some situations so as to provide additional sealing against the skin of the patient surrounding the wound site 200. For example, the fixation strips 210 may provide additional sealing for when a patient is more mobile. In some cases, the fixation strips 210 may be used prior to activation of the pump 150, particularly if the dressing 110 is placed over a difficult to reach or contoured area.

Treatment of the wound site 200 preferably continues until the wound has reached a desired level of healing. In some embodiments, it may be desirable to replace the dressing 110 after a certain time period has elapsed, or if the dressing is full of wound fluids. During such changes, the pump 150 may be kept, with just the dressing 110 being changed.

Figure 3A:
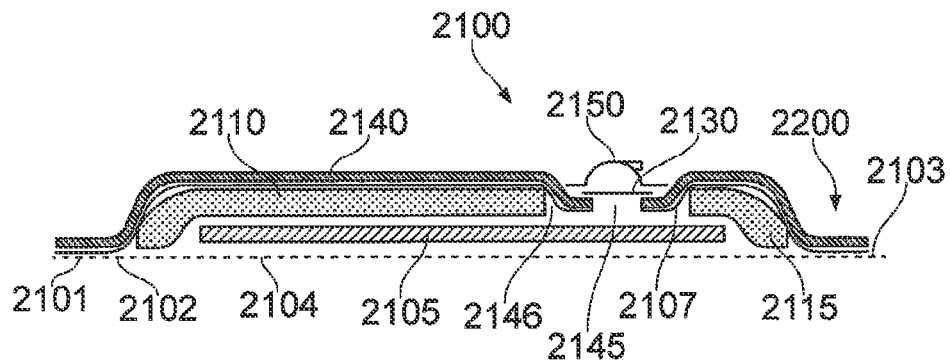
FIG. 3A illustrates an embodiment of a wound dressing in cross-section.
Figure 3B:
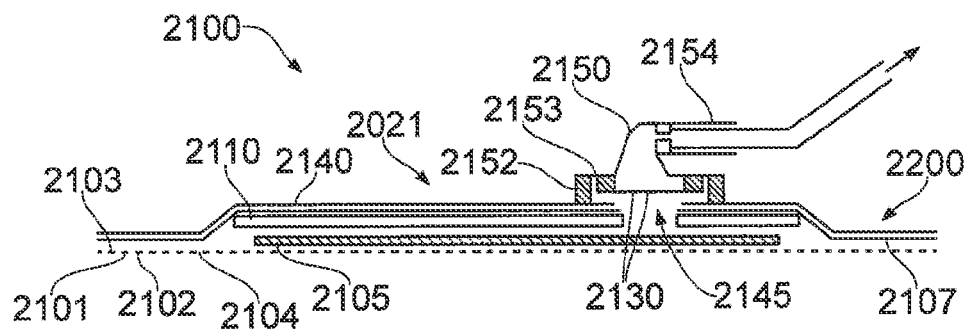
FIG. 3B illustrates another embodiment of a wound dressing in cross-section.
Figure 3C:
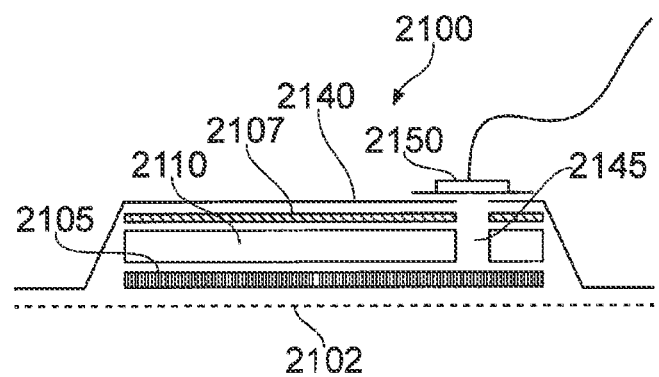
FIG. 3C illustrates another embodiment of a wound dressing in cross-section.

FIGS. 3A-C illustrates cross-sections through a wound dressing 2100 similar to the wound dressing of FIG. 1 according to an embodiment of the disclosure. A view from above the wound dressing 2100 is illustrated in FIG. 1 with the line A-A indicating the location of the cross-section shown in FIGS. 3A and 3B. The wound dressing 2100, which can alternatively be any wound dressing embodiment disclosed herein including without limitation wound dressing 110 or any combination of features of any number of wound dressing embodiments disclosed herein, can be located over a wound site to be treated. The dressing 2100 may be placed to as to form a sealed cavity over the wound site. In a preferred embodiment, the dressing 2100 comprises a backing layer 2140 attached to a wound contact layer 2102, both of which are described in greater detail below. These two layers 2140, 2102 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 2105 and an absorbent layer 2110.

As illustrated in FIGS. 3A-C, a lower surface 2101 of the wound dressing 2100 may be provided with an optional wound contact layer 2102. The wound contact layer 2102 can be a polyurethane layer or polyethylene layer or other flexible layer which is perforated, for example via a hot pin process, laser ablation process, ultrasound process or in some other way or otherwise made permeable to liquid and gas. The wound contact layer 2102 has a lower surface 2101 and an upper surface 2103. The perforations 2104 preferably comprise through holes in the wound contact layer 2102 which enable fluid to flow through the layer 2102. The wound contact layer 2102 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 2102 may help maintain the integrity of the entire dressing 2100 while also creating an air tight seal around the absorbent pad in order to maintain negative pressure at the wound.

Some embodiments of the wound contact layer 2102 may also act as a carrier for an optional lower and upper adhesive layer (not shown). For example, a lower pressure sensitive adhesive may be provided on the lower surface 2101 of the wound dressing 2100 whilst an upper pressure sensitive adhesive layer may be provided on the upper surface 2103 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 2100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 2105 of porous material can be located above the wound contact layer 2102. This porous layer, or transmission layer, 2105 allows transmission of fluid including liquid and gas away from a wound site into upper layers of the wound dressing. In particular, the transmission layer 2105 preferably ensures that an open air channel can be maintained to communicate negative pressure over the wound area even when the absorbent layer has absorbed substantial amounts of exudates. The layer 2105 should preferably remain open under the typical pressures that will be applied during negative pressure wound therapy as described above, so that the whole wound site sees an equalized negative pressure. The layer 2105 may be formed of a material having a three dimensional structure. For example, a knitted or woven spacer fabric (for example Baltex 7970 weft knitted polyester) or a non-woven fabric could be used.

A layer 2110 of absorbent material is provided above the transmission layer 2105. The absorbent material, which comprise a foam or non-woven natural or synthetic material, and which may optionally comprise a super-absorbent material, forms a reservoir for fluid, particularly liquid, removed from the wound site. In some embodiments, the layer 2100 may also aid in drawing fluids towards the backing layer 2140.

With reference to FIGS. 3A-C, a masking or obscuring layer 2107 can be positioned beneath at least a portion of the backing layer 2140. In some embodiments, the obscuring layer 2107 can have any of the same features, materials, or other details of any of the other embodiments of the obscuring layers disclosed herein, including but not limited to having any viewing windows or holes. Additionally, the obscuring layer 2107 can be positioned adjacent to the backing layer, or can be positioned adjacent to any other dressing layer desired. In some embodiments, the obscuring layer 2107 can be adhered to or integrally formed with the backing layer. Preferably, the obscuring layer 2107 is configured to have approximately the same size and shape as the absorbent layer 2110 so as to overlay it. As such, in these embodiments the obscuring layer 2107 will be of a smaller area than the backing layer 2140.

The material of the absorbent layer 2110 may also prevent liquid collected in the wound dressing 2100 from flowing freely within the dressing, and preferably acts so as to contain any liquid collected within the absorbent layer 2110. The absorbent layer 2110 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 2110 may typically be manufactured from ALLEVYN™ foam, Freudenberg 114-224-4 and/or Chem-Posite™11C-450. In some embodiments, the absorbent layer 2110 may comprise a composite comprising superabsorbent powder, fibrous material such as cellulose, and bonding fibers. In a preferred embodiment, the composite is an airlaic, thermally-bonded composite.

An orifice 2145 is preferably provided in the backing layer 2140 to allow a negative pressure to be applied to the dressing 2100. A suction port 2150 is preferably attached or sealed to the top of the backing layer 2140 over an orifice 2145 made into the dressing 2100, and communicates negative pressure through the orifice 2145. A length of tubing 2220 may be coupled at a first end to the suction port 2150 and at a second end to a pump unit (not shown) to allow fluids to be pumped out of the dressing. The port may be adhered and sealed to the backing layer 2140 using an adhesive such as an acrylic, cyanoacrylate, epoxy, UV curable or hot melt adhesive. The port 2150 is formed from a soft polymer, for example a polyethylene, a polyvinyl chloride, a silicone or polyurethane having a hardness of 30 to 90 on the Shore A scale. In some embodiments, the port 2150 may be made from a soft or conformable material, for example using the embodiments described below in FIGS. 3A-B.

Preferably the absorbent layer 2110 and the obscuring layer 2107 include at least one through hole 2146 located so as to underlie the port 2150. The through hole 2146, while illustrated here as being larger than the hole through the obscuring layer 2107 and backing layer 2140, may in some embodiments be bigger or smaller than either. Of course, the respective holes through these various layers 2107, 2140, and 2110 may be of different sizes with respect to each other. As illustrated in FIGS. 3A-C a single through hole can be used to produce an opening underlying the port 2150. It will be appreciated that multiple openings could alternatively be utilized. Additionally should more than one port be utilized according to certain embodiments of the present disclosure one or multiple openings may be made in the absorbent layer and the obscuring layer in registration with each respective port. Although not essential to certain embodiments of the present disclosure the use of through holes in the super-absorbent layer may provide a fluid flow pathway which remains unblocked in particular when the absorbent layer 2100 is near saturation.

The aperture or through-hole 2146 is preferably provided in the absorbent layer 2110 and the obscuring layer 2107 beneath the orifice 2145 such that the orifice is connected directly to the transmission layer 2105. This allows the negative pressure applied to the port 2153 to be communicated to the transmission layer 2105 without passing through the absorbent layer 2110. This ensures that the negative pressure applied to the wound site is not inhibited by the absorbent layer as it absorbs wound exudates. In other embodiments, no aperture may be provided in the absorbent layer 2110 and/or the obscuring layer 2107, or alternatively a plurality of apertures underlying the orifice 2145 may be provided.

The backing layer 2140 is preferably gas impermeable, but moisture vapor permeable, and can extend across the width of the wound dressing 2100. The backing layer 2140, which may for example be a polyurethane film (for example, Elastollan SP9109) or hydrocolloid film, having a pressure sensitive adhesive on one side, is impermeable to gas and this layer thus operates to cover the wound and to seal a wound cavity over which the wound dressing is placed. In this way an effective chamber is made between the backing layer 2140 and a wound site where a negative pressure can be established. The backing layer 2140 is preferably sealed to the wound contact layer 2102 in a border region 2200 around the circumference of the dressing, ensuring that no air is drawn in through the border area, for example via adhesive or welding techniques. The backing layer 2140 protects the wound from external bacterial contamination (bacterial barrier) and allows liquid from wound exudates to be transferred through the layer and evaporated from the film outer surface. The backing layer 2140 preferably comprises two layers; a polyurethane or hydrocolloid film and an adhesive pattern spread onto the film. The film is preferably moisture vapor permeable and may be manufactured from a material that has an increased water transmission rate when wet.

The absorbent layer 2110 may be of a greater area than the transmission layer 2105, such that the absorbent layer overlaps the edges of the transmission layer 2105, thereby ensuring that the transmission layer does not contact the backing layer 2140. This provides an outer channel 2115 of the absorbent layer 2110 that is in direct contact with the wound contact layer 2102, which aids more rapid absorption of exudates to the absorbent layer. Furthermore, this outer channel 2115 ensures that no liquid is able to pool around the circumference of the wound cavity, which may otherwise seep through the seal around the perimeter of the dressing leading to the formation of leaks.

As shown in FIG. 3A, one embodiment of the wound dressing 2100 comprises an aperture 2146 in the absorbent layer 2110 situated underneath the port 2150. In use, for example when negative pressure is applied to the dressing 2100, a wound facing portion of the port 150 may thus come into contact with the transmission layer 2105, which can thus aid in transmitting negative pressure to the wound site even when the absorbent layer 2110 is filled with wound fluids. Some embodiments may have the backing layer 2140 be at least partly adhered to the transmission layer 2105. In some embodiments, the aperture 2146 is at least 1-2 mm larger than the diameter of the wound facing portion of the port 2150, or the orifice 2145.

A filter element 2130 that is impermeable to liquids, but permeable to gases is provided to act as a liquid barrier, and to ensure that no liquids are able to escape from the wound dressing. The filter element may also function as a bacterial barrier. Typically the pore size is 0.2 µm. Suitable materials for the filter material of the filter element 2130 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the backing layer 2140 over the orifice 2145. For example the filter element 2130 may be molded into the port 2150, or may be adhered to both the top of the backing layer 2140 and bottom of the port 2150 using an adhesive such as, but not limited to, a UV cured adhesive.

In FIG. 3B, an embodiment of the wound dressing 2100 is illustrated which comprises spacer elements 2152, 2153 in conjunction with the port 2150 and the filter 2130. With the addition of such spacer elements 2152, 2153, the port 2150 and filter 2130 may be supported out of direct contact with the absorbent layer 2110 and/or the transmission layer 2105. The absorbent layer 2110 may also act as an additional spacer element to keep the filter 2130 from contacting the transmission layer 2105. Accordingly, with such a configuration contact of the filter 2130 with the transmission layer 2105 and wound fluids during use may thus be minimized. As contrasted with the embodiment illustrated in FIG. 3A, the aperture 2146 through the absorbent layer 2110 and the obscuring layer 2107 may not necessarily need to be as large or larger than the port 2150, and would thus only need to be large enough such that an air path can be maintained from the port to the transmission layer 2105 when the absorbent layer 2110 is saturated with wound fluids.

With reference now to FIG. 3C, which shares many of the elements illustrated in FIGS. 3A-C, the embodiment illustrated here comprises the backing layer 2140, masking layer 2107, and absorbent layer 2110, all of which have a cut or opening made therethrough which communicate directly to the transmission layer 2105 so as to form the orifice 2145. The suction port 2150 is preferably situated above it and communicates with the orifice 2145.

In particular for embodiments with a single port 2150 and through hole, it may be preferable for the port 2150 and through hole to be located in an off-center position as illustrated in FIGS. 3A-C and in FIG. 1. Such a location may permit the dressing 2100 to be positioned onto a patient such that the port 2150 is raised in relation to the remainder of the dressing 2100. So positioned, the port 2150 and the filter 2130 may be less likely to come into contact with wound fluids that could prematurely occlude the filter 2130 so as to impair the transmission of negative pressure to the wound site.

FIG. 4A illustrates an exploded view of a dressing 3400 for use in negative pressure wound therapy. Although this figure illustrates a dressing having one particular shape, the construction of the layers can be applied to any of the embodiments identified below, including FIGS. 8A-B, and any of the dressing shapes and configurations described in the patent applications incorporated by reference herein. The dressing 3400 comprises a release layer 3480, wound contact layer 3460, a transmission layer 3450, an acquisition distribution layer 3440, an absorbent layer 3430, an obscuring layer 3420, and a backing layer 3410. The dressing 3400 may be connected to a port. At least the wound contact layer 3460, transmission layer 3450, absorbent layer 3430, obscuring layer 3420, and backing layer 3410 may have properties as described with respect to particular embodiments above, such as the embodiments of FIGS. 3A-C, as well as or instead of the properties described below.

The dressing 3400 may comprise a wound contact layer 3460 for sealing the dressing 3400 to the healthy skin of a patient surrounding a wound area. Certain embodiments of the wound contact layer may comprise three layers: a polyurethane film layer, a lower adhesive layer and an upper adhesive layer. The upper adhesive layer may assist in maintaining the integrity of the dressing 3400, and the lower adhesive layer may be employed for sealing the dressing 3400 to the healthy skin of a patient around a wound site. As described above, in some embodiments with respect to FIGS. 3A-C, some embodiments of the polyurethane film layer may be perforated.

Some embodiments of the polyurethane film layer and upper and lower adhesive layers may be perforated together after the adhesive layers have been applied to the polyurethane film. In some embodiments a pressure sensitive adhesive, which may be a silicone, hot melt, hydrocolloid or acrylic based adhesive or other such adhesives, may be formed on both sides or optionally on a selected one side of the wound contact layer. In certain embodiments, the upper adhesive layer may comprise an acrylic pressure sensitive adhesive, and the lower adhesive layer may comprise a silicone pressure sensitive adhesive. In other embodiments the wound contact layer 3460 may not be provided with adhesive. In some embodiments, the wound contact layer 3460 may be transparent or translucent. The film layer of the wound contact layer 3460 may define a perimeter with a rectangular or a square shape. A release layer 3480 may be removably attached to the underside of the wound contact layer 3460, for example covering the lower adhesive layer, and may be peeled off using flaps 3481. Some embodiments of the release layer 3480 may have a plurality of flaps extending along the length of the layer 3480.

Some embodiments of the dressing 3400 may comprise a spacer or transmission layer 3450. The transmission layer 3450 may comprise a porous material or 3D fabric configured to allow for the passage of fluids therethrough away from the wound site and into the upper layers of the dressing 3400. In particular, the transmission layer 3450 can ensure that an open air channel can be maintained to communicate negative pressure over the wound area even when the absorbent layer 3430 has absorbed substantial amounts of exudates. The transmission layer 3450 should remain open under the typical pressures that will be applied during negative pressure wound therapy as described above, so that the whole wound site sees an equalized negative pressure.

Some embodiments of the transmission layer 3450 may be formed of a material having a three dimensional structure. For example, a knitted or woven spacer fabric (for example Baltex 7970 weft knitted polyester) or a non-woven fabric can be used. In some embodiments, the transmission layer 3450 can have a 3D polyester spacer fabric layer. This layer can have a top layer which is a 84/144 textured polyester, and a bottom layer which can be a 100 denier flat polyester and a third layer formed sandwiched between these two layers which is a region defined by a knitted polyester viscose, cellulose or the like monofilament fiber. In use, this differential between filament counts in the spaced apart layers tends to draw liquid away from the wound bed and into a central region of the dressing 3400 where the absorbent layer 3430 helps lock the liquid away or itself wicks the liquid onwards towards the cover layer 3410 where it can be transpired. Other materials can be utilized, and examples of such materials are described in U.S. Patent Pub. No. 2011/0282309, which are hereby incorporated by reference and made part of this disclosure. However, the transmission layer 3450 may be optional, and for example may be optional in embodiments of the dressing 3400 which comprise the acquisition distribution layer 3440, described below.

Some embodiments may comprise a wicking or acquisition distribution layer (ADL) 3440 to horizontally wick fluid such as wound exudate as it is absorbed upward through the layers of the dressing 3400. Lateral wicking of fluid may allow maximum distribution of the fluid through the absorbent layer 3430 and may enable the absorbent layer 3430 to reach its full holding capacity. This may advantageously increase moisture vapor permeation and efficient delivery of negative pressure to the wound site. Some embodiments of the ADL 3440 may comprise viscose, polyester, polypropylene, cellulose, or a combination of some or all of these, and the material may be needle-punched. Some embodiments of the ADL 3440 may comprise polyethylene in the range of 40-150 grams per square meter (gsm).

The dressing 3400 may further comprise an absorbent or superabsorbent layer 3430. The absorbent layer can be manufactured from ALLEVYN™ foam, Freudenberg 114-224-4 and/or Chem-Posite™11C-450, or any other suitable material. In some embodiments, the absorbent layer 3430 can be a layer of non-woven cellulose fibers having superabsorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid.

For example, some embodiments of the absorbent layer 3430 may comprise a layered construction of an upper layer of non-woven cellulose fibers, superabsorbent particles (SAP), and a lower layer of cellulose fibers with 40-80% SAP. In some embodiments, the absorbent layer 3430 may be an air-laid material. Heat fusible fibers can optionally be used to assist in holding the structure of the pad together. Some embodiments may combine cellulose fibers and air-laid materials, and may further comprise up to 60% SAP. Some embodiments may comprise 60% SAP and 40% cellulose. Other embodiments of the absorbent layer may comprise between 60% and 90% (or between about 60% and about 90%) celluose matrix and between 10% and 40% (or between about 10% and about 40%) superabsorbent particles. For example, the absorbent layer may have about 20% superabsorbent material and about 80% cellulose fibers. It will be appreciated that rather than using super-absorbing particles or in addition to such use, super-absorbing fibers can be utilized according to some embodiments of the present invention. An example of a suitable material is the Product Chem-Posite™ 11 C available from Emerging Technologies Inc (ETi) in the USA.

Super-absorber particles/fibers can be, for example, sodium polyacrylate or carbomethoxycellulose materials or the like or any material capable of absorbing many times its own weight in liquid. In some embodiments, the material can absorb more than five times its own weight of 0.9% WAN/W saline, etc. In some embodiments, the material can absorb more than 15 times its own weight of 0.9% W/W saline, etc. In some embodiments, the material is capable of absorbing more than 20 times its own weight of 0.9% WAN/W saline, etc. Preferably, the material is capable of absorbing more than 30 times its own weight of 0.9% W/WA saline, etc. The absorbent layer 3430 can have one or more through holes 3431 located so as to underlie the suction port.

Some embodiments of the present disclosure may optionally employ a masking or obscuring layer 3420 to help reduce the unsightly appearance of a dressing 3400 during use due to the absorption of wound exudate. The obscuring layer 3420 may be a colored portion of the absorbent material, or may be a separate layer that covers the absorbent material. The obscuring layer 3420 may be one of a variety of colors such as blue, orange, yellow, green, or any color suitable for masking the presence of wound exudate in the dressing 3400. For example, a blue obscuring layer 3420 may be a shade of blue similar to the shade of blue commonly used for the material of medical gowns, scrubs, and drapes. Some embodiments of the obscuring layer 3420 may comprise polypropylene spunbond material. Further, some embodiments of the obscuring layer 3420 may comprise a hydrophobic additive or coating. Other embodiments may comprise a thin fibrous sheet of 60, 70, or 80 gsm.

The obscuring layer may comprise at least one viewing window 3422 configured to allow a visual determination of the saturation level of the absorbent layer. The at least one viewing window 3422 may comprise at least one aperture made through the obscuring layer. The at least one viewing window 3422 may comprise at least one uncolored region of the obscuring layer. Some embodiments of the obscuring layer may comprise a plurality of viewing windows or an array of viewing windows.

The masking capabilities of the obscuring layer 3420 should preferably only be partial, to allow clinicians to access the information they require by observing the spread of exudate across the dressing surface. An obscuring layer 3420 may be partial due to material properties allowing wound exudate to slightly alter the appearance of the dressing or due to the presence of at least one viewing window 3422 in a completely obscuring material. The partial masking nature of the obscuring layer 3420 enables a skilled clinician to perceive a different colour caused by exudate, blood, by-products etc. in the dressing allowing for a visual assessment and monitoring of the extent of spread across the dressing. However, since the change in colour of the dressing from its clean state to a state with exudate contained is only a slight change, the patient is unlikely to notice any aesthetic difference. Reducing or eliminating a visual indicator of wound exudate from a patient is likely to have a positive effect on their health, reducing stress for example.

The obscuring layer 3420 can have one or more through holes located so as to underlie the suction port. Some embodiments may have a maltese cross 3421 or other shaped cutout underlying the suction port, wherein the diameter of the maltese cross 3421 is greater than the diameter of the port. This may allow a clinician to easily asses the amount of wound exudate absorbed into the layers beneath the port.

The dressing 3400 may also comprise a backing layer, or cover layer 3410 extending across the width of the wound dressing. The cover layer 3410 may be gas impermeable but moisture vapor permeable. Some embodiments may employ a polyurethane film (for example, Elastollan SP9109) or any other suitable material. For example, certain embodiments may comprise translucent or transparent 30 gsm EU33 film. The cover layer 3410 may have a pressure sensitive adhesive on the lower side, thereby creating a substantially sealed enclosure over the wound in which negative pressure may be established. The cover layer can protect the wound as a bacterial barrier from external contamination, and may allow liquid from wound exudates to be transferred through the layer and evaporated from the film outer surface.

The cover layer 3410 can have an orifice 3411 located so as to underlie the suction port. The orifice 3411 may allow transmission of negative pressure through the cover layer 3410 to the wound enclosure. The port may be adhered and sealed to the cover film using an adhesive such as an acrylic, cyanoacrylate, epoxy, UV curable or hot melt adhesive. Some embodiments may have a plurality of orifices for the attachment of multiple ports or other sources of negative pressure or other mechanisms for distributing fluid.

FIG. 4B illustrates a cross sectional view of the wound dressing 3400, displaying an embodiment of the relative thicknesses of layers of the dressing 3400. In some embodiments, the wound contact layer 3460 may be flat and the top film layer 3410 may be contoured over the inner layers of the dressing 3400. The spacer layer 3450 may be half as thick as the acquisition distribution layer 3440 in some embodiments. In some embodiments, the absorbent layer 3430 may be about 1.5 times thicker than the spacer layer 3450. The obscuring layer 3420 may be about half the thickness of the spacer layer 3450.

FIG. 4C illustrates another embodiment of a wound dressing 3900, with the various layers illustrated in an exploded view. Although this figure illustrates a dressing having one particular shape, the construction of the layers can be applied to any of the embodiments identified below, including FIGS. 8A-FIG. 11, and any of the dressing shapes and configurations described in the patent applications incorporated by reference herein. The wound dressing may comprise a release layer 3980, wound contact layer 3960, a transmission layer 3950, an acquisition distribution layer 3940, an adhesive layer 3970, an absorbent layer 3930, an obscuring layer 3920, and a backing layer 3910. At least the wound contact layer 3960, transmission layer 3950, absorbent layer 3930, obscuring layer 3920, and backing layer 3910 may have properties as described with respect to particular embodiments above, such as the embodiments of FIGS. 3A-3C, as well as or instead of the properties described below.

The dressing 3900 may be connected to a port 3990, as illustrated in FIG. 4D (shown without the release layer 3980). At least the backing layer 3910, obscuring layer 3920, absorbent layer 3930, and acquisition distribution layer 3940 may have openings underlying the port 3990, and the port 3990 may comprise a three-dimensional fabric 3997 and a filter element 3995 overlying the openings. The absorbent layer 3930 may be configured to absorb and retain exudate from a patient's wound. The absorbent layer 3930 will preferably be constructed from a material which has good absorbent qualities under negative pressure. The adhesive layer 3970 may bond an upper surface of the acquisition distribution layer 3940 to a lower surface of the absorbent layer 3930. In some embodiments of a trimmable dressing 3900, other layers may be bonded together to provide consistency with respect to layer alignment when the dressing is cut on one or more sides, such that the layers remain together when the sides of the dressing are cut, and such that there is not vertical separation of the layers at the cut portions.

Figure 5A:
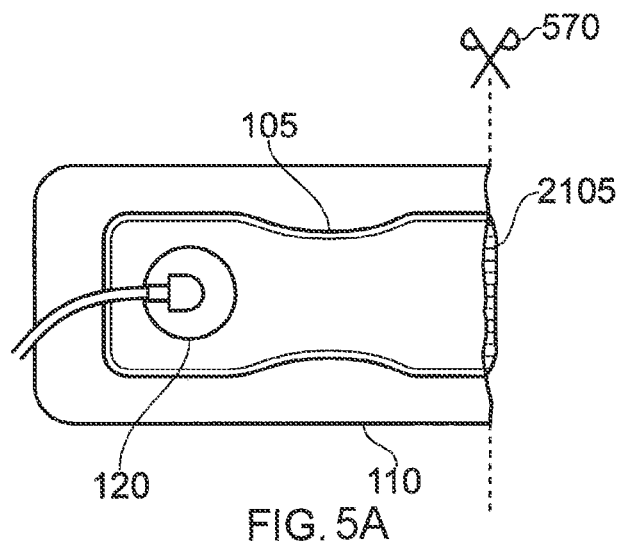
FIGS. 5A-5D and 5G illustrate embodiments of commercially available wound dressings trimmable for sealing with the present composition, to size, to profile on complex topography, or to shape around a fixation device or for puncture repair.
Figure 5B:
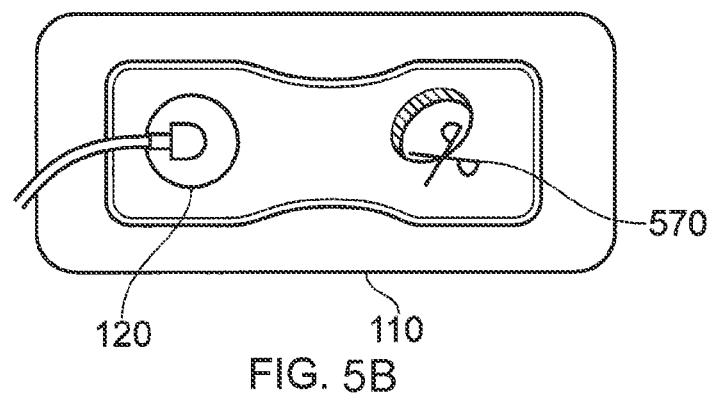
Figure 5C:
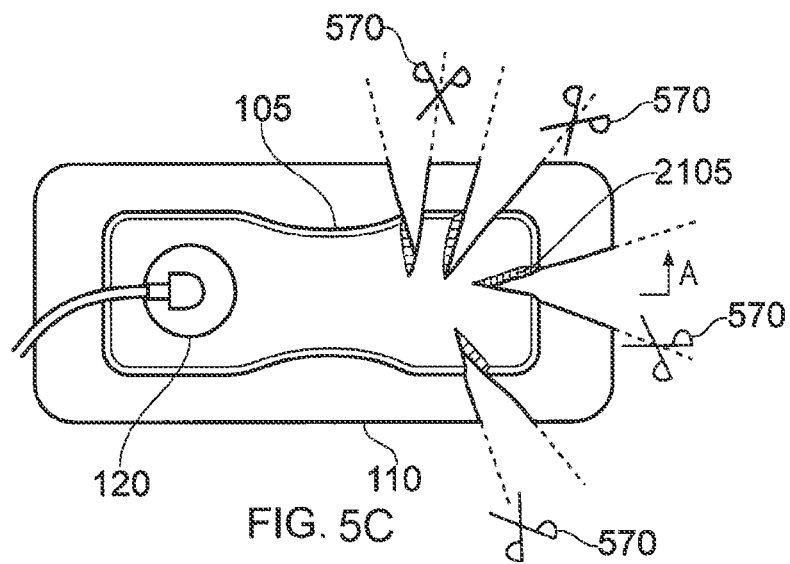
Figure 5D:
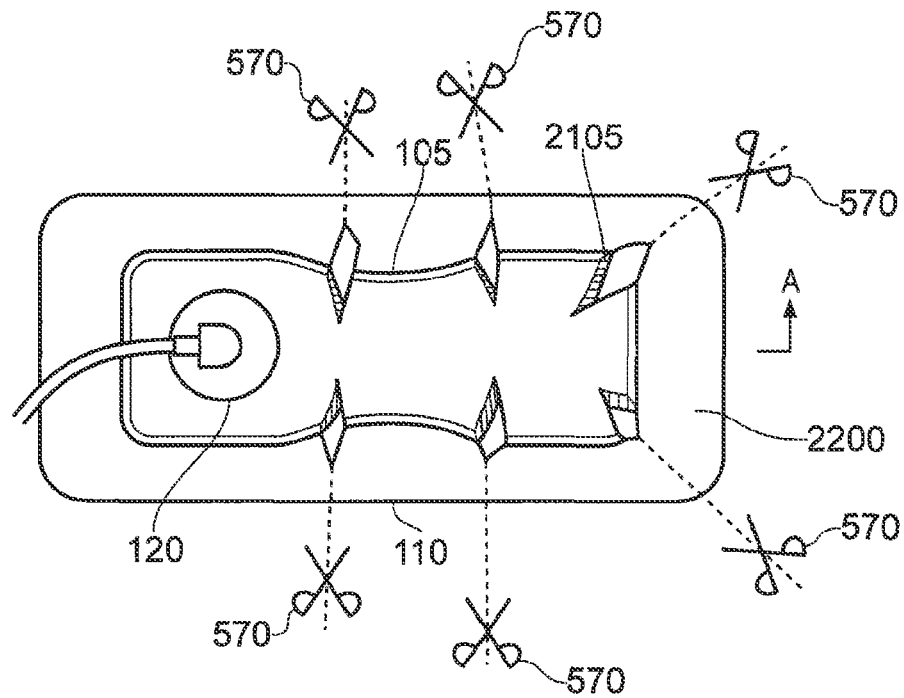

FIGS. 5A-5D illustrate trimming a TNP dressing in various manners. In FIG. 5A, the cut line is a simple truncation of the dressing, exposing the internal transmission layer; In FIG. 5B, a hole has been cut to receive a fixation device or digit; in FIG. 5C, the dressing has been cut to allow profiling to a curved body portion; in FIG. 5D the dressing has been articulated to dress a moving joint such as a knee, and in this case, transmission layer has been cut away but an amount of border region 2200 has been retained to assist in retaining and sealing the dressing at its edge.

Figure 5E:
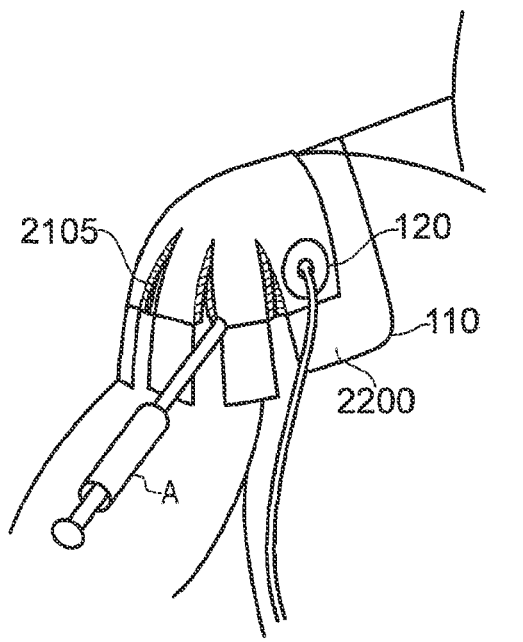
FIGS. 5E-5F illustrate the use and application and sealing of embodiments of FIGS. 5A-5D onto a patient.
Figure 5F:
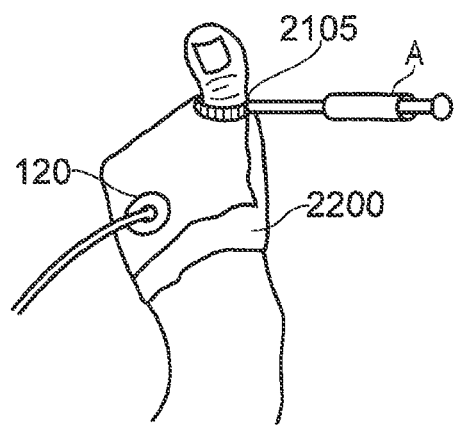
Figure 5G:
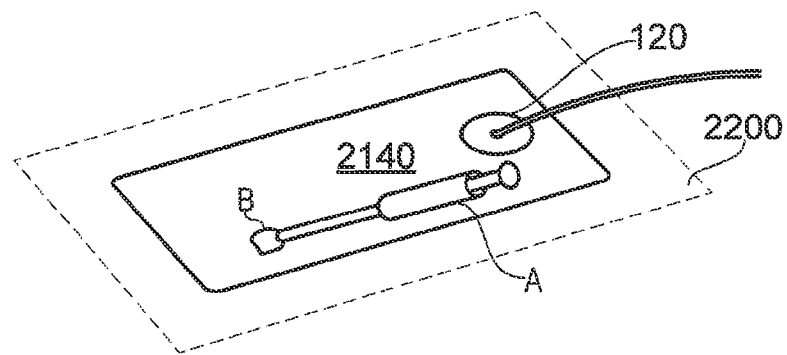

FIGS. 5E-5F illustrate applying the trimmed dressings and dispensing sealant at the exposed transmission layer portions by means of syringe A. In FIG. 5G, sealant is dispensed via syringe A to a puncture B in the backing layer 2140.

Figure 6A:
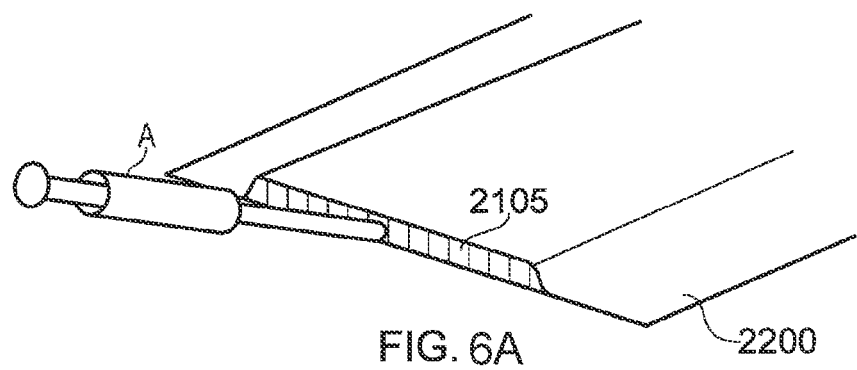
FIGS. 6A-6B and 7A-7H illustrate the spacer nozzle relationship of an applicator for dispensing composition to a trimmable dressing.

FIG. 6A illustrates in detail the means of dispensing sealant by syringe A. The syringe in this case has a nozzle aperture which allows sealant to be dispensed within the structure of the transmission layer, in FIG. 6B a suitable relationship of transmission layer height or thickness and syringe nozzle cross section and aperture is shown.

FIGS. 7A-7D illustrate different modes of dispensing sealant C: 7A—internally to the transmission layer 2105, as was shown in FIGS. 6A; 7B and 7C—bridging the exposed portion of transmission layer 2105 and skin surrounding a wound 200; and 7D—bridging the exposed portion of transmission layer 2105 and retention strips laid down on skin surrounding a wound, before the dressing has been applied. Dressings are shown comprising backing layer or sheet and transmission layer, being spacer layer, at the exposed portion 2105. The dressing may comprise further layer(s) (not shown) as hereinbefore defined at the exposed portion 2105. The main dressing portion or module of the dressing pad may contain further layers (e.g. an absorbent layer above the transmission layer) not shown. FIG. 7A shows one embodiment of sealing and mode of dispensing of composition C. In this embodiment syringe A such as a static mixer is located such that the nozzle penetrates within the exposed portion 2105. The syringe A nozzle is of cross-section area suited to be received within the exposed portion 2105 of transmission layer. Composition C is dispensed internally to the exposed portion 2105. Syringe A nozzle is inserted to penetrate a short distance within the exposed portion 2105, at intervals along the exposed face, whereby composition C is dispensed internally as a seal within the exposed portion 2105. Composition may flow to some extent on initial application, either or both laterally to the direction of dispensing and advancing and receding, flow becoming less as composition hardens or cures. This may aid in providing a continuous lateral seal, whereby dispensing intervals along the face of exposed portion 2105 may be increased. Nozzle insertion distance within the exposed portion 2105 may be selected to confine the seal spaced a short distance in from the face of the exposed portion, or to allow some spill of composition C out of the exposed portion and onto surrounding surfaces such as a preparation plate or skin 200.

Advantages of this embodiment include minimizing the amount of composition C required to be dispensed. This in turn allows use of a lower capacity syringe or static mixer A. The back pressure encountered on dispensing from a static mixer increases with the mixer volume, which in turn leads to a decrease in the viscosity which the syringe or mixer A is able to dispense. It is generally advantageous to this embodiment to deliver composition C at as high a viscosity as possible to ensure that composition C is confined within the exposed portion 2105. A further element in the total back pressure or resistance encountered on dispensing composition C is the nozzle aperture of syringe A. For this embodiment, it is desired to dispense composition C from a small aperture nozzle, and this adds to the back pressure. The advantage that this embodiment delivers of enabling a relatively small volume syringe or mixer A to be employed, allows greater freedom to operate a small aperture nozzle. Finally we have found that a seal generated by dispensing composition C internally to the exposed portion 2105, according to this embodiment, is highly effective. The dressing should be trimmed, as hereinbefore described, such that the exposed portion overlies intact skin about a wound, and does not overly the wound itself. In the case of a dressing having an adhesive or tacky wound contact layer, such as a silicone contact layer as hereinbefore described, the wound contact layer adheres to the skin 200 about the wound and seals the dressing to skin 200 about the exposed portion 2105 and the dispensed seal C. The wound contact layer is perforated or otherwise porous to allow transmission of fluids to and from the wound bed, and this may permit flow of composition C onto skin directly proximal to the internal seal. This may beneficially enhance the seal between the wound contact layer and skin 200. In the event that flow of composition to skin 200 directly proximal to the internal seal is not desired, composition C suitably has a sufficiently high viscosity to restrict flow, alternatively the wound contact layer may be non-porous or non-permeable in the region proximal to an envisaged exposed portion, for example at a bridging portion or trimmable portion as hereinbefore defined.

Figure 7B:
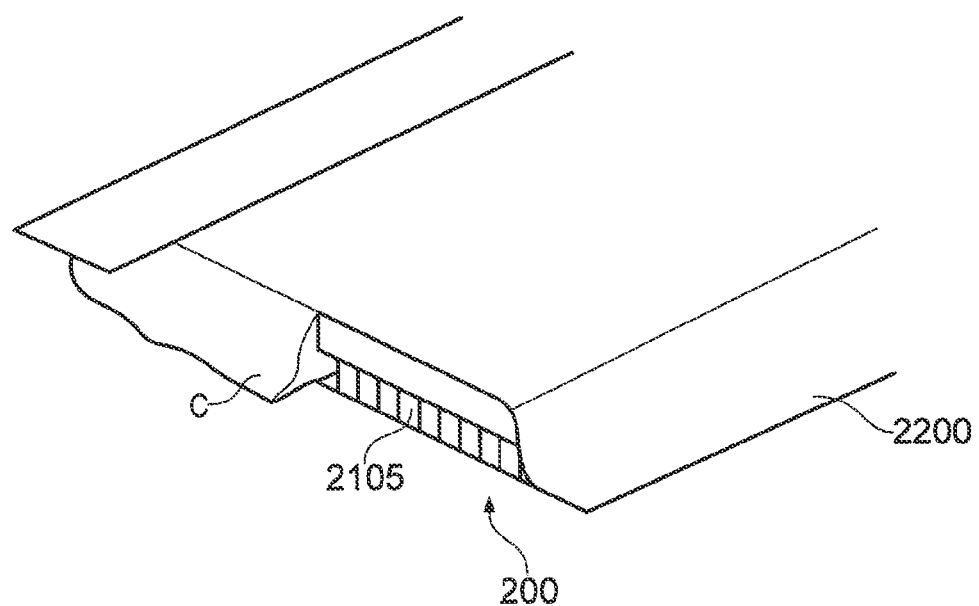
Figure 7C:
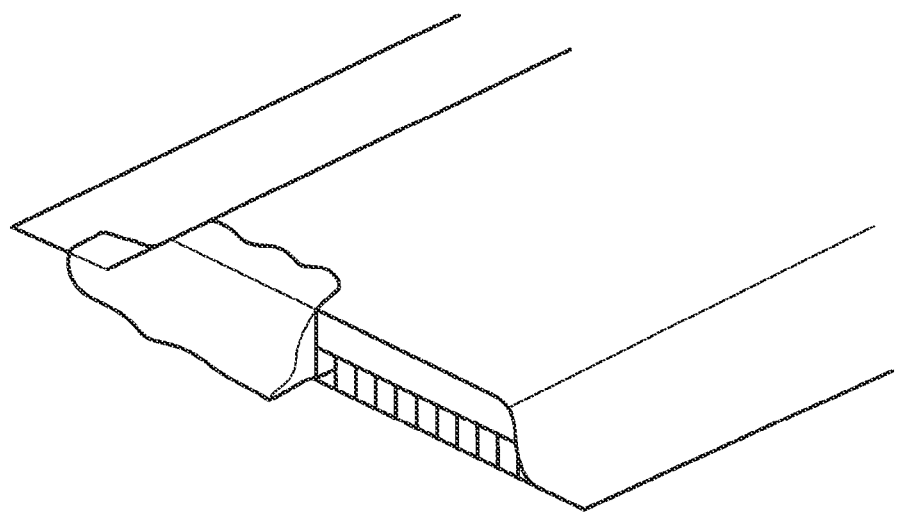

FIG. 6A may be considered, for one purpose, to illustrate dispensing composition C to a dressing having an obscuring layer whereby the dispensed seal is obscured. In contrast, the dispensed seal is shown beneath the backing layer or sheet in FIG. 7A. This illustrates that dispensing composition C to a dressing having no obscuring layer, or having window(s) in obscuring layer at bridging portions or trimmable portion(s) allows visual control of nozzle insertion distance within the exposed portion 2105, of composition C volume dispensed, and of lateral flow enabling a suitable dispensing interval across the face of exposed portion 2105 to be determined. In the case that no obscuring layer is present it is preferred that the composition incorporates ADL as hereinbefore defined as transmission layer, rather than spacer layer which may pose a risk of penetrating the backing sheet. FIG. 7C shows an extension of FIG. 7B showing the sealant on the top film. Parts are referred to using the same reference numbering as in FIG. 7B. We have found that an advantageous feature of a further embodiment of sealing and mode of dispensing is that the composition C is dispensed to the backing layer or backing sheet adjacent the exposed portion 2105, whereby composition C flows across the exposed portion 2105 totally covering the exposed portion 2105. In some cases composition C flows a short distance into or is drawn a short distance within the exposed portion 2105. It may be desired to dispense or smooth composition C onto the perimeter of the exposed portion 2105 adjoining border region 2200 as shown in FIG. 7C, and even directed slightly back along the perimeter (not shown). This has the advantage of advancing composition C a short distance at the perimeter of the exposed portion 2105, ensuring a total seal C and also securing the seal C in place. As composition C hardens or cures, the viscosity typically increases and flow ceases whereby composition C is retained at or in the dispensing location 2105 and forms an effective seal C.

Figure 7D:
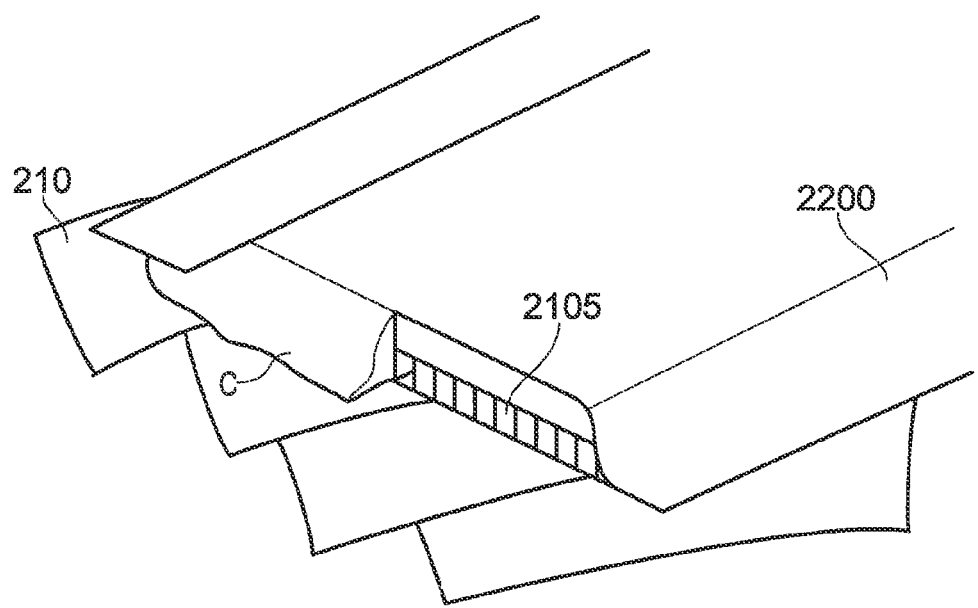

This further embodiment places performance requirements on the composition C and the resulting seal, additional to those of the first embodiment of sealing and mode of dispensing. Specifically composition C requires a continuous film to be dispensed and formed across the surface of the backing layer or sheet bridging onto the exposed portion of any additional layers and the exposed portion 2105 of the transmission layer and bridging onto the skin surface 200. Therefore composition C must be sufficiently viscous and/or cohesive to form an intact film. Such film may be thin or, as illustrated in FIGS. 7B, 7C and 7D may be of appreciable depth and/or thickness of for example from the order of depth and/or thickness of the backing sheet to the order of depth and/or thickness of the dressing or of the component layers at the exposed portion 2105 thereof. Should such film rupture or fail prior to setting or curing of composition C then the seal will fail. After setting or curing of an intact film, the exposed nature of the seal and its presentation as a film place additional requirements of robustness, both to external influences and also, to its ability to retain integrity across interfaces between adjacent layers. These requirements are likely to be greater in the case of a thin film. Preferably therefore a seal according to this further embodiment is characterized by properties of tensile strength, permanent set, and elongation at break, optionally also extensibility, in ranges as hereinbefore defined. In contrast a seal generated according to the first embodiment, as illustrated in FIG. 7A above, is supported in large part by the fabric of the dressing enclosing the seal C, whereby requirements of tensile strength, permanent set, elongation at break, are significantly lower, also being enclosed within the lower extensibility dressing, the requirement for extensibility is significantly lower than for the further embodiment of FIGS. 7B and 7D.

FIG. 7C illustrates the need for the seal of this embodiment to be effective from the backing layer surface across the exposed portion 2105. As will be apparent, a seal across the exposed portion alone is susceptible to failure at the interface of the backing sheet and exposed portion and any intervening layers.

The further embodiment illustrated by FIGS. 7B to 7D is likely to be more effective when adopted in relation to a dressing comprising no additional layers as hereinbefore defined, thereby better resisting strains introduced by separation at the interface of additional layer(s) and transmission layer. Additional layer(s) if present may beneficially be secured at their interfaces with each other and with transmission layer, by needling, stitching and other means as known in the art.

The further embodiment of FIGS. 2 and 3 moreover requires that a seal C have low profile and/or compressibility greater than or equal to the surrounding dressing. This is of advantage in minimizing discomfort to the wearer imposed by a protruding ridge at the exposed portion 2105 of the dressing.

Figure 7E:
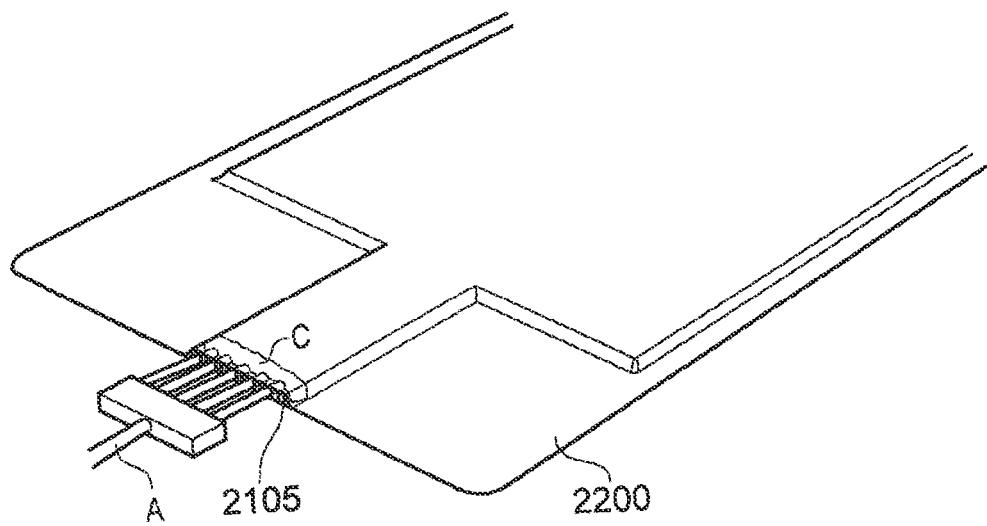
Figure 7F:
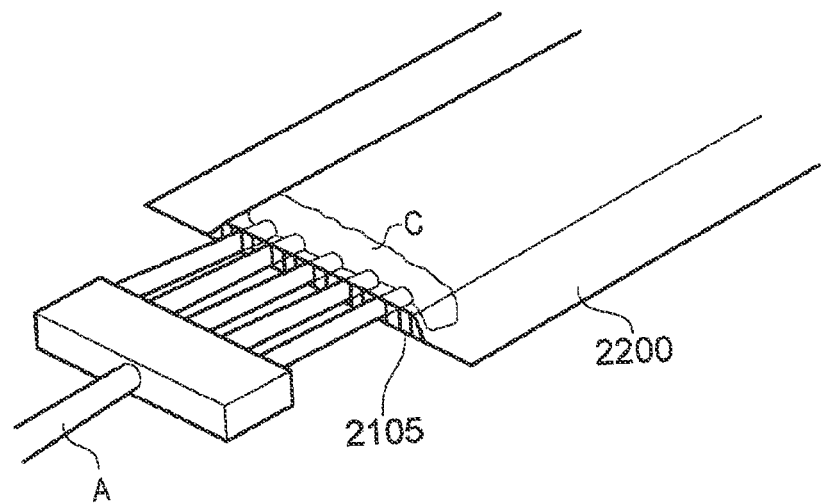
Figure 7G:
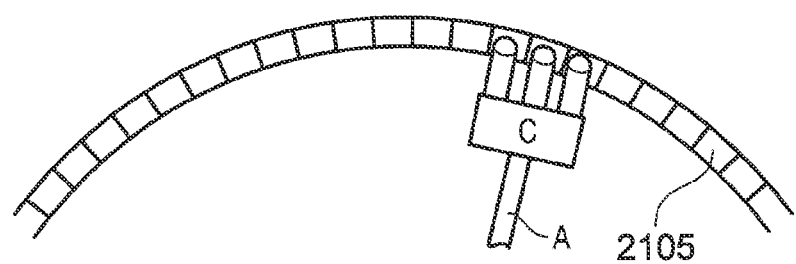
Figure 7H:
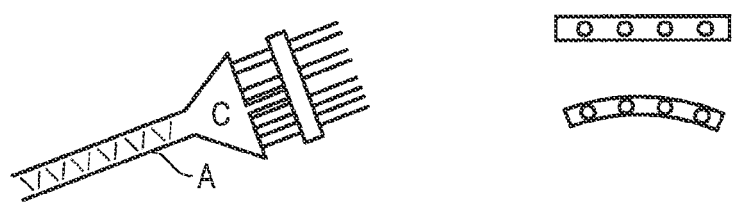
Figure 7I:
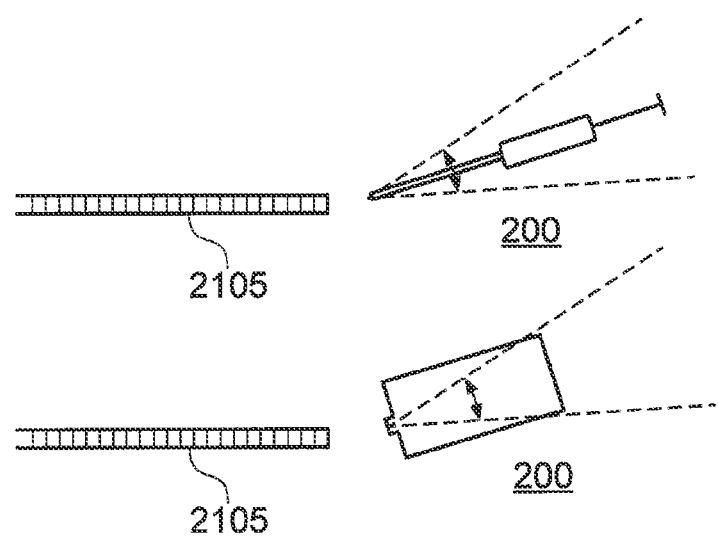

In FIGS. 7E and 7F syringe A is illustrated dispensing composition C to exposed portion 2105 of transmission layer in dressing, having border region 2200. In FIG. 7G syringe A is illustrated with modest nozzle head spread for dispensing composition C to profiled exposed portion 2105 of transmission layer. In FIG. 7H syringe A nozzle head is illustrated having combined spreader tip with plural nozzles, conformable to dispense to a profiled exposed portion and/or to dispense with obstructed access to exposed portion. In FIG. 7I, an imaginary cone illustrates maximum dispenser A dimensions to allow a shallow entry angle to exposed portion 2105 relative to the skin 200.

FIGS. 7E and 7F illustrate dispensing composition C according to the first embodiment of sealing and mode of dispensing of composition C, of FIG. 7A, using a syringe or static mixer A having a combination of spreader tip with plural nozzles as hereinbefore defined (spreader having plural projecting apertures). Parts are referred to using the same reference numbering as in FIG. 7A. A dispenser (A) is illustrated having a nozzle head comprising 5 nozzles with small nozzle cross section to deliver sealant to the interior portion within the exposed portion 2105 of transmission layer. The spread of the nozzle head matches the width of the bridging portion shown enabling dispensing on a single insertion. FIG. 7E illustrates internally dispensing composition C to the interior portion of the exposed portion 2105 of a bridging portion in the context of a relatively larger dressing. The main dressing portion or module of the dressing pad may contain further layers (e.g. an absorbent layer above the transmission layer) not shown. FIG. 7F may for example illustrate dispensing to the interior portion of the exposed portion 2105 of a bridging portion in the context of any shape or configuration dressing as hereinbefore defined. This embodiment of dispenser for and mode of dispensing composition benefits from a decreased burden and decreased requirement for accuracy on the part of the operator, an increase in mechanical accuracy of dispensing location and continuous seal formation. It may also slightly reduce the back-pressure at the syringe allowing the use of higher viscosity composition. A substantial border region 2200 is illustrated, which contributes to seal integrity.

FIG. 7G illustrates a multi nozzle head. syringe A where the overall width or spread of the head is kept modest so as to allow dispensing into exposed portion 2105 of a transmission layer on a curve, e.g. a body contour.

FIG. 7H illustrates an alternative multi nozzle head dispenser A that is flexible or deformable in two locations facilitating dispensing into exposed portion 2105 of a transmission layer on a curve, e.g. a body contour and/or dispensing into a location 2105 having obstructed access. There is a flexible arm or restraint (shown in grey) with four nozzles emerging out of the arm. This is joined to the main body (with integral static mixer) via four flexible tubes (also shown in grey).

The end on view illustrates the nozzle ends and flexible arm showing how the arm may be bent to conform to an arc. The tubes may similarly be bent (not shown) to conform to generate an angled nozzle, beneficially increasing the entry angle for dispensing.

The flexible arm is typically not elastic, i.e. it retains the shape conferred for dispensing until bent to return to its original shape or a different conformation. The flexible arm could be formed of a deformable polymer or putty or the like or it could be a mechanical flexible or deformable arm (i.e. http://snakeclamp.com/ or http://joby.com/gorillapod).

FIG. 7I illustrates an imaginary cone containing the dispenser A. This shows the maximum dimensions that may advantageously be considered in the design of the dispenser A to allow a shallow entry angle relative to the skin 200, to allow a nozzle to be inserted into an exposed portion 2105 of transmission layer in a dressing adhered to a patient 200.

FIGS. 8A and 8B illustrate various embodiments of a wound dressing 500 which may be trimmable at a bridge portion 530. The dressing 500 may comprise a backing layer 510, an absorbent layer and/or transmission layer formed in a main portion 520 and at least one additional portion 540 separated by a gap 560 and connected by a bridge portion 530, and a port 550. In some embodiments, the main portion 520, additional portion 540 and bridge portion 530 comprise at least a transmission layer such as described above between an optional wound contact layer and a backing layer 510. In any or all of these sections, the dressing 500 may further comprise an optional absorbent material such as described positioned between the backing layer 510 and the transmission layer. In some embodiments, the absorbent layer may have a similar footprint to the transmission layer. In other embodiments, the absorbent layer may be located at main portion 520 and at least one additional portion 540, but the absorbent layer may not be included in the bridge portion 530. As illustrated, the dressing has an elongate, rectangular shape, though other shapes are also contemplated. The absorbent layer preferably has a smaller footprint than the backing layer, so that the absorbent layer is completely surrounded by the backing layer. It will be appreciated that in some embodiments, the absorbent layer is an integral, one-piece layer of material that extends across the main portion 520, the additional portion 540 and in the bridge portion 530. Some embodiments may be manufactured without the port 550 and may include at least one area for attaching a port. For example, the port 550 may simply be an opening in the backing layer for attaching a separate port member.

The dressing 500 may also comprise other layers as discussed above with respect to FIGS. 3A-4B. For instance, the dressing 500 may comprise a wound contact layer which may be sealed to the backing layer 510, thereby creating an enclosed chamber for the absorbent layer and/or transmission layer and any other layers within the dressing. The wound contact layer and backing layer may be sealed along a perimeter with a certain distance from the edge of the sealed perimeter to the edge of the absorbent layer. The wound contact layer and backing layer may also be sealed together throughout some or all of the area of a gap 560 between portions of the inner layers.

The transmission or wicking layer, as described above, may be provided for the transmission of negative pressure throughout the dressing and for drawing wound exudate away from the wound site and into the upper layers of the dressing 500. Some embodiments of the transmission layer may comprise the acquisition distribution layer, as described above with respect to FIG. 4A, for lateral transmission of fluids such as wound exudate. Some embodiments may employ both a wicking layer and an acquisition distribution layer. Use of one or more of these layers may advantageously maintain fluid transmission through narrow portions of the dressing such as the bridge portions, and may keep these narrow portions from partially or completely collapsing under negative pressure.

As illustrated in FIG. 8B, the absorbent layer and/or transmission layer may comprise a main portion 520 and a plurality of additional portions 540. The additional portions may be smaller than or the same size as the main portion 550. For example, as measured along the longitudinal length of a rectangular dressing, the length of the additional portions may be smaller than the length of the main portion, and each additional portion may have the same length. As illustrated, the main portion 520 is connected to the first additional portion 540 by one bridge portion 530 aligned along the center longitudinal axis of the dressing 500, and each additional portion is connected to the next additional portion by a similar bridge. The bridge portion may in FIGS. 8A and 8B may also be located off the center axis, for example at the side of the dressing. Other embodiments may employ a plurality of bridges for connecting the portions of the dressing. For example, one embodiment may employ two bridges to connect adjacent portions, wherein the bridges are located at the side edges of the adjacent portions next to the sealed perimeter. Another embodiment may employ two bridges each located a distance away from the side edges of the adjacent portions.

In some embodiments the main portion 520 may be a precalculated minimum length, and some or all of the additional portions 540 may have lengths that can be removed for custom sizing of the dressing to a variety of lengths exceeding the minimum length. The main portion length may be longer than the additional portion lengths, or the main portion may have the same length as the additional portions. Such embodiments may be advantageous for a long incision such as a leg incision made for a vein harvest. In an embodiment, the main portion 520 may be a minimum incision length or minimum leg length, and the additional portions 540 may be included in the dressing to achieve a length up to a maximum incision length or a maximum leg length. In use, the dressing may be trimmed according to the incision or leg length of the patient across the bridge portions, for example at cut line 570 described below. In some embodiments, additional ports or port attachment sites may be located on some or all of the additional portions in order to maintain a substantially even level of negative pressure throughout a relatively long dressing.

The bridge portion 530 in FIGS. 8A and 8B creates a continuous path for negative pressure delivery between multiple portions of the dressing. The bridge portion 530 may have a width that is less than ⅛, ¼, or ⅓ the width of adjacent portions of absorbent material and/or transmission layer. A wider bridge portion allows for greater transmission of negative pressure and fluids such as wound exudate, however a narrower bridge portion is advantageous for sealing a dressing trimmed at the bridge portion. Further, patient comfort may be enhanced if the bridge portion 530 is wide enough to cover a wound or an incision. Embodiments of the dressings described herein may balance these factors according to a variety of purposes and/or considerations, and therefore the width of bridge portion 530 may vary. In some embodiments the bridge portion 530 may be approximately 15 mm wide, however other embodiments may be 10 mm to 20 mm (or about 10 mm to about 20 mm) wide or thinner or thicker. In embodiments employing a plurality of bridge portions, the bridge portions may all be a uniform width or may have varying widths. In some embodiments, the bridge portion 530 may comprise a wound contact layer, a transmission layer (which may be one or both of the wicking layer or acquisition distribution layers described above with respect to FIG. 4A), and a backing layer. Some embodiments of the bridge portion 530 may further comprise an absorbent or superabsorbent layer. The layers in the bridge portions 530 may be continuous with layers found in the portions 520 or 540 of the dressing, or they may be discrete layers positioned side-by-side.

In a dressing applied to a nonplanar surface, the bridge portions may also advantageously provide enhanced flexing of the dressing for conforming to the nonplanar surface. Further, the bridge portions may enhance side flexing capabilities of the dressing for covering a curved or arcuate incision. In some embodiments, the location and width of the bridge portions may be selected for both connecting a plurality of trimmable portions as well as for flexibility of the dressing.

The dressing 500 may be trimmed at or across the bridge portion 530. Although the dressing may be trimmed at any portion, trimming the dressing at bridge portion 530, for example perpendicular to the length of the dressing, enables easier sealing as a narrower cross sectional area is exposed, and thus less area requires sealing after trimming. In some embodiments, the gap 560 may have the same width as the distance from the sealed perimeter edge to the absorbent layer, such that when the dressing is trimmed along a trim line 570 adjacent to the additional portion 540 the sealed perimeter around the inner layer(s) is substantially unchanged. In some embodiments this width may be approximately 2.5 cm, and in other embodiments may be any width suitable for maintaining the seal between the backing layer and the wound contact layer. It will be appreciated that the dressing may be trimmed at locations other than the illustrated trim line 570, which is included for illustrative purposes only, for example at a trim line in the center of the bridge portion 530 or at a diagonal or curved trim line.

In some embodiments, the absorbent layer and/or other layers of the wound dressing may be prescored for sizing. Other layers, such as the transmission layer or acquisition distribution layer, may also be prescored. The backing layer may not be scored, as a through hole may limit the ability of the backing layer to function as a bacterial barrier or compromise the ability of the dressing to maintain negative pressure. Other embodiments may include a printed or indented pattern on some or all of the layers to indicate possible trim lines.

After trimming, the dressing 500 may be sealed by an adhesive strip, a piece of a sealing drape, by another dressing, or by a sealant. In some embodiments, a retention strip may be applied at the interface of the dressing edge and the skin. The retention strips may be applied to cover trimmed dressing borders. In some embodiments the retention strips may comprise a pressure-sensitive adhesive on the lower surface, and in other embodiments may be applied over a sealant. It will be appreciated that any other adhesive method or mechanism may be used to seal the dressing. For example, a sealant may be applied with a tool such as a syringe around the trimmed area in order to reseal the chamber of the dressing or to seal the dressing to a patient. Some embodiments of the dressing may be self-sealing.

FIGS. 8C and 8D illustrate removing a portion of dressing from the dressings of FIGS. 8A and 8C thereby exposing a bridging portion of transmission layer 22105 which can be sealed before or after applying the dressing to a wound site, by means of sealant C dispensed from syringe A. In the case of FIG. 8C, the dressing may simply be suited to a particular ulcer size, whilst in the case of FIG. 8D, the dressing is admirably suited to dressing a vein harvest wound running the length of a subject's leg.

FIG. 9A illustrates an embodiment of a trimmable wound dressing 600 comprising a plurality of portions or cells 620. The dressing 600 may comprise a sealed perimeter 610 of a backing layer and a wound contact layer, a plurality of cells 620, a plurality of bridges 630 connecting adjacent portions, and a port member 640. As described above, the dressing 600 may be trimmed at the bridge portions and sealed along the trim line. Each of the cells 620 may include absorbent material and/or a transmission layer as described above, along with other optional layers. The bridge portions 630 may comprise a wound contact layer, a transmission layer (which may be one or both of the wicking layer or acquisition distribution layers described above with respect to FIG. 4A), and a backing layer. Some embodiments of the bridge portions 630 may further comprise an absorbent or superabsorbent layer. The layers in the bridge portions 630 may be continuous with layers found in the cells 620, or they may be discrete layers positioned side-by-side.

As illustrated, the dressing comprises a 4×4 array of cells 620. Other embodiments may comprise any suitable array of cells, or may be configured as a long rolled dressing N cells wide. The cells may be connected by one or more narrow bridge portions 630 and separated by gaps 650. The backing layer and wound contact layer may be sealed together throughout the gaps. By trimming at the bridge portions 630, the integrity of the dressing may be maintained even as the dressing is significantly resized. For example, the dressing may be trimmed so that only one inner cell or a group of inner cells remain, and the layers of the dressing will not separate due to the sealing of the backing layer and wound contact layer throughout the area of the gaps 650.

In some embodiments, the center cells of the dressing 600 may be removed. This may provide benefits, for example, when the dressing is used to cover a grafted skin flap or sutured skin flap. The dressing may be resized so that the unsutured skin is substantially uncovered by the dressing. Thus, the removed sections would otherwise cover the healthy skin of the flap. Covering the healthy skin with the dressing potentially creates problem such as exposing the wound to bacteria on the surface of the flap and exposing the healthy skin of the flap to excess moisture. The dressing may also be resized accordingly to cover circular, curved, or otherwise irregularly shaped suture lines.

The port member 640 may be located, as illustrated, on a corner cell of the dressing 600. However, in other embodiments the port may be located on a different cell. Some embodiments may employ multiple ports, each port connected to a different cell. For example, a large dressing or longed rolled dressing may comprise a port at an edge cell of every N rows, such every as four rows or five rows. Some embodiments may, instead of the illustrated port member 640, comprise a port attachment site or sites.

FIG. 9B illustrates removing a portion of dressing from the dressing of FIG. 9A thereby exposing multiple bridging portions of transmission layer which can be sealed before or after applying the dressing to a wound site, by means of sealant C dispensed from syringe A. It can clearly be seen that the use of bridging portions dramatically reduces the cross-sectional area of transmission layer that must be sealed, reducing thereby both dressing time and risk of leaks.

FIG. 10A illustrates an embodiment of a trimmable wound dressing 700 comprising a plurality of portions with multiple port attachment sites 760. Similar to the dressing 600 described above, the T-shaped dressing 700 comprises a backing layer and wound contact layer having a sealed perimeter 710 around a plurality of cells 720 containing absorbent material and/or a transmission layer connected by bridge portions 730 and separated by gaps 740. The bridge portions 730 may comprise a wound contact layer, a transmission layer (which may be one or both of the wicking layer or acquisition distribution layers described above with respect to FIG. 4A), and a backing layer. Some embodiments of the bridge portions 730 may further comprise an absorbent or superabsorbent layer. The layers in the bridge portions 730 may be continuous with layers found in the cells 720, or they may be discrete layers positioned side-by-side. The backing layer and wound contact layer may also be sealed together throughout some or all of the area of the gaps 740. As described above, the dressing 700 may be trimmed at the bridge portions and sealed along the trim line. Although the dressing is illustrated as being T-shaped, this is for illustrative purposes only, and the dressing may be a variety of branched shapes. Each branch may comprise one or more cells connected by one or more bridge portions.

The dressing comprises a plurality of port attachment sites 760. Each attachment site 760 may be a hole in the backing layer and may be covered with a removable tab 760. The tab may comprise a suitable backing material with a layer of adhesive on some or all of the lower surface. Some embodiments may comprise a ring of adhesive sized to surround the hole 750 in the backing layer. The tab 760 may be removed so that a port may be attached to the backing layer over the hole 750 for transmission of negative pressure into the dressing 700. In some embodiments, port attachments may be secured at just one port attachment site. In other embodiments, port attachments may be secured over a plurality of attachment sites as needed for transmission of negative pressure throughout the dressing. Some ports may comprise an adhesive on the lower surface thereof for attachment to the dressing. Some embodiments of the dressing may comprise an adhesive layer for attaching the port.

FIG. 10B illustrates removing a portion of dressing from the dressing of FIG. 10A thereby exposing a bridging portion of transmission layer which can be sealed before or after applying the dressing to a wound site, by means of sealant C dispensed from syringe A. It car clearly be seen that this form of trimmable dressing is suitable for difficult to dress wounds which may require some visual inspection and comparison with dressing configurations, for example in the case of a flap wound.

FIG. 11A illustrates an embodiment of a trimmable wound dressing 800 with multiple port attachment sites 840. The dressing comprises a backing layer and wound contact layer having a sealed perimeter 710, an absorbent layer 820, a spacer layer 830 below the absorbent layer, and a plurality of holes 840 in the backing layer covered by tabs 850. The spacer layer 830 may be one or both. of the transmission layer and acquisition distribution layer discussed above. It will be appreciated that in some embodiments, only one of the absorbent layer or spacer layer may be provided, with the other layer being optional.

The dressing 800 is configured as a roll with port attachment sites 840 spaced a distance apart along the upper surface. In some embodiments this distance may be uniform between all port attachment sites, and in other embodiments the distance may vary. The dressing roll may be custom sized by unrolling a length of dressing, trimming the dressing, sealing the two sides, and attaching a port or ports to one or more port attachment sites. In some embodiments, unused port attachment sites 840 may remain sealed by adhesive tabs 850. In some embodiments, the spacer layer 830, and optionally the absorbent layer 820, may comprise a bridge portion or plurality of bridge portions located between each port attachment site for ease of sealing a trimmed dressing. It will be appreciated that any of the dressings described above may be configured as a trimmable roll with a plurality of port attachment sites located a distance apart on the roll. For example, an elongate dressing configured as a roll may include narrower bridging portions spaced along a length of the dressing between port attachment sites to facilitate trimming of the dressing to a suitable size.

FIG. 11B illustrates removing a portion of dressing from the dressing of FIG. 11A thereby exposing multiple bridging portions of transmission layer which can be sealed before or after applying the dressing to a wound site, by means of sealant C dispensed from syringe A.

Such adaptable, resizable dressings may provide the advantage of reducing the inventory of dressings that a hospital or clinic is required to keep. Rather than maintaining a large inventory of dressings consisting of a multitude of shapes and sizes for all possible wound or incision sites, a hospital or clinic may only require one or several of the dressings described herein which can be modified to suit any patient needs. Further, it may be advantageous from a manufacturing perspective to produce adaptable dressings.

Overview of Example Layer Materials

FIGS. 12A and 12B illustrate one embodiment of spacer layer, or transmission layer, material which may be used in any of the dressing embodiments described above, and which may also be used in any of the port or fluidic connector embodiments described above. The spacer or transmission material is preferably formed of a material having a three dimensional structure, and may have a top layer and a bottom layer comprising a knit pattern. For example, a knitted or woven spacer fabric (for example 8altex 7970 weft knitted polyester) or a non-woven fabric could be used. The top and bottom fabric layers may comprise polyester, such as 84/144 textured polyester or a flat denier polyester. Other materials and other linear mass densities of fiber could of course be used. In some embodiments, the top and bottom fabric layers may be the same pattern and the same material, and in other embodiments they may be different patterns and/or different materials. The top fabric layer may have more filaments in a yarn used to form it than the number of filaments making up the yarn used to form the bottom fabric layer, in order to control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. FIG. 12A illustrates one possible knit pattern for a top or bottom fabric layer.

As illustrated in the side view of FIG. 12B, between the top and bottom fabric layers may be a plurality of filaments. The filaments may comprise a monofilament fiber or a multistrand fiber, and may be knitted polyester viscose or cellulose. In some embodiments, a majority of the filaments, by volume, may extend vertically (that is, perpendicular to the plane of the top and bottom layers), or substantially or generally vertically. In another embodiment, 80%-90% (or approximately 80% to approximately 90%) of the filaments or more, by volume, may extend vertically, or substantially or generally vertically. In another embodiment, all or substantially all of the filaments, by volume, may extend vertically, or substantially or generally vertically. In some embodiments, a majority, 80%-90% (or approximately 80% to approximately 90%) of the filaments or more, or even all or substantially all of the filaments, extend upward from the bottom fabric layer and/or downward from the top fabric layer, and in some embodiments, such filaments extend over a length more than half the distance between the top and bottom fabric layers. In some embodiments, a majority, 80%-90% (or approximately 80% to approximately 90%) of the filaments or more, or even all or substantially all of the filaments, span a distance that is greater in a direction perpendicular to the top and bottom fabric layers (a vertical direction) than in a direction parallel to the top and bottom fabric layers (a horizontal direction). The orientation of such filaments may promote vertical wicking of fluid through the spacer layer. In some embodiments, the ratio of the amount of fluid wicked vertically through the spacer material to the amount of fluid wicked laterally across the spacer material when under negative pressure may be 2:1 or more, or approximately 2:1 or more, or may be up to 10:1 or more, or approximately 10:1 or more, in some embodiments. Such filaments may also keep the top and bottom layers spaced apart when exposed to compressive forces or negative pressure. Some embodiments of the spacer layer may have a tensile strength that substantially prevents tearing by typical force applied by human hands, and accordingly would need to be severed by other means, such as being cut or sliced, if implemented in a trimmable dressing.

FIGS. 13A-13D illustrate one embodiment of acquisition distribution layer (ADL) material which may be used in any of the dressing embodiments described above, and which may also be used in any of the port or fluidic connector embodiments described above. To those versed in the art of acquisition distribution layers it would be obvious that other ADL materials may be used to achieve a similar effect.

FIG. 13A illustrates a backscatter scanning electron microscope (SEM) plan view of a sample portion of acquisition distribution layer material at 140× magnification. FIG. 13B illustrates an SEM cross sectional view at 250× magnification. As illustrated in FIG. 13B, a majority of the fiber volume may extend horizontally (that is, parallel to the plane of the top and bottom surfaces of the material), or substantially or generally horizontally. In another embodiment, 80%-90% (or approximately 80% to approximately 90%) or more of the fiber volume may extend horizontally, or substantially or generally horizontally. In another embodiment, all or substantially all of the fiber volume may extend horizontally, or substantially or generally horizontally. In some embodiments, a majority, 80%-90% (or approximately 80% to approximately 90%) of the fibers or more, or even all or substantially all of the fibers, span a distance perpendicular to the thickness of the ADL material (a horizontal or lateral distance) that is greater than the thickness of the ADL material. In some embodiments, the horizontal or lateral distance spanned by such fibers is 2 times (or about 2 times) or more, 3 times (or about 3 times) or more, 4 times (or about 4 times) or more, 5 times (or about 5 times) or more, or 10 times (or about 10 times) or more the thickness of the ADL material. The orientation of such fibers may promote lateral wicking of fluid through the ADL material. This may more evenly distribute fluid such as wound exudate throughout the ADL material. In some embodiments, the ratio of the amount of fluid wicked laterally across the ADL material to the amount of fluid wicked vertically through the ADL material under negative pressure may be 2:1 or more, or approximately 2:1 or more, or may be up to 10:1 or more, or approximately 10:1 or more, in some embodiments.

FIG. 13C is a two dimensional microtomographic cross sectional view of a compressed portion of a sample of ADL material which is approximately 9.2 mm long. FIG. 13D is an SEM cross sectional view at 130× magnification of the compressed portion illustrated in FIG. 13C. Such compressed portions may occur in the ADL material may occur due to the application of pressure to the material. FIGS. 13C and 13D further illustrate the horizontal network of ADL fibers.

FIGS. 14A and 14B illustrate one embodiment of absorbent material which may be used in any of the dressing embodiments described above. FIG. 14A illustrates a three dimensional microtomographic cross sectional view of a sample of absorbent material, depicting a fibrous composition interspersed with superabsorbent particles. The absorbent material may, for example, be any of the materials described in U.S. Patent Pub. No. 2012/308780, titled "Absorbent Structure," filed May 25, 2012, the contents of which are hereby incorporated by reference in their entirety.

FIG. 14B is a cross sectional schematic diagram of an embodiment of the absorbent material illustrating a plurality of layers within the absorbent material. The absorbent material may have a textured layer 4210 on one side of a fibrous network, the fibrous network defining the bulk of the absorbent material and comprising layers 4220, 4240, and 4250. Superabsorbent particles 4230 may be dispersed throughout layers 4220, 4240, and 4250. The textured layer 4210, also referred to as the "tissue dispersant layer" in above portions of this specification, may be configured to laterally transmit fluid. Though depicted as the lowermost layer of the absorbent material, the textured layer 4210 may in some embodiments be positioned as the uppermost layer of the absorbent material, and in some embodiments may be positioned as both the lowermost and uppermost layers of the absorbent material. The textured layer 4210 may comprise flat fibers 20 µm to 50 µm in width, or approximately 20 µm to approximately 50 µm in width. The textured layer 4210 may comprise 1 to 2 or approximately 1 to approximately 2 layers of the flat fibers, and the textured layer 4210 may have an overall thickness of 0.04 mm, or approximately 0.04 mm.

The bulk of the absorbent material, comprising layers 4220, 4240, and 4250, may have a thickness of 1.7 mm, or approximately 1.7 mm, or may have a thickness in the range of 0.5 mm to 5.0 mm, or about 0.5 mm to about 5.0 mm. The bulk of the absorbent material may comprise a mix of two fiber types arranged in a fibrous network, for example the cellulosic fiber having a width of 20 µm to 50 µm, or approximately 20 µm to approximately 50 µm, and the PE/PET composite fiber, described above with respect to the ADL material. The superabsorbent particles 4230 may be irregularly shaped and varied in size, and may have a diameter of up to 1 mm, or approximately 1 mm. The superabsorbent particles 4230 may comprise a sodium acrylate type material. There may be relatively fewer superabsorbent particles in a portion of the uppermost surface of the bulk of the absorbent material (the surface of layer 4250 opposite the textured layer 4210), for example in an uppermost surface having a thickness of approximately 0.1 mm.

Layer 4220 may be a liquid absorption layer configured to draw liquid upward through the material towards layers 4240 and 4250. Layer 4240 may be a storage layer configured to hold absorbed liquid. Layer 4220 may be a liquid distribution layer configured to apply a "reverse suction" effect to the liquid storage layer 4240 in order to inhibit (or substantially inhibit) absorbed liquid from leaking back down through the lower layers of the absorbent material, a phenomenon which is commonly known as "back wetting."

Superabsorbent particles 4230 may be distributed primarily within the storage layer, may extend partially into the absorption layer 4220 and liquid distribution layer 4250, or may be distributed evenly (or substantially evenly) throughout the layers. The layers 4220, 4240, and 4250 may overlap with a portion of adjacent layers, and may or may not be separable.

FIGS. 15A and 15B illustrate one embodiment of obscuring layer material which may be used in any of the dressing embodiments described above. FIG. 15A illustrates a photographic plan view of obscuring material, depicting a material comprising a fibrous network having a reoccurring regularly spaced criss-cross diamond pattern. The diamond shaped pattern may, in one embodiment, be 1.2 mm long by 1.0 mm wide, and may have a thickness of approximately 0.04 mm thick, consisting of fibers that are more densely packed relative to the surrounding area of the material. The diamond shaped pattern may increase structural stability of the fibrous network of the material, for example serving as "tacking" points. FIG. 15B illustrates a three dimensional microtomographic perspective view of the compressed diamond pattern and the surrounding uncompressed fibers.

Some embodiments of the obscuring material may comprise polypropylene spunbond material. Further, some embodiments of the obscuring material may comprise a hydrophobic additive or coating, for example a hydrophobic wash designed to permeate the fibers of the obscuring material to make the material substantially waterproof while permitting vapor permeability. Other embodiments may comprise a thin fibrous sheet of 60, 70, or 80 gsm. The fibers of the obscuring material may, in one embodiment, comprise layers of polypropylene (PP) fibers having a smooth surface morphology, and the PP fibers may have a thickness of approximately 25 µm. In some embodiments, the obscuring material may have a thickness of 0.045 mm or about 0.045 mm, or may have a thickness in the range of 0.02 mm to 0.5 mm, or about 0.02 mm to about 0.5 mm.

FIG. 16 illustrates one embodiment of an adhesive spread on approximately one square centimeter of a film material, which may be used as the cover or backing layer in any of the dressing embodiments or fluidic connector embodiments described above. The adhesive on the film has been covered with carbon powder for ease of illustrating the spread of the adhesive. The adhesive may comprise, for example, an acrylate type adhesive, for example K5 adhesive, and may be laid down in a criss-cross pattern. In some embodiments, the adhesive material may cover approximately 45.5%±approximately 1.3% of the film surface. The pattern and coverage of the adhesive may vary so long as the configuration is suitable for desired vapor permeability.

I. Overview of Additional Bridged Dressing Embodiments

FIG. 17A illustrates a plan view of a trimmable dressing 1600 embodiment wherein the number of layers present in the bridging portions 1620 of the dressing is less than in an absorbent pad portion 1630 or a secondary absorbent portion 1650 of the dressing. FIG. 17A illustrates a side view of the dressing 1600. Accordingly, the overall height of the dressing is reduced at the bridging portions 1620 relative to the absorbent pad portions. In some embodiments, the dressing can also reduce in width at the bridging portions relative to the absorbent pad portions. The dressing 1600 also includes a port 1640 for delivery of negative pressure.

The dressing 1600 includes a spacer layer 1662 in the absorbent pad portion 1630 and secondary absorbent portions 1650. An ADL 1664 extends across the length of the dressing through the absorbent pad portion 1630, secondary absorbent portions 1650, and bridging portions 1620. The ADL 1664 satisfies the testing criteria specified above and is capable of negative pressure transmission through the bridging portions 1620. In some implementations of the trimmable dressing 1600, the ADL 1664 may be constructed from an ADL material that is easier to cut than a spacer material, and may be accordingly selected for the bridging portions 1620. In other embodiments, the spacer layer 1662 may extend across the length of the dressing in addition to or instead of the ADL 1664.

In the absorbent pad portion 1630 and secondary absorbent portions 1650, the dressing 1600 includes an absorbent layer 1666 and masking layer 1668. In some embodiments, the masking layer 1668 may extend across the bridging portions 1620, and may include holes, windows, perforations, or other visual indicators for indicating to a user where to cut the dressing. For example, perforations may be arranged in a dashed or dotted line configuration along a location within a bridging portion 1620, revealing a contrasting color of the ADL 1664 beneath the masking layer 1668 to visually indicate a potential location for trimming the dressing 1600. This approach could be extended to include designs and symbology such as the symbol of a pair of scissors and/or a dotted line, or notches/chevron on each side of the masking layer, lettering indicating a "cut here" location, or the like. The interior layers 1662, 1664, 1666, 1668 are positioned between a wound contact layer 1672 and a top film layer 1674 that are sealed together around a perimeter 1610, for example a perimeter of approximately 2.5 cm in some embodiments.

This layer arrangement can provide the advantage of increased flexibility at the bridging points during wear of the dressing, easy cutting with scissors (or other means) during fitting and shaping of the dressing to a wound site, and easier sealing of cut portions. The reduced height of the bridging portions provides a smaller gap that needs to be sealed. Cut or trimmed portions can be sealed with a sealant, a sealing strip, a flexible adhesive drape, or other sealing means. In addition, use of different top layers in the absorbent pad portions compared to the bridging portions can result in a color coded dressing, making the cutting locations clear to the user. Such a dressing can be convenient for use along long incision wounds where the length varies from patient to patient, for example incisions resulting from abdominoplasty procedures, as the dressing can be trimmed according to specific patient needs.

Referring now to FIG. 18, another embodiment of a trimmable dressing 2100 is illustrated. The dressing may comprise, from bottom to top, an optional wound contact layer (not shown), a transmission layer and/or ADL over the wound contact layer, a plurality of absorbent cells over the transmission layer and/or, and a cover layer over the plurality of absorbent cells. As illustrated in FIG. 18, one embodiment of the dressing includes a border 2105, a generally rectangular transmission layer 2110, a number of absorbent cells 2115, a port 2120, and a conduit 2125 for connection of the dressing 2100 to a source of negative pressure. The border 2105 can include a cover layer as described above sealed to the healthy skin of a patient surrounding a wound in one example, or can include a cover layer sealed to a wound contact layer as described above. This cover layer may extend over the plurality of absorbent cells 2115. The port 2120 and conduit 2125 can be configured for transmitting negative pressure to the dressing 2100 from a source of negative pressure when in use.

The transmission layer 2110 can extend across the entire central pad area, and can be any material described herein, or the equivalent, having suitable permeability to gas and liquid at a minimum height and/or width. By having the transmission layer 2110 extend across the central pad area rather than only being placed in bridging areas, a more comfortable distribution of pressure over the patient's therapy site can be achieved. Such pressure distribution can be considered both from the point of view of NPWT delivery and from the point of view of protecting friable skin, where (depending on the design of the dressing) blistering can be caused at pad edges. Therefore, a continuous transmission layer can, in some embodiments, minimize the number of pad edges (i.e. using a continuous lower layer) providing an advantage for pressure distribution.

A number of absorbent cells 2115 can be included above the transmission layer 2110, and can be any of the absorbent materials described herein, for example with respect to FIGS. 3A-4D and 14A-14B. By cutting the dressing 2100 along the areas of transmission layer 2110 between adjacent cells 2115, the dressing 2100 can be adaptively sized to correspond to the shape of a patient's wound. The dressing 2100 can be sealed along cut portions by one or more of re-sealing of the cover layer and wound contact layer, through a sealant adhesive, and sealing strips in various embodiments.

Although the absorbent cells 2115 are illustrated as being triangular in shape, other variations can include circular, oval, square, rectangular, hexagonal, or other shaped cells. Further, although the absorbent cells 2115 are illustrated as being discrete portions of absorbent material, in other embodiments the absorbent cells 2115 can be connected by bridging portions.

II. Overview of Additional Layer Materials

FIGS. 19A and 19B illustrate an example of Libeltex DryWeb T28F that can be suitable for use as acquisition distribution layer material (ADL) material which may be used in any of the dressing embodiments described above, and which may also be used in any of the port or fluidic connector embodiments described above. To those versed in the art of acquisition distribution layers, also known as "surge layers," it would be obvious that other ADL materials may be used to achieve a similar effect of laterally wicking fluid. Suitable ADL materials can allow for full capacity use. Such ADL layers may be composed of multiple fiber types and be complex in structure and design.

FIG. 19A illustrates a backscatter scanning electron microscope (SEM) plan view of a sample portion of ADL material at 70× magnification. As illustrated by FIG. 19A, the ADL material can comprise a number of non-woven fibers extending at least partially horizontally (that is, parallel to the plane of the top and bottom surfaces of the material) for laterally/horizontally wicking fluid through the ADL material.

FIG. 19B illustrates an SEM cross sectional view of the ADL material at 1550× magnification. In the illustrated embodiment, the ADL material may consist of a mix of multiple fiber types. One may be a roughly cylindrical fiber. Another fiber may be a relatively flatter fiber having a centrally-located negative space. Another fiber may be a multi-component fiber that has at least one inner core fiber, in some embodiments three inner core fibers as in the illustrated sample, and an outer layer surrounding the inner core.

FIGS. 20A 20B and 20C illustrate an example of Libeltex SlimCore TL4 that can be suitable for use as acquisition distribution layer material. FIG. 20A illustrates an SEM cross sectional view of a sample portion of ADL material at 50× magnification. The ADL material can include an upper layer 2305 and a lower layer 2310 having different densities, lofts, and thicknesses. For example, the upper layer 2305 can comprise a more dense, less lofted fiber configuration and can be approximately 730 μm thick in some embodiments. The lower layer 2310 can comprise a less dense, more lofted fiber configuration and can be approximately 1200 μm thick in some embodiments. FIG. 20B illustrates an SEM plan view of a sample portion of the denser upper layer 2305 at 70× magnification, FIG. 20C illustrates an SEM plan view of a sample portion of the more lofted lower layer 2310 at 70× magnification. As illustrated by FIGS. 20A-20C, the upper and lower layers 2305, 2310 of the ADL material can comprise different densities of a number of non-woven fibers extending at least partially horizontally (that is, parallel to the plane of the top and bottom surfaces of the material) for laterally/horizontally wicking fluid through the ADL material.

As illustrated by FIGS. 20A-20C, the non-woven fibers of the various illustrated ADL materials can extend more in a horizontal direction than in a vertical direction to aid in lateral wicking of fluids through the material. In some embodiments, a majority of the fiber volume may extend horizontally, or substantially or generally horizontally. In another embodiment, 80%-90% (or approximately 80% to approximately 90%) or more of the fiber volume may extend horizontally, or substantially or generally horizontally. In another embodiment, all or substantially all of the fiber volume may extend horizontally, or substantially or generally horizontally. In some embodiments, a majority, 80%-90% (or approximately 80% to approximately 90%) of the fibers or more, or even all or substantially all of the fibers, span a distance perpendicular to the thickness of the ADL material (a horizontal or lateral distance) that is greater than the thickness of the ADL material. In some embodiments, the horizontal or lateral distance spanned by such fibers is 2 times (or about 2 times) or more, 3 times (or about 3 times) or more, 4 times (or about 4 times) or more, 5 times (or about 5 times) or more, or 10 times (or about 10 times) or more the thickness of the ADL material. The orientation of such fibers may promote lateral wicking of fluid through the ADL material. This may more evenly distribute fluid such as wound exudate throughout the ADL material. In some embodiments, the ratio of the amount of fluid wicked laterally across the ADL material to the amount of fluid wicked vertically through the ADL material under negative pressure may be 2:1 or more, or approximately 2:1 or more, or may be up to 10:1 or more, or approximately 10:1 or more, in some embodiments.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. Details of any foregoing embodiments should not be considered to be limiting unless expressly indicated as such. Embodiments may relate to any novel one, or any novel combination, of the features disclosed in this specification (including any accompanying claims, abstract and drawings), or to any novel one, or any novel combination, of the steps of any method or process so disclosed.

Herein either a full stop or comma is used as the decimal marker.

The reader's attention is directed to all papers and documents which are filed concurrently with or previous to this specification in connection with this application and which are open to public inspection with this specification, and the contents of all such papers and documents are incorporated herein by reference.

EXAMPLES

The following Examples are given as non-limiting illustration.

Compositions

Commercially available RTV-2 Si compositions having 2 Parts incorporating i), ii) and iii) as defined above, literature values of physical properties are publicly available:

P1 Cavi-Care™ (20 g), Part A and Part B polymers product code 4563 (Smith & Nephew). This is a commercially available open cell foaming in situ dressing. Guide cure time within 2 minutes P2 Mepiseal™ (3 ml), Part A and Part B polymers ref. 283100 (Mölnlycke) This is a commercially available dispensable adhesive sealant intended to seal wound exudates within a wound area from contacting intact skin. Guide cure time within 20 minutes P3 Elastosil SC870 Part A and B polymers. This is a commercially available foaming elastomer, black in colour. Guide cure time within 90 minutes. (pot life 150 s, tack free time 10-15 min, density 0.35-0.4, Shore hardness 8-12)

P4 Silpura® 2445 A/B Part A and B polymers Ref 60063054 and 60063056 (both Wacker Chemie AG). This is a commercially available elastomer for casting as alignment, shock, damping members etc in prosthetics. Guide cure time within 25 minutes P5 Silpuran 2400/18 A/B (Wacker) is an addition-curing RTV-2 silicone rubber curing to a blue coloured silicone of low hardness. It has application in flexible moulding applications for prosthetics. Guide cure time 120° C. for 1 hour.

P6 Silpuran 2111 A/B (Wacker) is a commercially available 2-part, addition-curing silicone composition curing to a soft, tacky silicone adhesive. It is suitable for use in wound dressings. Guide cure time 120° C. for 1 hour.

P7 Elastosil SC835 Part A and B polymers. This is a commercially available foaming elastomer, reddish brown in colour. Guide cure time within 90 minutes (pot life 240 s, tack free time 10-15 min, density 0.4-0.45, Shore hardness 20);

P8 Silbione RTV 4511 A/B (Bluestar)—this commercially available composition is modified to reduce cure time and temperature for application at or around a wound site.

P9 Silbione LSR 4301 A/B (Bluestar)—this commercially available liquid silicone rubber composition would not be preferred for application at or around a wound site.

Procedure A

A TNP dressing (PICO™ 15×20 cm) similar (unwaisted) to that illustrated in FIG. 1 was adhered to an acrylic or glass plate or aluminium plate, adhesive side down, and connected to a pump to establish a negative pressure, as illustrated in FIGS. 2B and 2C. Once it was established that a good seal had formed, the pump was turned off and the end portion of the dressing opposite to the pump end was removed by slicing, as shown in FIG. 5A. Removing the dressing portion exposed the transmission layer and other internal layers as shown in FIGS. 3A-3C.

Sealant composition was loaded into the cylinders of a static mixer and dispensed therefrom to coat the exposed edge of the dressing as in FIG. 17B, but with considerable overlap of both the top surface of the dressing adjacent the exposed edge, and the plate. After 90 minutes the pump was turned on again to determine whether a good seal had formed.

Example 1—CaviCare Applied to Dressing Edge

Procedure A followed as above, applying dressing to acrylic plate. The composition was dispensed, and cured within 2 minutes. In this application, the sealed dressing leaked through the open cells of the foam, although we have observed that the nature of the foam structure of this composition causes it to perform differently under different conditions for example an external load may cause cell collapse with resulting gas impermeability the composition could well be optimised to achieve cell closure. Dispensing was acceptable.

Example 2—Elastosil Applied to Dressing Edge

Procedure A followed as above, applying dressing to acrylic, glass and aluminium plates. Adhesion was better with glass than acrylic and better with aluminium than glass. The composition wads dispensed and cured and after 90 minutes the pump was turned on. Leak was significant for sealed trimmed dressing on acrylic plate and low level requiring intermittent pump activity, when sealed to glass and aluminium plates. This was a factor of adhesion to the plate, not the dressing to which adhesion was acceptable. Cured sealant was difficult to remove from acrylic and glass substrates, less so from aluminum.

Example 3—Silpuran 2445 Applied to Dressing Edge

Procedure A followed as above, applying dressing to glass plate. The composition was dispensed and left to cure overnight. The sealed dressing performed well, with very good seal established, hardly requiring the pump to come on once a negative pressure had been established within the sealed trimmed dressing initially.

Procedure B

Figure 6B:
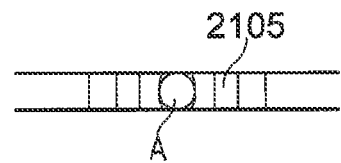

Procedure followed as for A above, applying to glass plate, but with injection of composition directly into exposed transmission (spacer) layer as illustrated in FIGS. 6A, 6B and 7A.

Example 4—CaviCare Injected Directly into Exposed Transmission Layer

Procedure B was followed. The composition did not appear to penetrate the dressing, and seemed to be blocked by the dense superabsorbent polymer (SAP) layer. On starting the pump, a very poor seal was observed, with continual pump activity unable to achieve required vacuum.

Example 5—Mepiseal Injected Directly into Exposed Transmission Layer

Result as for Example 4.

Example 6a—Elastosil SC 870 Injected Directly into Exposed Transmission Layer, SAP Removed Composition was observed to penetrate approx 1 cm within the transmission layer. On foaming and cure the backing layer top surface was observed to lift a little. Good seal, although edge of dressing lifted where composition was present in too great quantity.

Example 6b—Silpuran 2445 Injected Directly into Exposed Transmission Layer, SAP Removed As Example 6, no dressing lift, good seal and vacuum established instantly.

Example 7—Mepiseal Injected Directly into Exposed Transmission Layer, SAP Removed As Example 6b, no dressing lift.

Example 8—CaviCare Injected Directly into Exposed Transmission Layer, SAP Removed As Example 6b, but penetration was 1.5-2 cm due to foaming action, no dressing lift. No vacuum due to open cell structure.

Conclusion

Gas impermeable curable sealant dispensed externally to cover and/or internally to impregnate exposed transmission layer was surprisingly effective. Seal was absolute, and both modes were visually effective.

Further Samples.

Example 9—Procedure A as Above was Conducted on Samples as Follows 9.1—Ostomy Paste—Paste block was worked to render supple and pasted to the dressing edge. Seal was robust. Disadvantages included bioburden risk due to working before application, seal height exceeds dressing height.

9.2—Adhesive Gel Strip—Strip is tacky at both faces, one face applied to dressing gave good seal; disadvantage of tacky exposed surface, seal degraded over a few days as strip lost its tack;

9.3—Shaving Gel—The non-foaming gel was of low viscosity, such that a substantial amount of gel was pulled into the transmission layer, the dressing stopped delivering negative pressure, due to the aqueous component of the gel filling up the superabsorber layer.

9.4—Germolene—The cream was of low viscosity, such that an was pulled into the transmission layer, the seal collapsed and negative pressure leakage occurred, 9.5—Savlon Spray—The spray works by forming a liquid film on skin, water evaporates off to leave the polymer medication. In this example, the spray was unable to generate a film which could bridge the interface between absorber and transmission layer to skin. Two discrete films formed one at the backing layer surface and one at the wound model representing skin. There was no seal formed.

9.6—Elastosil SC835 (Wacker)—a foam seal of appreciable height was formed at the exposed portion, some composition was drawn in to the transmission layer, to a depth of 1-2 mm. The seal adhered strongly to the wound model and seemed robust.

9.7—Elastosil SC870 (Wacker)—a foam seal of appreciable height was formed at the exposed portion, comparable to 9.6. This composition was however more viscous to apply and the resulting seal offers lesser resilience than SC835.
Composition Measurements Methods were used as described in WO2013076450, the contents of which are incorporated herein by reference.

Example 10.1—Viscosity Measurement

Viscosity is a measure of the resistance of a fluid to deformation by shear or tensile stress and gives an indication of the fluidity of a liquid, suspension or slurry. The viscosity of a sample is measured using a rotational viscometer which simultaneously measures shear rate and shear stress. Vaseline® original, Moisturising shaving gel Nivea Men Originals and Germolene, antiseptic cream were independently tested on a cone and plate rheometer, using a 2° steel cone of diameter 60 mm. The samples were tested across a shear rate range of 5-15 s$^{-1}$, at 20° C. in accordance with DIN EN ISO:3219: 1994, Annex B. The viscosity is calculated using the shear stress at a shear rate of 10 s$^{-1}$ and is given in Pa·s.
Calculations Results NB: It was not possible to measure the viscosity of the RENASYS Ostomy Strip Paste as this was too viscous and tacky to allow suitable sample construction at the width required for the instrument.

TABLE

| viscosity | | | |
|---|---|---|---|
| | Viscosity at shear rate of 10/s, T 23° C. (Pa.s) | | |
| | Results | | Mean |
| Cavi-Care Part A | 1.643 | 1.653 | 1.648 |
| Cavi-Care Part B | 1.773 | 1.804 | 1.7885 |
| Mepiseal part from chamber with Text | 42.30 | 41.97 | 42.135 |
| Mepiseal part from chamber without Text | 34.19 | 36.10 | 35.145 |
| Silpuran 2450A | 79.40 | 76.32 | 77.86 |
| Silpuran 2450B | 25.20 | 24.39 | 24.795 |
| Silpuran 2445A | 26.07 | 20.39 | 23.23 |
| Silpuran 2445B | 11.81 | 12.01 | 11.91 |
| Silpuran 2400 | | | 1.8 |
| Elastosil 835 Part A | | | 15 |
| Elastosil 835 Part B | | | 15 |
| Elastosil 870 Part A | | | 50 |
| Elastosil 870 Part B | | | 35 |
| Vaseline ® original, pure petroleum jelly, Unilever | 23.84 | | |
| Moisturising shaving gel, Nivea Men, Originals, Beiersdorf | 11.93 | | |
| Germolene, antiseptic cream (Phenol and Chlorhexidine Digluconate), Bayer plc | 14.12 | | |

Example 10.2—Compressibility Measurements

Compressibility was determined as a measure of penetration by a plunger. Using a Setamatic Penetrometer with automatic release, timing device and standard 47.5 g plunger. The instrument was fitted with a hollow plastic cone with a stainless steel tip of mass 15 g. A dwell time of 60 seconds was used. *Measurements were recorded in triplicate (n=3).

| | Relative mass of parts | | Mean penetration/ |
|---|---|---|---|
| | A | B | 1/10 mm |
| Silpuran 2400/18 A/B* | 50.0% | 50.0% | 51 (SD 1) |
| Silpuran 2111 A/B | 50.0% | 50.0% | 200 (SD 3) |

Subject to the desired performance requirements of the system these values can be considered acceptable.

Example 10.3 Extensibility, Permanent Set, Tensile Strength, Elongation at Break

| | Results | | | | | Mean |
|---|---|---|---|---|---|---|
| | Extensibility (kgfcm$^{-2}$) | | | | | |
| Cavi-Care | 0.04 | 0.06 | 0.04 | 0.07 | 0.07 | 0.06 |
| Mepiseal | 0.07 | 0.06 | 0.09 | 0.07 | 0.08 | 0.07 |
| Silpuran 2450 | 2.60 | 2.41 | 2.42 | 2.25 | 2.70 | 2.48 |
| Silpuran 2445 | 1.20 | 1.39 | 1.32 | 1.39 | 1.60 | 1.38 |
| | Permanent Set (%) | | | | | |
| Cavi-Care | 0 | 0 | 0 | 0 | 0 | 0 |
| Mepiseal | 0 | 0 | 0 | 0 | 0 | 0 |
| Silpuran 2450 | 0 | 0 | 0 | 0 | 0 | 0 |
| Silpuran 2445 | 0 | 0 | 0 | 0 | 0 | 0 |
| | Tensile Strength (kgfcm$^{-2}$) | | | | | |
| Cavi-Care | 0.24 | 0.27 | 0.26 | 0.24 | 0.29 | 0.26 |
| Mepiseal | 1.64 | 0.95 | 1.77 | 1.69 | 2.00 | 1.61 |
| Silpuran 2450 | 47.64 | 47.64 | 55.85 | 44.37 | — | 48.87 |
| Silpuran 2445 | 37.74 | 39.73 | 39.98 | 41.16 | 37.15 | 39.15 |
| Elastosil 835 | | | | | | 450 |
| Elastosil 870 | | | | | | 350 |

-continued

|  | Results |  |  |  |  | Mean |
| --- | --- | --- | --- | --- | --- | --- |
|  | Elongation at Break (%) | | | | | |
| Cavi-Care | 92 | 90 | 83 | 73 | 120 | 92 |
| Mepiseal | 425 | 283 | 463 | 450 | 466 | 418 |
| Silpuran 2450 | 199 | 204 | 234 | 184 | — | 205 |
| Silpuran 2445 | 322 | 332 | 334 | 342 | 302 | 326 |
| Elastosil SC 870 |  |  |  |  |  | 100 |
| Elastosil SC835 |  |  |  |  |  | 80 |

Example 11—Extensibility Testing of Spacer Layer (Transmission Layer)

Baltex

| Reference | Description |
| --- | --- |
| A | Spacer Layer |
| B | Laminates made with EU33 top film, Chemposite 11C-450 Air Laid superabsorber pad, Baltex ref: 7970, batch number T0061Spacer layer and ALLEVYN Gentle Border wound contact layer (non-sterile and hand manufactured) |

Method

SOP/QPM/230 (1003423) Extensibility

Results

| A | | | |
| --- | --- | --- | --- |
| Test method | Results (kgfcm$^{-1}$) | | Mean |
| Extensibility (Direction A) 1003423 | 0.07 | 0.08 | 0.08 | 0.08 |
| Extensibility (Direction B) 1003423 | 0.07 | 0.08 | 0.07 | 0.07 |

| B | | | |
| --- | --- | --- | --- |
| Test method | Results (kgfcm$^{-1}$) | | Mean |
| Extensibility (Direction A) 1003423 | 0.58 | 0.61 | 0.59 | 0.59 |
| Extensibility (Direction B) 1003423 | 0.79 | 0.80 | 0.76 | 0.78 |

Conclusions

The spacer layer gave good (ie low) extensibility values. Extensibility was restricted once the material was incorporated into a dressing with the superabsorber pad.

Example 12—Silpuran 2400

Silpuran was subject to testing according to procedures A and B above. The results are shown as follows. This composition has a very long cure time and low viscosity and it was expected that it would simply run out of position before curing. In fact the composition demonstrated a surprisingly effective seal, however showed a dramatic performance difference depending on dispensing according to presence or absence of the absorber layer in Procedure B. The composition gave excellent results when dispensed according to Procedure B.

Silpuran 2400 was then dispensed internally according to the first embodiment procedure illustrated in Figure C1. The composition was retained admirably in the transmission layer, and only a small volume of composition was required. This enables use of a small volume syringe with associated back-pressure advantages. It was important to use a small bore nozzle to minimize run off, allowing as little composition as possible to contact skin. Dispensing again was ineffective using the Procedure A method with superabsorber layer, but was highly effective for Procedure B with single transmission layer in the trimmed portion. The transmission layer may be spacer or ADL, but with a preference for omitting obscuring layer to monitor the dispensing and seal formation, the transmission layer is preferably an ADL-type layer or a combination of ADL and spacer, minimizing the risk of spacer layer puncturing the backing layer.

Composition: Silpuran 2400/20, Part A and Part B polymers (Wacker)

Silpuran 2400
Component A
Color translucent
Viscosity (Plate/Cone) DIN EN ISO 3219 1800 mPa s
Density DIN EN ISO 2811 1.00 g/cm$^3$
Component B
Color translucent
Viscosity (Plate/Cone) DIN EN ISO 3219 1800 mPa s
Density DIN EN ISO 2811 1.00 g/cm$^3$
Product data (catalyzed A+B)
Mix ratio A:B 1:1
Color translucent
Pot life at 23° C. 21 min
Product data (cured)
Hardness Shore A ISO 868 7
Hardness Shore 00 ASTM 2240/Type 00 55
Tensile strength ISO 37 2.00 N/mm2
Elongation at break ISO 37 600%
Tear strength ASTM D 624 B 3.0 N/mm
Curing conditions: 10 min/100° C.

Run 8A

Followed as detailed in procedure A of the patent spec with application of Silpuran 2400/20.
  Dressing before application of Silpuran 2400/20
  Dressing immediately after application of Silpuran 2400/20
  A torch/flash used to examine the reflection of the silicone and ensure no pin holes were present in the composition immediately following application.
  Cured composition (90 minutes was allowed to elapse, and cure beyond manual kinetic point confirmed). Sealant was not effective as there was no cured sealant across the cut face. Gap demonstrated Run 8B Followed as detailed in procedure B of the patent spec with application of Silpuran 2400/20.
  Dressing before application of Silpuran 2400/20
  Dressing immediately after application of Silpuran 2400/20
  Cured composition (90 minutes was allowed to elapse, and cure beyond manual kinetic point confirmed) Sealant was effective when it had been dispensed into the transmission layer directly.

It was noted that whilst the spacer layer was more resilient to compression when the cured silicone was inside it then the unfilled spacer; by comparison to run 8A where the same sealant had been applied across the cut face the profile of the sealant was less pronounced and (subjectively) the rigidity was significantly less.

The following observations were made:

Significantly less sealant was needed when sealing the internal space of the transmission layer as opposed to sealing over the cut end.

The resulting finish was significantly neater when the sealant was applied into the internal space of the transmission layer as opposed to sealing over the cut end. The silicone that flowed onto the wound model came from the fact that the nozzle aperture was not sufficient to penetrate the spacer layer deeply and was thus delivering silicone close to the edge of the cut transmission layer. A dispensing nozzle with external bore small enough to penetrate the transmission layer could be inserted into the transmission layer (to a selected distance) at the time of dispensing and limit the amount of curing silicone that was able to travel the distance back out of the transmission layer.

The absence of an obscuring layer or opaque layer above the bridge in Run 8B (such as the absorbent layer present in Run 8A) allowed the user to clearly see the ingress of the sealant into the bridge during dispensing. This provided control over where to apply the sealant, how much and allowed the user to ensure that no air paths remained in the seal.

The low viscosity of Silpuran 2400/20 was a significant advantage during dispensing. It flowed well into the transmission layer and appeared to readily conform to the internal shape of the transmission layer. A low viscosity material would also have the added advantage of reducing the back pressure generated in a dispensing unit. This could be of particular importance if a dispensing nozzle with narrow aperture was used (as desired to penetrate the transmission layer) so that the back pressure generated by the liquid travelling through the resultant narrow orifice was reduced. To provide an example of the influence of back pressure, in a dispenser comprising a double barreled syringe with integral mixer it would relate to the force that the user needed to apply to the syringe plunger to eject the liquid.

Example 13 Dispenser Design

A dispenser with a single nozzle that penetrated the transmission layer could be an advantage.

A dispenser with multiple nozzles could be an advantage, however, subject to the width of this head, injecting the sealant into a dressing following body contours be limited. Therefore either the width of the mixing head should be balanced so as to ensure ease of application (wicer better) versus following body contours (narrower better). Or the mixing heads should be conformable so as to be moved to shape (ideally this would stay in position once moved) to allow the user to approximate the shape.

Thought should be given to the clearance of the dispenser given that it will be entering the transmission at an acute angle to the skin.

What is claimed is:

1. A method of treating a wound, comprising:
    providing a wound dressing comprising:
        a backing layer; and
        one or more transmission layers positioned beneath the backing layer;
    removing a portion of the wound dressing to create a main wound dressing portion with one or more exposed portions, wherein the one or more transmission layers is exposed at the one or more exposed portions;
    positioning the main wound dressing portion over a wound;
    sealing the main wound dressing portion to skin surrounding the wound;
    dispensing a composition comprising a silicone curing system to a location at or within the one or more exposed portions of the main wound dressing portion thereby sealing the one or more exposed portions; and
    wherein the composition is shear thinning or shape conforming when subject to load such that the viscosity of the composition is reduced when the composition is subject to shear forces during dispensing, the composition having viscosity in the range of 10 to 100 Pa·s.

2. The method of claim 1, wherein dispensing the composition comprises internally impregnating the one or more transmission layers at the one or more exposed portions.

3. The method of claim 2, further comprising impregnating the one or more transmission layers to a distance in the range of 0.2 to 25 mm within the one or more transmission layers.

4. The method of claim 1, further comprising applying negative pressure to the wound through the backing layer of the main wound dressing portion.

5. The method of claim 4, further comprising drawing the dispensable composition up to 25 mm within the one or more transmission layers at the one or more exposed portions via the negative pressure.

6. The method of claim 4, wherein the wound dressing exhibits no change or substantially no change in compressibility at the location of the seal on initiation of the negative pressure.

7. The method of claim 4, further comprising dispensing the dispensable composition with formation of an air-tight elastomer which is capable of containing the negative pressure.

8. The method of claim 1, wherein the dispensable composition has a viscosity in the range of 11 and 14 Pa·s.

9. The method of claim 1, wherein the dispensable composition, when cured, is conformable.

10. The method of claim 1, further comprising subjecting the dispensable composition to shear forces during application to the one or more exposed portions, wherein the dispensable composition reduces viscosity when subjected to the shear forces.

11. The method of claim 1, wherein the dispensable composition has a curing time at 23° C. in the range from 0.5 to 5 min.

12. The method of claim 1, wherein the dispensable composition has a curing time at 32° C. in the range from 0.5 to 7 min.

13. The method of claim 1, further comprising dispensing the dispensable composition directly at the exposed portion through an exposed face of the one or more transmission layers.

14. The method of claim 4, further comprising applying negative pressure to the main wound dressing after sealing the one or more exposed portions.

15. The method of claim 1, wherein the composition does not flow from the location.

16. The method of claim 1, wherein the composition is configured to be drawn into the transmission layer by negative pressure prior to curing.

17. The method of claim 1, wherein the silicone curing system comprises two or more components, the silicone curing system exhibiting zero or low tack for 0.5 to 25 minutes after mixing of the two or more components.

* * * * *

UNITED STATES PATENT AND TRADEMARK OFFICE
CERTIFICATE OF CORRECTION

PATENT NO. : 11,931,226 B2
APPLICATION NO. : 16/779436
DATED : March 19, 2024
INVENTOR(S) : Sarah Jenny Collinson Page 1 of 2

It is certified that error appears in the above-identified patent and that said Letters Patent is hereby corrected as shown below:

In the Specification

Column 5, Line 60, delete "(q)" and insert -- ($\eta$) --.

Column 7, Line 50, delete "stemiotomies," and insert -- sternotomies, --.

Column 15, Line 14, delete "rot" and insert -- not --.

Column 19, Line 27, delete "cf" and insert -- of --.

Column 20, Line 25, delete "—O—SiR$^{22}$H," and insert -- —O—SiR$^2_2$H, --.

Column 20, Line 31 (approx.), delete "P$^{ii}$—O—SiR$^{22}$H" and insert -- P$^{ii}$—O—SiR$^2_2$H --.

Column 20, Line 44 (approx.), delete "—O—SiR$^{22}$H" and insert -- —O—SiR$^2_2$H --.

Column 20, Line 47 (approx.), delete "—O—SiR$_{22}$—O—" and insert -- —O—SiR$^2_2$—O— --.

Column 20, Line 48 (approx.), delete "—O—SiR$^{23}$" and insert -- —O—SiR$^2_3$ --.

Column 20, Line 59 (approx.), delete "—O—SiR$^{22}$H" and insert -- —O—SiR$^2_2$H --.

Column 24, Line 59, delete "hydroplobic." and insert -- hydrophobic. --.

Column 25, Line 29, delete "hexatidine," and insert -- hexetidine, --.

Column 25, Line 34, delete "anasthetics" and insert -- anesthetics --.

Column 25, Line 40, delete "Heamostats" and insert -- Hemostats --.

Signed and Sealed this
Twenty-fifth Day of June, 2024

Katherine Kelly Vidal
*Director of the United States Patent and Trademark Office*

CERTIFICATE OF CORRECTION (continued)
U.S. Pat. No. 11,931,226 B2

Column 25, Line 56, delete "batroxobin" and insert -- batroxobin, --.

Column 44, Line 9, delete "2105" and insert -- 2150 --.

Column 47, Line 47, delete "celluose" and insert -- cellulose --.

Column 47, Line 62, delete "WAN/W" and insert -- W/W --.

Column 47, Line 66, delete "WAN/W" and insert -- W/W --.

Column 47, Line 67, delete "W/WA" and insert -- W/W --.

Column 49, Line 28, delete "FIGS." and insert -- FIG. --.

Column 53, Line 20, delete "head." and insert -- head --.

Column 56, Line 32, delete "22105" and insert -- 2105 --.

Column 58, Line 11, delete "car" and insert -- can --.

Column 58, Line 22, delete "both." and insert -- both --.

Column 59, Line 6, delete "8altex" and insert -- Baltex --.

Column 67, Line 30 (approx.), delete "17B," and insert -- 7B, --.

Column 69, Line 48, line Below "Calculations" insert
$$\text{Viscosity (Pa.s)} = \frac{\text{Shear stress (Pa)}}{\text{Shear rate (s}^{-1}\text{)}}$$
--.

Column 73, Line 47, delete "(wicer" and insert -- (wider --.